(12) United States Patent
Calabria et al.

(10) Patent No.: US 8,778,647 B2
(45) Date of Patent: Jul. 15, 2014

(54) METHODS OF PRODUCING ISOPRENE COMPRISING A MEMBRANE BIOREACTOR

(75) Inventors: Anthony R. Calabria, Wilmington, DE (US); Gopal K. Chotani, Cupertino, CA (US); Robin Fong, Mountain View, CA (US); Alex T. Nielsen, Kokkedal (DK); Karl J. Sanford, Cupertino, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 535 days.

(21) Appl. No.: 12/976,572

(22) Filed: Dec. 22, 2010

(65) Prior Publication Data

US 2011/0195472 A1 Aug. 11, 2011

Related U.S. Application Data

(60) Provisional application No. 61/289,352, filed on Dec. 22, 2009.

(51) Int. Cl.
*C12P 5/02* (2006.01)

(52) U.S. Cl.
USPC ......... 435/167; 435/252; 435/7.1; 435/320.1; 435/6

(58) Field of Classification Search
None
See application file for complete search history.

(56) References Cited

U.S. PATENT DOCUMENTS

| | | | | | |
|---|---|---|---|---|---|
| 5,401,891 | A | * | 3/1995 | Keenan et al. | 585/318 |
| 6,361,809 | B1 | * | 3/2002 | Christophersen et al. | 426/52 |
| 6,518,487 | B1 | * | 2/2003 | Lowe et al. | 800/298 |
| 7,132,527 | B2 | | 11/2006 | Payne et al. | |
| 8,288,148 | B2 | | 10/2012 | Cervin et al. | |
| 8,361,762 | B2 | * | 1/2013 | Beck et al. | 435/131 |
| 8,420,360 | B2 | * | 4/2013 | Calabria et al. | 435/167 |
| 8,507,235 | B2 | * | 8/2013 | Chotani et al. | 435/167 |
| 2008/0038805 | A1 | * | 2/2008 | Melis | 435/167 |
| 2010/0003716 | A1 | | 1/2010 | Cervin et al. | |
| 2010/0048964 | A1 | | 2/2010 | Calabria et al. | |
| 2010/0196977 | A1 | | 8/2010 | Chotani et al. | |
| 2010/0196988 | A1 | | 8/2010 | Rothschild et al. | |
| 2011/0046422 | A1 | | 2/2011 | McAuliffe et al. | |
| 2011/0178261 | A1 | | 7/2011 | Feher et al. | |

FOREIGN PATENT DOCUMENTS

| | | |
|---|---|---|
| WO | WO-96/35796 A1 | 11/1996 |
| WO | WO-98/02550 A2 | 1/1998 |
| WO | WO-98/02550 A3 | 1/1998 |
| WO | WO-2004/033646 A2 | 4/2004 |
| WO | WO-2004/033646 A3 | 4/2004 |
| WO | WO-2009/035700 A2 | 3/2009 |
| WO | WO-2009/035700 A3 | 3/2009 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2010/003007 A2 | 1/2010 |
| WO | WO-2010/003007 A3 | 1/2010 |
| WO | WO-2010/078457 A2 | 7/2010 |
| WO | WO-2010/078457 A3 | 7/2010 |
| WO | WO-2010/148256 A1 | 12/2010 |
| WO | WO-2011/075748 A1 | 6/2011 |

OTHER PUBLICATIONS

Anderson, M.S. et al. (Nov. 15, 1989). "Isopentenyl Diphosphate: Dimethylallyl Diphosphate Isomerase. An Improved Purification of the Enzyme and Isolation of the Gene from *Saccharomyces cerevisiae*," *J. Biol. Chem.* 264(32):19169-19175.

Aon, J.C. et al. (Feb. 2008). "Suppressing Posttranslational Gluconoylation of Heterologous Proteins by Metabolic Engineering of *Escherichia coli*," *Applied and Environmental Microbiology* 74(4):950-958.

Baba, T. et al. (2006). "Construction of *Escherichia coli* K-12 In-Frame, Single-Gene Knockout Mutants: the Keio Collection," *Mol. Syst. Biol.*, 2006.0008:1-11.

Boontawan, A. et al. (2006). "A Membrane Bioreactor for the Biotransformation of α-Pinene Oxide to Isonovalal by *Pseudomonas fluorescens* NCIMB 11671," *Applied Microbiology and Biotechnology* 69:643-649.

Bouvier, F. et al. (2005). "Biogenesis, Molecular Regulation and Function of Plant Isoprenoids," *Progress in Lipid Res.* 44:357-429.

Campbell, E.I. et al. (1989). "Improved Transformation Efficiency of *Aspergillus niger* Using the Homologus *niaD* Gene for Nitrate Reductase," *Curr. Genet.* 16:53-56.

Cherepanov, P.P. et al. (1995). "Gene Disruption in *Escherichia coli*: $Tc^R$ and $Km^R$ Cassettes with the Option of Flp-Catalyzed Excision of the Antibiotic-Resistance Determinant," *Gene* 158(1):9-14.

Choudhury, B. et al. (2006). "Lactic Acid Fermentation in Cell-Recycle Membrane Bioreactor," *Applied Biochemistry and Biotechnology* 128:171-183.

Datsenko, K.A. et al. (Jun. 6, 2000). "One-step Inactivation of Chromosomal Genes in *Escherichia coli* K-12 Using PCR Products," *PNAS* 97(12):6640-6645.

Dhe-Paganon, S. et al. (Nov. 15, 1994). "Mechanism of Mevalonate Pyrophosphate Decarboxylase: Evidence for a Carbocationic Transition State," *Biochemistry* 33(45):13355-13362.

Gräwert, T. et al. (Oct. 13, 2004, e-pub. Sep. 21, 2004). "IspH Protein of *Escherichia coli*: Studies on Iron-Sulfur Cluster Implementation and Catalysis," *J. Am. Chem. Soc.* 126(40):12847-12855.

Hedl, M. et al. (Apr. 2002). "*Enterococcus faecalis* Acetoacetyl-Coenzyme A Thiolase/3-Hydroxy-3-Methyglutaryl-Coenzyme A Reductase, a Dual-Function Protein of Isopentenyl Diphosphate Biosynthesis," *J. Bacteriol.* 184(8):2116-2122.

Hoeffler, J-F. et al. (Sep. 2002). "Isoprenoid Biosynthesis via the Methylerythritol Phosphate Pathway. Mechanistic Investigations of the 1-deoxy-$_D$-xylulose 5-phosphate Reductoisomerase," *Eur. J. Biochem.* 269(18):4446-4457.

(Continued)

*Primary Examiner* — Hope Robinson
(74) *Attorney, Agent, or Firm* — Morrison & Foerster LLP

(57) ABSTRACT

The invention provides improved methods for the production of isoprene from biological materials using a membrane bioreactor to culture isoprene-producing cells.

91 Claims, 45 Drawing Sheets

(56) References Cited

OTHER PUBLICATIONS

Ilmén, M. et al. (Apr. 1997). "Regulation of Cellulase Gene Expression in the Filamentous Fungus *Trichoderma reesei*," *Appl. Environ. Microbiol.* 63(4):1298-1306.

International Search Report mailed on May 6, 2011, for PCT Patent Application No. PCT/US2010/061913, filed on Dec. 22, 2010, published on Jun. 23, 2011, as WO 2011/075748, 3 pages.

Koga, Y. et al. (Mar. 2007). "Biosynthesis of Ether-Type Polar Lipids in Archaea and Evolutionary Considerations," *Microbiology and Molecular Biology Reviews* 71(1):97-120.

Kwon, S-G. et al. (2006). "Increase of Xylitol Productivity by Cell-Recycle Fermentation of *Candida tropicalis* Using Submerged Membrane Bioreactor," *Journal of Bioscience and Bioengineering* 101(1)13-18.

Lüttgen, H. et al. (Feb. 1, 2000). "Biosynthesis of Terpenoids: YchB Protein of *Escherichia coli* Phosphorylates the 2-hydroxy Group of 4-diphosphocytidyl-2C-methyl-$_D$-erythritol," *PNAS* 97(3):1062-1067.

Meynial-Salles, I. et al. (Jan. 1, 2008). "A New Process for the Continuous Production of Succinic Acid from Glucose at High Yield, Titer, and Productivity," *Biotechnology and Bioengineering* 99(1):129-135.

Miller, B. et al. (Jul. 2001, e-pub. May 10, 2001). "First Isolation of an Isoprene Synthase Gene from Poplar and Successful Expression of the Gene in *Escherichia coli*," *Planta.* 213(3):483-487.

Oulmouden, A. et al. (Jan. 1991). "Nucleotide Sequence of the *ERG12* Gene of *Saccharomyces cerevisiae* Encoding Mevalonate Kinase," *Curr. Genet.* 19(1):9-14.

Parekh, S.R. et al. (Feb. 1994). "Continuous Production of Acetate by *Clostridium thermoaceticum* in a Cell-Recycle Membrane Bioreactor," *Enzyme Microb. Technol* 16:104-109.

Pourquié, J. et al. (1988). "Scale Up of Cellulase Production and Utilization," *in Biochemistry and Genetics of Cellulose Degradation*, Aubert, J-P. et al. eds., Academic Press: San Diego, CA, pp. 71-86.

Rohdich, F. et al. (Oct. 12, 1999). "Cytidine 5'-triphosphate-dependent Biosynthesis of Isoprenoids: YgbP Protein of *Escherichia coli* Catalyzes the Formation of 4-Diphosphocytidyl-2-*C*-methylerythritol," *PNAS* 96(21):11758-11763.

Rohdich, F. et al. (Jun. 6, 2000). "Biosynthesis of Terpenoids: 4-Diphosphocytidyl-2C-methyl-$_D$-erythritol Synthase of *Arabidopsis thaliana*," *PNAS* 97(12):6451-6456.

Sharkey, T.D. et al. (Feb. 2005). "Evolution of the Isoprene Biosynthetic Pathway in Kudzu," *Plant Physiology* 137:700-712.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.

Sprenger, G.A. et al. (Nov. 25, 1997). "Identification of a Thiamin-Dependent Synthase in *Escherichia coli* Required for the Formation of the 1-deoxy-$_D$-xylulose 5-phosphate Precursor to Isoprenoids, Thiamin, and Pyridoxol," *PNAS USA* 94(24):12857-12862.

Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *J. Bacteriol.* 184(15):4065-4070.

Tsay, Y.H. et al. (Feb. 1991). "Cloning and Characterization of ERG8, an Essential Gene of *Saccharomyces cerevisiae* That Encodes Phosphomevalonate Kinase," *Mol. Cell. Biol.* 11(2):620-631.

Zepeck, F. et al. (Nov. 11, 2005). "Biosynthesis of Isoprenoids. Purification and Properties of IspG Protein from *Escherichia coli*," *J. Org. Chem.* 70(23):9168-9174.

\* cited by examiner

Figure 3A 1-
tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcgggggctcccttttagggttcc
gatttagtgctttacggcacctcgacccaaaaaacttgattagggtgatggttcacgtagtgggccatcgcccgatagacggttttcgccc
tttgacgttggagtccacgttcttaatagtggactcttgttccaaactggaacaacactcaaccctatctcggtctattcttttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaaccccctatttgtttattttctaaatacattcaaatatgtatccgctcatgaattaattcttagaaaaactcatcg
agcatcaaatgaaactgcaatttattcatatcaggattatcaataccatattttgaaaaagccgtttctgtaatgaaggagaaaactcaccgag
gcagttccataggatggcaagatcctggtatcggtctgcgattccgactcgtccaacatcaatacaacctattaattccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgtttccccgggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccattatacccatataaatcagcatccatgttggaa
tttaatcgcggcctagagcaagacgtttcccgttgaatatggctcataacaccccttgtattactgtttatgtaagcagacagtttattgttcatga
ccaaaatcccttaacgtgagttttcgttccactgagcgtcagaccccgtagaaaagatcaaaggatcttcttgagatccttttttctgcgcgtaa
tctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccaggggggaaacgcctggtatctttatagtcctgtcgggtttcgccacctctgacttgagcgtcgatttttgtgatgctcgtcagggggg
cggagcctatggaaaaacgccagcaacgcggcctttttacggttcctggccttttgctggccttttgctcacatgttcttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtatttttctccttacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactggggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag

Figure 3B ccagccagacgcagacgcgccgagacagaacttaatgggcccgctaacagcgcgatttgctggtgacccaatgcgaccagatgctccac
gcccagtcgcgtaccgtcttcatgggagaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccacttttcccgcgttttcgcagaaacgtggctggcctggttcaccacgcgggaaacggtct
gataagagacaccggcatactctgcgacatcgtataacgttactggtttcacattcaccaccctgaattgactctcttccgggcgctatcatgc
catacccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccggccacggggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
taggggaattgtgagcggataacaattcccctctagaaataattttgtttaactttaagaaggagatatacatatgcgttgtagcgtgtccaccg
aaaatgtgtctttcaccgaaactgaaaccgaagctcgtcgttctgcgaactacgaacctaacagctgggactatgattacctgctgtcctccga
cacggacgagtccatcgaagtatacaaagacaaagcgaaaaagctggaagccgaagttcgtcgcgagattaataacgaaaaagcagaat
ttctgaccctgctggaactgattgacaacgtccagcgcctgggcctgggttaccgtttcgagtctgatatccgtggtgcgctggatcgcttcgt
ttcctccggcggcttcgatgcggtaaccaagacttccctgcacggtacggcactgtctttccgtctgctgcgtcaacacggttttgaggtttctc
aggaagcgttcagcggcttcaaagaccaaaacggcaacttcctggagaacctgaaggaagatatcaaagctatcctgagcctgtacgagg
ccagcttcctggctctggaaggcgaaaacatcctggacgaggcgaaggttttcgcaatctctcatctgaaagaactgtctgaagaaaagatc
ggtaaagagctggcagaacaggtgaaccatgcactggaactgccactgcatcgccgtactcagcgtctggaagcagtatggtctatcgag
gcctaccgtaaaaaggaggacgcgaatcaggttctgctggagctggcaattctggattacaacatgatccagtctgtataccagcgtgatct
gcgtgaaacgtcccgttggtggcgtcgtgtgggtctggcgaccaaactgcactttgctcgtgaccgcctgattgagagcttctactgggccg
tgggtgtagcattcgaaccgcaatactccgactgccgtaactccgtcgcaaaaatgttttctttcgtaaccattatcgacgatatctacgatgtat
acggcaccctggacgaactggagctgtttactgatgcagttgagcgttgggacgtaaacgccatcaacgacctgccggattacatgaaact
gtgctttctggctctgtataacactattaacgaaatcgcctacgacaacctgaaagataaaggtgagaacatcctgccgtatctgaccaaagc
ctgggctgacctgtgcaacgctttcctgcaagaagccaagtggctgtacaacaaatctactccgacctttgacgactacttcggcaacgcatg
gaaatcctcttctggcccgctgcaactggtgttcgcttacttcgctgtcgtgcagaacattaaaaaggaagagatcgaaaacctgcaaaaata
ccatgacaccatctctcgtcctcccatatcttccgtctgtgcaatgacctggctagcgcgtctgcggaaattgcgcgtggtgaaaccgcaaat
agcgtttcttgttacatgcgcactaaaggtatctccgaagaactggctaccgaaagcgtgatgaatctgatcgatgaaacctggaaaaagatg
aacaaggaaaaactgggtggtagcctgttcgcgaaaccgttcgtggaaaccgcgatcaacctggcacgtcaatctcactgcacttatcataa
cggcgacgcgcatacctctccggatgagctgacccgcaaacgcgttctgtctgtaatcactgaaccgattctgccgtttgaacgctaaggat
ccgaattcgagctccgtcgacaagcttgcggccgcactcgagcaccaccaccaccaccactgagatccggctgctaacaaagcccgaaa
ggaagctgagttggctgctgccaccgctgagcaataactagcataaccccttggggcctctaaacgggtcttgaggggttttttgctgaaag
gaggaactatatccggat (SEQ ID NO:1)

Figure 6A 1-
gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagagglatat
attaatgtatcgattaaataaggaggaataaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctgggttaccgtttcgagtctgatatccgtggtgcgctggatcgcttcgtttcctccggcggcttcgatgcggtaaccaagacttcc
ctgcacggtacggcactgtctttccgtctgctgcgtcaacacggttttgaggtttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggttttcgcaatctctcatctgaaagaactgtctgaagaaaagatcggtaaagagctggcagaacaggtgaaccatgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgttttctttcgtaaccattatcgacgatatctacgatgtatacggcaccctggacgaactggagctgtttactgatgc
agttgagcgttgggacgtaaacgccatcaacgacctgccggattacatgaaactgtgctttctggctctgtataacactattaacgaaatcgcc
tacgacaacctgaaagataaaggtgagaacatcctgccgtatctgaccaaagcctgggctgacctgtgcaacgcttctgcaagaagcca
agtggctgtacaacaaatctactccgacctttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttcccatatcttccgtctg
tgcaatgacctggctagcgcgtctgcggaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgttcgcgaaa
ccgttcgtggaaaccgcgatcaacctggcacgtcaatctcactgcacttatcataacggcgacgcgcataccctccgatgagctgaccc
gcaaacgcgttctgtctgtaatcactgaaccgattctgccgtttgaacgctaactgcagctggtaccatatgggaattcgaagctttctagaac
aaaaactcatctcagaagaggatctgaatagcgccgtcgaccatcatcatcatcatcattgagtttaaacggtctccagcttggctgttttggcg
gatgagagaagattttcagcctgatacagattaaatcagaacgcagaagcggtctgataaaacagaatttgcctggcggcagtagcgcggt
ggtcccacctgaccccatgccgaactcagaagtgaaacgccgtagcgccgatggtagtgtggggtctccccatgcgagagtagggaact
gccaggcatcaaataaaacgaaaggctcagtcgaaagactgggcctttcgttttatctgttgtttgtcggtgaacgctctcctgagtaggacaa
atccgccgggagcggatttgaacgttgcgaagcaacggcccggagggtggcgggcaggacgcccgccataaactgccaggcatcaaat
taagcagaaggccatcctgacggatggcctttttgcgtttctacaaactcttttgtttatttttctaaatacatttcaaatatgtatccgctcatgaga
caataaccctgataaatgcttcaataatattgaaaaaggaagagtatgagtattcaacatttccgtgtcgcccttattcccttttttgcggcattttg
ccttcctgtttttgctcacccagaaacgctggtgaaagtaaaagatgctgaagatcagttgggtgcacgagtgggttacatcgaactggatctc
aacagcggtaagatccttgagagttttcgccccgaagaacgttttccaatgatgagcacttttaaagttctgctatgtggcgcggtattatcccg
tgttgacgccgggcaagagcaactcggtcgccgcatacactattctcagaatgacttggttgagtactcaccagtcacagaaaagcatcttac
ggatggcatgacagtaagagaattatgcagtgctgccataaccatgagtgataacactgcggccaacttacttctgacaacgatcggagga
ccgaaggagctaaccgcttttttgcacaacatgggggatcatgtaactcgccttgatcgttgggaaccggagctgaatgaagccataccaaa
cgacgagcgtgacaccacgatgcctgtagcaatggcaacaacgttgcgcaaactattaactggcgaactacttactctagcttcccggcaac
aattaatagactggatgaggcggataaagttgcaggaccacttctgcgctcggcccttccggctggctggtttattgctgataaatctggag
ccggtgagcgtgggtctcgcggtatcattgcagcactggggccagatggtaagccctcccgtatcgtagttatctacacgacggggagtca
ggcaactatggatgaacgaaatagacagatcgctgagataggtgcctcactgattaagcattggtaactgtcagaccaagtttactcatatata
ctttagattgatttaaaacttcatttttaatttaaaaggatctaggtgaagatcctttttgataatctcatgaccaaaatcccttaacgtgagttttcgtt
ccactgagcgtcagaccccgtagaaaagatcaaaggatcttcttgagatccttttttctgcgcgtaatctgctgcttgcaaacaaaaaaacca
ccgctaccagcggtggtttgtttgccggatcaagagctaccaactctttttccgaaggtaactggcttcagcagagcgcagataccaaatact
gtccttctagtgtagccgtagttaggccaccacttcaagaactctgtagcaccgcctacatacctcgctctgctaatcctgttaccagtggctgc

Figure 6B tgccagtggcgataagtcgtgtcttaccgggttggactcaagacgatagttaccggataaggcgcagcggtcgggctgaacgggggttc
gtgcacacagcccagcttggagcgaacgacctacaccgaactgagatacctacagcgtgagctatgagaaagcgccacgcttcccgaag
ggagaaaggcggacaggtatccggtaagcggcagggtcggaacaggagagcgcacgagggagcttccagggggaaacgcctggtat
ctttatagtcctgtcgggtttcgccacctctgacttgagcgtcgattttgtgatgctcgtcagggggcggagcctatggaaaaacgccagca
acgcggccttttacggttcctggcctttgctggccttttgctcacatgttctttcctgcgttatccctgattctgtggataaccgtattaccgcc
ttgagtgagctgataccgctcgccgcagccgaacgaccgagcgcagcgagtcagtgagcgaggaagcggaagagcgcctgatgcggt
attttctccttacgcatctgtgcggtatttcacaccgcatatggtgcactctcagtacaatctgctctgatgccgcatagttaagccagtatacact
ccgctatcgctacgtgactgggtcatggctgcgccccgacacccgccaacacccgctgacgcgccctgacgggcttgtctgctcccggca
tccgcttacagacaagctgtgaccgtctccgggagctgcatgtgtcagaggttttcaccgtcatcaccgaaacgcgcgaggcagcagatca
attcgcgcgcgaaggcgaagcggcatgcatttacgttgacaccatcgaatggtgcaaaacctttcgcggtatggcatgatagcgcccggaa
gagagtcaattcagggtggtgaatgtgaaaccagtaacgttatacgatgtcgcagagtatgccggtgtctcttatcagaccgtttcccgcgtg
gtgaaccaggccagccacgtttctgcgaaaacgcgggaaaaagtggaagcggcgatggcggagctgaattacattcccaaccgcgtggc
acaacaactggcgggcaaacagtcgttgctgattggcgttgccacctccagtctggccctgcacgcgccgtcgcaaattgtcgcggcgatt
aaatctcgcgccgatcaactgggtgccagcgtggtggtgtcgatggtagaacgaagcggcgtcgaagcctgtaaagcggcggtgcacaa
tcttctcgcgcaacgcgtcagtgggctgatcattaactatccgctggatgaccaggatgccattgctgtggaagctgcctgcactaatgttccg
gcgttatttcttgatgtctctgaccagacacccatcaacagtattattttctcccatgaagacggtacgcgactgggcgtggagcatctggtcgc
attgggtcaccagcaaatcgcgctgttagcgggcccattaagttctgtctcggcgcgtctgcgtctggctggctggcataaatatctcactcg
caatcaaattcagccgatagcggaacgggaaggcgactggagtgccatgtccggttttcaacaaaccatgcaaatgctgaatgagggcatc
gttcccactgcgatgctggttgccaacgatcagatggcgctgggcgcaatgcgcgccattaccgagtccgggctgcgcgttggtgcggat
atctcggtagtgggatacgacgataccgaagacagctcatgttatatcccgccgtcaaccaccatcaaacaggattttcgcctgctggggca
aaccagcgtggaccgcttgctgcaactctctcagggccaggcggtgaagggcaatcagctgttgcccgtctcactggtgaaaagaaaaac
caccctggcgcccaatacgcaaaccgcctctccccgcgcgttggccgattcattaatgcagctggcacgacaggtttcccgactggaaagc
gggcagtgagcgcaacgcaattaatgtgagttagcgcgaattgatctg (SEQ ID NO:2)

Figure 9A

1-
gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctgggttaccgtttcgagtctgatatccgtggtgcgctggatcgcttcgtttcctccggcggcttcgatgcggtaaccaagacttcc
ctgcacggtacggcactgtctttccgtctgctgcgtcaacacggttttgaggtttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggttttcgcaatctctcatctgaaagaactgtctgaagaaaagatcggtaaagagctggcagaacaggtgaaccatgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgttttctttcgtaaccattatcgacgatatctacgatgtatacggcaccctggacgaactggagctgtttactgatgc
agttgagcgttgggacgtaaacgccatcaacgacctgccggattacatgaaactgtgctttctggctctgtataacactattaacgaaatcgcc
tacgacaacctgaaagataaaggtgagaacatcctgccgtatctgaccaaagcctgggctgacctgtgcaacgctttcctgcaagaagcca
agtggctgtacaacaaatctactccgacctttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttcccatatcttccgtctg
tgcaatgacctggctagcgcgtctgcggaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgttcgcgaaa
ccgttcgtggaaaccgcgatcaacctggcacgtcaatctcactgcacttatcataacggcgacgcgcatacctctccggatgagctgaccc
gcaaacgcgttctgtctgtaatcactgaaccgattctgccgtttgaacgctaactgcataaaggagggtaaaaaaacatggtatcctgttctgcg
ccgggtaagatttacctgttcggtgaacacgccgtagtttatggcgaaactgcaattgcgtgtgcggtggaactgcgtacccgtgttcgcgcg
gaactcaatgactctatcactattcagagccagatcggccgcaccggtctggatttcgaaaagcacccttatgtgtctgcggtaattgagaaa
atgcgcaaatctattcctattaacggtgttttcttgaccgtcgattccgacatcccggtgggctccggtctgggtagcagcgcagccgttactat
cgcgtctattggtgcgctgaacgagctgttcggctttggcctcagcctgcaagaaatcgctaaactggggccacgaaatcgaaattaaagtac
agggtgccgcgtccccaaccgatacgtatgtttctaccttcggcggcgtggttaccatcccggaacgtcgcaaactgaaaactccggactg
cggcattgtgattggcgataccggcgttttctcctccaccaaagagttagtagctaacgtacgtcagctgcgcgaaagctacccggatttgat
cgaaccgctgatgacctctattggcaaaatctctcgtatcggcgaacaactggttctgtctggcgactacgcatccatcgccgcctgatgaa
cgtcaaccagggtctcctggacgccctgggcgttaacatcttagaactgagccagctgatctattccgctcgtgcggcaggtgcgtttggcg
ctaaaatcacgggcgctggcggcggtggctgtatggttgcgctgaccgctccggaaaaatgcaaccaagtggcagaagcggtagcaggc
gctggcggtaaagtgactatcactaaaccgaccgagcaaggtctgaaagtagattaaagtctagttaaagtttaaacggtctccagcttggct
gttttggcggatgagagaagattttcagcctgatacagattaaatcagaacgcagaagcggtctgataaaacagaatttgctggcggcagt
agcgcggtggtcccacctgaccccatgccgaactcagaagtgaaacgccgtagcgccgatggtagtgtggggtctccccatgcgagagt
agggaactgccaggcatcaaataaaacgaaaggctcagtcgaaagactgggcctttcgttttatctgttgtttgtcggtgaacgctctcctgag
taggacaaatccgccgggagcggatttgaacgttgcgaagcaacggcccggagggtggcgggcaggacgcccgccataaactgccag
gcatcaaattaagcagaaggccatcctgacggatggcctttttgcgtttctacaaactctttttgtttattttctaaatacattcaaatatgtatccg
ctcatgagacaataaccctgataaatgcttcaataatattgaaaaaggaagagtatgagtattcaacatttccgtgtcgcccttattccctttttg
cggcattttgccttcctgttttgctcacccagaaacgctggtgaaagtaaaagatgctgaagatcagttgggtgcacgagtgggttacatcga
actggatctcaacagcggtaagatccttgagagttttcgccccgaagaacgttttccaatgatgagcacttttaaagttctgctatgtggcgcg
gtattatcccgtgttgacgccgggcaagagcaactcggtcgccgcatacactattctcagaatgacttggttgagtactcaccagtcacagaa
aagcatcttacggatggcatgacagtaagagaattatgcagtgctgccataaccatgagtgataacactgcggccaacttacttctgacaacg

Figure 9B atcggaggaccgaaggagctaaccgcttttttgcacaacatgggggatcatgtaactcgccttgatcgttgggaaccggagctgaatgaag
ccataccaaacgacgagcgtgacaccacgatgcctgtagcaatggcaacaacgttgcgcaaactattaactggcgaactacttactctagct
tcccggcaacaattaatagactggatggaggcggataaagttgcaggaccacttctgcgctcggcccttccggctggctggtttattgctgat
aaatctggagccggtgagcgtgggtctcgcggtatcattgcagcactggggccagatggtaagccctcccgtatcgtagttatctacacgac
ggggagtcaggcaactatggatgaacgaaatagacagatcgctgagataggtgcctcactgattaagcattggtaactgtcagaccaagttt
actcatatatactttagattgatttaaaacttcattttaatttaaaaggatctaggtgaagatcctttttgataatctcatgaccaaaatcccttaacgt
gagttttcgttccactgagcgtcagacccgtagaaaagatcaaaggatcttcttgagatcctttttttctgcgcgtaatctgctgcttgcaaaca
aaaaaaccaccgctaccagcggtggtttgtttgccggatcaagagctaccaactctttttccgaaggtaactggcttcagcagagcgcagat
accaaatactgtccttctagtgtagccgtagttaggccaccacttcaagaactctgtagcaccgcctacatacctcgctctgctaatcctgttac
cagtggctgctgccagtggcgataagtcgtgtcttaccgggttggactcaagacgatagttaccggataaggcgcagcggtcgggctgaa
cggggggttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccaggggggaa
acgcctggtatctttatagtcctgtcgggtttcgccacctctgacttgagcgtcgatttttgtgatgctcgtcagggggcggagcctatggaaa
aacgccagcaacgcggcctttttacggttcctggccttttgctggccttttgctcacatgttctttcctgcgttatcccctgattctgtggataacc
gtattaccgcctttgagtgagctgataccgctcgccgcagccgaacgaccgagcgcagcgagtcagtgagcgaggaagcggaagagcg
cctgatgcggtatttctccttacgcatctgtgcggtattcacaccgcatatggtgcactctcagtacaatctgctctgatgccgcatagtaag
ccagtatacactccgctatcgctacgtgactgggtcatggctgcgccccgacaccgccaacacccgctgacgcgccctgacgggcttgt
ctgctcccggcatccgcttacagacaagctgtgaccgtctccgggagctgcatgtgtcagaggttttcaccgtcatccgaaacgcgcga
ggcagcagatcaattcgcgcgcgaaggcgaagcggcatgcatttacgttgacaccatcgaatggtgcaaaacctttcgcggtatggcatga
tagcgcccggaagagagtcaattcagggtggtgaatgtgaaaccagtaacgttatacgatgtcgcagagtatgccggtgtctcttatcagac
cgtttcccgcgtggtgaaccaggccagccacgtttctgcgaaaacgcgggaaaaagtggaagcggcgatggcggagctgaattacattcc
caaccgcgtggcacaacaactggcgggcaaacagtcgttgctgattggcgttgccacctccagtctggccctgcacgcgccgtcgcaaatt
gtcgcggcgattaaatctcgcgccgatcaactgggtgccagcgtggtggtgtcgatggtagaacgaagcggcgtcgaagcctgtaaagcg
gcggtgcacaatcttctcgcgcaacgcgtcagtggctgatcattaactatccgctggatgaccaggatgccattgctgtggaagctgcctg
cactaatgttccggcgttatttcttgatgtctctgaccagacacccatcaacagtattattttctcccatgaagacggtacgcgactgggcgtgg
agcatctggtcgcattgggtcaccagcaaatcgcgctgttagcgggcccattaagttctgtctcggcgcgtctgcgtctggctggctggcata
aatatctcactcgcaatcaaattcagccgatagcggaacggaaggcgactggagtgccatgtccggttttcaacaaaccatgcaaatgctg
aatgagggcatcgttcccactgcgatgctggttgccaacgatcagatggcgctgggcgcaatgcgcgccattaccgagtccgggctgcgc
gttggtgcggatatctcggtagtgggatacgacgataccgaagacagctcatgttatatcccgccgtcaaccaccatcaaacaggattttcgc
ctgctggggcaaaccagcgtggaccgcttgctgcaactctctcagggccaggcggtgaagggcaatcagctgttgcccgtctcactggtg
aaaagaaaaaccaccctggcgcccaatacgcaaaccgcctctccccgcgcgttggccgattcattaatgcagctggcacgacaggttccc
gactggaaagcgggcagtgagcgcaacgcaattaatgtgagttagcgcgaattgatctg (SEQ ID NO:3)

Figure 10B gcggccgcgcccttgacgatgccacatcctgagcaaataattcaaccactaattgtgagcggataacacaaggaggaaacagc
catggtatcctgttctgcgccgggtaagatttacctgttcggtgaacacgccgtagtttatggcgaaactgcaattgcgtgtgcggt
ggaactgcgtacccgtgttcgcgcggaactcaatgactctatcactattcagagccagatcggccgcaccggtctggatttcgaa
aagcacccttatgtgtctgcggtaattgagaaaatgcgcaaatctattcctattaacggtgttttcttgaccgtcgattccgacatccc
ggtgggctccggtctgggtagcagcgcagccgttactatcgcgtctattggtgcgctgaacgagctgttcggctttggcctcagc
ctgcaagaaatcgctaaactgggccacgaaatcgaaattaaagtacagggtgccgcgtccccaaccgatacgtatgtttctacct
tcggcggcgtggttaccatcccggaacgtcgcaaactgaaaactccggactgcggcattgtgattggcgataccggcgttttctc
ctccaccaaagagttagtagctaacgtacgtcagctgcgcgaaagctacccggatttgatcgaaccgctgatgacctctattggc
aaaatctctcgtatcggcgaacaactggttctgtctggcgactacgcatccatcggccgcctgatgaacgtcaaccagggtctcct
ggacgccctgggcgttaacatcttagaactgagccagctgatctattccgctcgtgcggcaggtgcgtttggcgctaaaatcacg
ggcgctggcggcggtggctgtatggttgcgctgaccgctccggaaaaatgcaaccaagtggcagaagcggtagcaggcgct
ggcggtaaagtgactatcactaaaccgaccgagcaaggtctgaaagtagattaagccttgacttaatagctgcttatttcgcccta
tggtacctagtaggaggaaaaaaacatggaaatgcgtcaaccggctgtcgcaggtcaattctacccactgcgttgcgagaacct
ggaaaacgaactgaaacgctgcttcgaaggcctggagatccgcgaacaagaagtgctgggcgcagtctgtccgcacgccggt
tatatgtactctggcaaagttgcggcgcacgtctatgccactctgccggaagctgatacctacgtaatcttcggcccgaaccacac
cggctacggtagccctgtctctgtgagccgtgaaacttggaagaccccgttgggcaatatcgatgttgacctggaactggcgga
cggcttcctgggttccatcgtagatgcggatgaactcggtcacaaatacgaacactctatcgaagttcagctgccgtttctgcaata
ccgttttgaacgcgatttcaaaattctgccaatctgcatgggtatgcaagacgaagaaaccgcggtcgaagtaggtaacctgctg
gcggatctgatcagcgagtccggtaaacgtgctgtgatcatcgcaagctctgatttcacccactatgagacggctgaacgtgcca
aagaaatcgattccgaagttattgattctatcctgaactttgacatctctggcatgtacgatcgcctgtatcgccgtaacgcctctgttt
gcggttacggcccgatcaccgctatgctgacggcaagcaaaaagctgggcggctctcgtgcgactttgctgaaatacgcaaac
agcggtgacgtgtccggtgataaagacgctgtggtgggctacgccgccatcatcgttgagtaagctgattaaaggttgaacagat
aggatttcgtcatggatcctacaaggaggaaaaaaacatgaatgcttctaatgaaccggtgattctgaaactgggtggctctgcta
ttaccgacaaaggtgcctacgaaggcgtagttaaggaagctgatttgctgcgcatcgcacaggaagttagcggtttccgtggca
agatgatcgtggttcatggtgctggtagcttcggccatacgtacgcgaagaaatacggcctggaccgtaccttcgacccagagg
gcgcaattgttactcatgaatctgttaaaaagctcgcctccaaagttgtaggtgctctgaatagcttcggcgtgcgtgctatcgcgg
tgcatcctatggactgcgcagtatgccgtaacggtcgtatcgaaacgatgtatctggactccatcaagttaatgctggaaaaaggt
ctggtgccggttctgcacggcgacgtcgcaatggatattgaactgggcacttgtatcctgtccggtgatcaaatcgttccttacctg
gccaaagaactgggtatctcccgcctcggcctgggcagcgcagaggatggtgtgctggatatggagggcaaacctgtaccgg
aaaatcaccccagaaactttcgaagagttccgccactgcatcggtggttctggttctactgatgtaaccggtggcatgctgggcaaa
gtgctggaacttctggaattgagcaaaaattcttccattactagctacattttcaacgctggtaaagcagacaacatctaccgctttct
gaatggtgagtccatcggcactcgcatcagcccggacaagcgtgtttaagctagttattaacctaaatgctctaaaccagttatga
gctctacaaggaggaaaaaaacatgattaacactaccagccgccgcaaaattgaacacctgaaactctgcgcagaatccccgg
ttgaagcgcgtcaggtatctgccggctttgaagacgttactctgatccaccgcgctttaccggagctgaacatggatgaactgga
cctcagcgttgatttcctgggtaaacgcatcaaagcgccgttcctgattgcgtctatcacgggtggtcacccagataccatcccgg
ttaacgctgcgctggcagctgctgctgaggagctgggtgttggcatcggcgttggctctcagcgcgcggccattgatgatccga
gccaggaagacagcttccgtgtagtgcgtgatgaagccccagatgcgtttgtttatggcaacgtcggcgcagcacagatccgtc
agtatggtgttgaaggtgttgaaaaaactgatcgaaatgattgacgcagatgccttggcaatccacctgaacttctgcaagaagcg
gtccaaccggaaggtgaccgcgacgcgaccggttgcctggacatgattaccgaaatttgctctcagattaaaactccggtaatcg
tgaaagaaaccggtgcaggcattagccgtgaagatgcgattctgttccagaaagctggcgtgagcgcaatcgacgttggcggc
gcgggcggcacctcctgggctggcgtcgaggtctaccgtgctaaagaaagccgtgactctgttagcgagcgtttaggtgagct
gttttgggatttcggcattccgacggtagcttctctgattgaatcccgcgtttccttgccgctgatcgcaaccggcggtatccgtaac
ggtctggacattgctaaaagcattgctctcggcgcaagcgctgccagcgccgctctgccgttcgttggtccgtccctggagggc
aaagaatccgttgtacgtgtgctgagctgcatgctggaagaatttaaagcagcaatgttttgtgcggttgcggcaacatcaaaga

Figure 10C cctgcacaactctccagtagtggtaactggttggacccgcgaatacctggagcagcgcggttttaacgttaaggacctctccctg
ccgggcaacgctctgtaagcttaacgcgtctacaaataaaaaaggcacgtcagatgacgtgccttttttcttgtctaga
(SEQ ID NO:4)

Figure 11B aagggcgagctcaacgatccggctgctaacaaagcccgaaaggaagctgagttggctgctgccaccgctgagcaataactag
cataacccctTggggcctctaaacgggtcttgaggagtttTttgctgaaaggaggaactatatccggatatcccgcaagaggccc
ggcagtaccggcataaccaagcctatgcctacagcatccagggtgacggtgccgaggatgacgatgagcgcattgttagattc
atacacggtgcctgactgcgttagcaatttaactgtgataaactaccgcattaaagcttatcgatgataagctgtcaaacatgagaa
ttaattcttgaagacgaaagggcctcgtgatacgcctatttttataggttaatgtcatgataataatggtttcttagacgtcaggtggca
cttttcggggaaatgtgcgcggaacccctatttgtttattttctaaatacattcaaatatgtatccgctcatgagacaataaccctgat
aaatgcttcaataatattgaaaaaggaagagtatgattgaacaagatggattgcacgcaggttctccggccgcttgggtggagag
gctattcggctatgactgggcacaactgacaatcggctgctctgatgccgccgtgttccggctgtcagcgcaggggcgcccggt
tcttttgtcaagaccgacctgtccggtgccctgaatgaactgcaggacgaggcagcgcggctatcgtggctggccacgacgg
gcgttccttgcgcagctgtgctcgacgttgtcactgaagcgggaagggactggctgctattgggcgaagtgccggggcaggat
ctcctgtcatctcaccttgctcctgccgagaaagtatccatcatggctgatgcaatgcggcggctgcatacgcttgatccggctac
ctgcccattcgaccaccaagcgaaacatcgcatcgagcgggcacgtactcggatgaagccggtcttgtcgatcaggatgatct
ggacgaagagcatcaggggctcgcgccagccgaactgttcgccaggctcaaggcgcgcatgcccgacggcgaggatctcgt
cgtgacacatggcgatgcctgcttgccgaatatcatggtggaaaatggccgcttttctggattcatcgactgtggccggctgggtg
tggcggaccgctatcaggacatagcgttggctacccgtgatattgctgaagagcttggcggcgaatgggctgaccgcttcctcgt
gctttacggtatcgccgctcccgattcgcagcgcatcgccttctatcgccttcttgacgagttcttctgagcgggactctggggttc
gaaatgaccgaccaagcgacgcctaactgtcagaccaagtttactcatatatactttagattgatttaaaacttcattTttaatttaaaa
ggatctaggtgaagatcctttTtgataatctcatgaccaaaatcccttaacgtgagttttcgttccactgagcgtcagaccccgtaga
aaagatcaaaggatcttcttgagatccttttttTctgcgcgtaatctgctgcttgcaaacaaaaaaaccaccgctaccagcggtggtt
tgtttgccggatcaagagctaccaactcttTttccgaaggtaactggcttcagcagagcgcagataccaaatactgtccttctagtgt
agccgtagttaggccaccacttcaagaactctgtagcaccgcctacatacctcgctctgctaatcctgttaccagtggctgctgcc
agtggcgataagtcgtgtcttaccgggttggactcaagacgatagttaccggataaggcgcagcggtcgggctgaacggggg
gttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctgcgtt
atcccctgattctgtggataaccgtattaccgcctttgagtgagctgataccgctcgccgcagccgaacgaccgagcgcagcga
gtcagtgagcgaggaagcggaagagcgcctgatgcggtattttctccttacgcatctgtgcggtatttcacaccgcaatggtgca
ctctcagtacaatctgctctgatgccgcatagttaagccagtatacactccgctatcgctacgtgactgggtcatggctgcgcccc
gacacccgccaacacccgctgacgcgccctgacgggcttgtctgctcccggcatccgcttacagacaagctgtgaccgtctcc
gggagctgcatgtgtcagaggttttcaccgtcatcaccgaaacgcgcgaggcagctgcggtaaagctcatcagcgtggtcgtg
aagcgattcacagatgtctgcctgttcatccgcgtccagctcgttgagtttctccagaagcgttaatgtctggcttctgataaagcgg
gccatgttaagggcggttttttcctgtttggtcactgatgcctccgtgtaaggggggattTctgttcatgggggtaatgataccgatga
aacgagagaggatgctcacgatacgggttactgatgatgaacatgcccggttactggaacgttgtgagggtaaacaactggcg
gtatggatgcggcgggaccagagaaaaatcactcagggtcaatgccagcgcttcgttaatacagatgtaggtgttccacagggt
agccagcagcatcctgcgatgcagatccggaacataatggtgcagggcgctgacttccgcgtttccagactttacgaaacacgg
aaaccgaagaccattcatgttgttgctcaggtcgcagacgttttgcagcagcagtcgcttcacgttcgctcgcgtatcggtgattca
ttctgctaaccagtaaggcaaccccgccagcctagccgggtcctcaacgacaggagcacgatcatgcgcacccgtggccagg
acccaacgctgcccgagatgcgccgcgtgcggctgctggagatggcggacgcgatggatatgttctgccaagggttggtttgc
gcattcacagttctccgcaagaattgattggctccaattcttggagtggtgaatccgttagcgaggtgccgccggcttccattcagg
tcgaggtggcccggctccatgcaccgcgacgcaacgcggggaggcagacaaggtatagggcggcgcctacaatccatgcc
aacccgttccatgtgctcgccgaggcggcataaatcgccgtgacgatcagcggtccaatgatcgaagttaggctggtaagagc
cgcgagcgatccttgaagctgtccctgatggtcgtcatctacctgcctggacagcatggcctgcaacgcgggcatcccgatgcc
gccggaagcgagaagaatcataatggggaaggccatccagcctcgcgtcgcgaacgccagcaagacgtagcccagcgcgt

Figure 11C cggccgccatgccggcgataatggcctgcttctcgccgaaacgtttggtggcgggaccagtgacgaaggcttgagcgagggc
gtgcaagattccgaataccgcaagcgacaggccgatcatcgtcgcgctccagcgaaagcggtcctcgccgaaaatgacccag
agcgctgccggcacctgtcctacgagttgcatgataaagaagacagtcataagtgcggcgacgatagtcatgccccgcgccca
ccggaaggagctgactgggttgaaggctctcaagggcatcggtcgagatcccggtgcctaatgagtgagctaacttacattaatt
gcgttgcgctcactgcccgctttccagtcgggaaacctgtcgtgccagctgcattaatgaatcggccaacgcgcggggagagg
cggtttgcgtattgggcgccagggtggtttttcttttcaccagtgagacggggcaacagctgattgcccttcaccgcctggccctga
gagagttgcagcaagcggtccacgctggtttgccccagcaggcgaaaatcctgtttgatggtggttaacggcgggatataacat
gagctgtcttcggtatcgtcgtatcccactaccgagatatccgcaccaacgcgcagcccggactcggtaatggcgcgcattgcg
cccagcgccatctgatcgttggcaaccagcatcgcagtgggaacgatgcccctcattcagcatttgcatggtttgttgaaaaccgg
acatggcactccagtcgccttcccgttccgctatcggctgaatttgattgcgagtgagatatttatgccagccagccagacgcaga
cgcgccgagacagaacttaatgggcccgctaacagcgcgatttgctggtgacccaatgcgaccagatgctccacgcccagtcg
cgtaccgtcttcatgggagaaaataatactgttgatgggtgtctggtcagagacatcaagaaataacgccggaacattagtgcag
gcagcttccacagcaatggcatcctggtcatccagcggatagttaatgatcagcccactgacgcgttgcgcgagaagattgtgc
accgccgctttacaggcttcgacgccgcttcgttctaccatcgacaccaccacgctggcacccagttgatcggcgcgagatttaa
tcgccgcgacaatttgcgacggcgcgtgcagggccagactggaggtggcaacgccaatcagcaacgactgtttgcccgccag
ttgttgtgccacgcggttgggaatgtaattcagctccgccatcgccgcttccacttttccgcgtttcgcagaaacgtggctggc
ctggttcaccacgcgggaaacggtctgataagagacaccggcatactctgcgacatcgtataacgttactggtttcacattcacca
ccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatg
caaggagatggcgcccaacagtcccccggccacggggcctgccaccatacccacgccgaaacaagcgctcatgagcccga
agtggcgagcccgatcttccccatcggtgatgtcggcgatataggcgccagcaaccgcacctgtggcgccggtgatgccggc
cacgatgcgtccggcgtagaggatcgagatctcgatcccgcgaaattaatacgactcactatagggggaattgtgagcggataac
aattcccctctagaaataattttgtttaactttaagaaggagatatacatatgcggggttctcatcatcatcatcatcatggtatggcta
gcatgactggtggacagcaaatgggtcgggatctgtacgacgatgacgataaggatcatcccttcaccatggtatcctgttctgc
gccgggtaagatttacctgttcggtgaacacgccgtagtttatggcgaaactgcaattgcgtgtgcggtggaactgcgtaccgt
gttcgcgcgcgaactcaatgactctatcactattcagagccagatcggccgcaccggtctggatttcgaaaagcacccttatgtgtc
tgcggtaattgagaaaatgcgcaaatcattcctattaacggtgttttcttgaccgtcgattccgacatcccggtgggctccggtctg
ggtagcagcgcagccgttactatcgcgtctattggtgcgctgaacgagctgttcggctttggcctcagcctgcaagaaatcgcta
aactgggccacgaaatcgaaattaaagtacagggtgccgcgtcccaaccgatacgtatgttctaccttcggcggcgtggttac
catcccggaacgtcgcaaactgaaaactccggactgcggcattgtgattggcgataccggcgttttctcctccaccaaagagtta
gtagctaacgtacgtcagctgcgcgaaagctaccggatttgatcgaaccgctgatgacctctattggcaaaatctctcgtatcgg
cgaacaactggttctgtctggcgactacgcatccatcggccgcctgatgaacgtcaaccagggtctcctggacgccctgggcgt
taacatcttagaactgagccagctgatctattccgctcgtgcggcaggtgcgtttggcgctaaaatcacgggcgctggcggcggt
ggctgtatggttgcgctgaccgctccggaaaaatgcaaccaagtggcagaagcggtagcaggcgctggcggtaaagtgactat
cactaaaccgaccgagcaaggtctgaaagtagattaa
(SEQ ID NO:5)

CDS2: Gentamycin resistance gene; CDS1: *E. coli* replication protein

Figure 13A 1-
ctcgggccgtctcttgggcttgatcggccttcttgcgcatctcacgcgctcctgcggcggcctgtagggcaggctcataccctgccgaacc
gctttgtcagccggtcggccacggcttccggcgtctcaacgcgctttgagattcccagcttttcggccaatccctgcggtgcataggcgcgt
ggctcgaccgcttgcgggctgatggtgacgtggcccactggtggccgctccagggcctcgtagaacgcctgaatgcgcgtgtgacgtgc
cttgctgccctcgatgccccgttgcagccctagatcggccacagcggccgcaaacgtggtctggtcgcgggtcatctgcgctttgttgccga
tgaactccttggccgacagcctgccgtcctgcgtcagcggcaccacgaacgcggtcatgtgcgggctggtttcgtcacggtggatgctggc
cgtcacgatgcgatccgccccgtacttgtccgccagccacttgtgcgccttctcgaagaacgccgcctgctgttcttggctggccgacttcca
ccattccgggctggccgtcatgacgtactcgaccgccaacacagcgtccttgcgccgcttctctggcagcaactcgcgcagtcggcccatc
gcttcatcggtgctgctggccgccagtgctcgttctctggcgtcctgctggcgtcagcgttgggcgtctcgcgctcgcggtaggcgtgctt
gagactggccgccacgttgcccattttcgccagcttcttgcatcgcatgatcgcgtatgccgccatgcctgcccctcccttttggtgtccaacc
ggctcgacgggggcagcgcaaggcggtgcctccggcgggccactcaatgcttgagtatactcactagactttgcttcgcaaagtcgtgac
cgcctacggcggctgcggcgccctacgggcttgctctccgggcttcgccctgcgcggtcgctgcgctcccttgccagcccgtggatatgtg
gacgatggccgcgagcggccaccggctggctcgcttcgctcggcccgtggacaaccctgctggacaagctgatggacaggctgcgcct
gcccacgagcttgaccacagggattgccaccggctacccagccttcgaccacataccaccggctccaactgcgcggcctgcggcctt
gccccatcaatttttttaattttctctggggaaaagcctccggcctgcggcctgcgcgcttcgcttgccggttggacaccaagtggaaggcgg
gtcaaggctcgcgcagcgaccgcgcagcggcttggccttgacgcgcctggaacgacccaagcctatgcgagtgggggcagtcgaagg
cgaagcccgcccgcctgccccccgagcctcacggcggcgagtgcggggggttccaaggggggcagcgccaccttgggcaaggccgaag
gccgcgcagtcgatcaacaagccccggaggggccacttttttgccggagggggagccgcgccgaaggcgtgggggaaccccgcaggg
gtgcccttctttgggcaccaaagaactagatataggggcgaaatgcgaaagacttaaaaatcaacaacttaaaaaaggggggtacgcaacag
ctcattgcggcaccccccgcaatagctcattgcgtaggttaaagaaaatctgtaattgactgccacttttacgcaacgcataattgttgtcgcgc
tgccgaaaagttgcagctgattgcgcatggtgccgcaaccgtgcggcaccctaccgcatggagataagcatggccacgcagtccagaga
aatcggcattcaagccaagaacaagcccggtcactgggtgcaaacggaacgcaaagcgcatgaggcgtgggccgggcttattgcgagg
aaacccacggcggcaatgctgctgcatcacctcgtggcgcagatgggccaccagaacgccgtggtggtcagccagaagacactttccaa
gctcatcggacgttctttgcggacggtccaatacgcagtcaaggacttggtggccgagcgctggatctccgtcgtgaagctcaacggcccc
ggcaccgtgtcggcctacgtggtcaatgaccgcgtggcgtggggccagccccgcgaccagttgcgcctgtcggtgttcagtgccgccgt
ggtggttgatcacgacgaccaggacgaatcgctgttggggcatggcgacctgcgccgcatcccgaccctgtatccgggcgagcagcaac
taccgaccggccccggcgaggagccgcccagccagcccggcattccgggcatggaaccagacctgccagccttgaccgaaacggag
gaatgggaacggcgcgggcagcagcgcctgccgatgcccgatgagccgtgttttctggacgatggcgagccgttggagccgccgacac
gggtcacgctgccgcgccggtagcacttgggttgcgcagcaaccgtaagtgcgctgttccagactatcggctgtagccgcctcgccgcc
ctatacctgtctgcctcccgcgttgcgtcgcggtgcatggagccgggccacctcgacctgaatggaagccggcggcacctcgctaacg
gattcaccgttttttatcaggctctgggaggcagaataaatgatcatatcgtcaattattacctccacggggagagcctgagcaaactggcctca
ggcatttgagaagcacacggtcacactgcttccggtagtcaataaaccggtaaaccagcaatagacataagcggctatttaacgaccctgcc
ctgaaccgacgaccgggtcgaatttgcttcgaatttctgccattcatccgcttattatcacttattcaggcgtagcaccaggcgttaagggca
ccaataactgccttaaaaaaattacgccccgccctgccactcatcgcagtcggcctattggttaaaaaatgagctgattaacaaaaatttaac
gcgaattttaacaaaatattaacgcttacaatttccattcgccattcaggctgcgcaactgttgggaagggcgatcggtgcgggcctcttcgct
attacgccagctggcgaaaggggggatgtgctgcaaggcgattaagttgggtaacgccagggttttcccagtcacgacgttgtaaaacgacg
gccagtgagcgcgcgtaatacgactcactataggggcgaattggagctccaccgcggtggcggccgctctagaactagtggatcccccgg
gctgcatgctcgagcggccgccagtgtgatggatatctgcagaattcgcccttcttgatatcttagtgtgcgttaaccaccacccacattggtc
cctgcccgaccgcatagcggccttttttcatgcagtagccctgctcgccaacaatttcgtataccgagatgtggtgagattttgcccggcgg
caatcagatacttgccgctgtgatcaacattgaagccgcgcggctgggtttccgttggctggaagccttctttactcaacacgctgccatcttc
cgaaacgctgaaaacggtaatcaggctggccggtacggtcgcaggcgtataatggcgaccatccggggtgatgaatatcagccgccc
aacgggtgtcggagaagttttccggcatcatatccagcgtctggacacattcgatattaccgtgcggatcttcagttccagacatccactga
gctgtttaactcattgacgcaatacgcatattgtcgtttggatggaataccatatgacgcgggccggcccccttcaacggtggtcacttccgca
gggtcctgcgccacgagatgaccatcatcgctgaccgtaaacaggcaaatgcgatcctgctttaatgccggaacccacagcgtacggttgt

Figure 13B ccggtgagatattggcggaatggcaaccgtccagccctcgaccacatcgacgacgcccactggcaggccatcttccagacgcgttacgc
tcacgttacccgcattgtaagaacctacaaagacaaactgccctggtgatcggtggaaatatgcgtcggactaccggcagcgcagactc
tgcggcaaaggtcagtgcgccatcgtccggggcgatacgatacgccaggacgcgaaactcagggcgaacaccaacatagagataacgt
ttgtccgggctgaccaccatcggctgcacctgccccggcacatcgacaacctgtgtcagcgtcagtgcgccttcatgattcagattccagac
gtgaatttgctggctctcagggctggcgatatanactgtttgcttcatgaatgctcctttgggttacctccgggaaacgcggttgatttgtttagtg
gttgaattatttgctcaggatgtggcatagtcaagggcgtgacggctcgctaatacaactcactatagggctcgaggaagttcctatactttcta
gagaataggaacttccgcgccgcacacaaaaaccaacacacagatcatgaaaataaagctcttttattggtaccgaattcgccagggagct
ctcagacgtcgcttggtcggtcttattcgaaccccagagtcccgcttacgccccgccctgccactcatcgcagtactgttgtaattcattaagc
attctgccgacatggaagccatcacaaacggcatgatgaacctgaatcgccagcggcatcagcaccttgtcgccttgcgtataatatttgccc
atggtgaaaacgggggcgaagaagttgtccatattggccacgtttaaatcaaaactggtgaaactcacccagggattggctgagacgaaaa
acatattctcaataaacccttagggaaataggccaggttttcaccgtaacacgccacatcttgcgaatatatgtgtagaaactgccggaaatc
gtcgtggtattcactccagagcgatgaaaacgtttcagtttgctcatggaaaacggtgtaacaagggtgaacactatcccatatcaccagctc
accgtctttcattgccatacggaattccggatgagcattcatcaggcgggcaagaatgtgaataaaggccggataaaacttgtgcttattttct
ttacggtctttaaaaaggccgtaatatccagctgaacggtctggttataggtacattgagcaactgactgaaatgcctcaaaatgttctttacgat
gccattgggatatatcaacggtggtatatccagtgattttttctccatggtttagttcctcaccttgtcgtattatactatgccgatatactatgccg
atgattaattgtcaacacgtgctgctgcaggtcgaaaggcccggagatgaggaagaggagaacagcgcggcagacgtgcgcttttgaag
cgtgcagaatgccgggcctccggaggaccttcgggcgcccgccccgccctgagcccgccctgagcccgccccggacccaccccct
cccagcctctgagcccagaaagcgaaggagcaaagctgctattggccgctgccccaaaggcctacccgcttccattgctcagcggtgctg
tccatctgcacgagactagtgagacgtgctacttccatttgtcacgtcctgcacgacgcgagctgcggggcgggggggaacttcctgacta
ggggaggagtggaaggtggcgcgaaggggccaccaaagaacggagccggttggcgcctaccggtggatgtggaatgtgtgcgaggc
cagaggccacttgtgtagcgccaagtgcccagcggggctgctaaagcgcatgctccagactgccttgggaaaagcgcctcccctacccg
gtagaatgaagttcctatactttctagagaataggaacttcgcggccgcccttagtgagggttaattcaactgactgtaacagctaaaattagt
cgcttttggcggtaagggcgaattccagcacactggcggccgttactagtggatccgagctcggtaccaagcttgatgcaggaattcgatat
caagcttatcgataccgtcgacctcgaggggggggcccggtacccagcttttgttccctttagtgagggttaattgcgcgcttggcgtaatcatg
gtcatagctgtttcctgtgtgaaattgttatccgctcacaattccacacaacatacgagccggaagcataaagtgtaaagcctggggtgcctaa
tgagtgagctaactcacattaattgcgttgcgctcactgcccgctttccagtcgggaaacctgtcgtgccagctgcattaatgaatcggccaac
gcgcggggagaggcggtttgcgtattgggcgcatgcataaaaactgttgtaattcattaagcattctgccgacatggaagccatcacaaacg
gcatgatgaacctgaatcgccagcggcatcagcaccttgtcgccttgcgtataatatttgcccatggacgcacaccgtggaaacggatgaa
ggcacgaacccagttgacataagcctgttcggttcgtaaactgtaatgcaagtagcgtatgcgctcacgcaactggtccagaaccttgaccg
aacgcagcggtggtaacggcgcagtggcggttttcatggcttgttatgactgtttttttgtacagtctatgcctcgggcatccaagcagcaagc
gcgttacgccgtgggtcgatgtttgatgttatggagcagcaacgatgttacgcagcagcaacgatgttacgcagcagggcagtcgccctaa
aacaaagttaggtggctcaagtatgggcatcattcgcacatgtaggctcggccctgaccaagtcaaatccatgcgggctgctcttgatctttc
ggtcgtgagttcggagacgtagccacctactcccaacatcagccggactccgattacctcgggaacttgctccgtagtaagacattcatcgc
gcttgctgccttcgaccaagaagcggttgttggcgctctcgcggcttacgttctgcccaggtttgagcagccgcgtagtgagatctatatctat
gatctcgcagtctccggcgagcaccggaggcagggcattgccaccgcgctcatcaatctcctcaagcatgaggccaacgcgcttggtgct
tatgtgatctacgtgcaagcagattacggtgacgatcccgcagtggctctctatacaaagttgggcatacgggaagaagtgatgcactttgat
atcgacccaagtaccgccacctaacaattcgttcaagccgagatcggcttcccgccgcggagttgttcggtaaattgtcacaacgccgcc
aggtggcactttctcggggaaatgtgcgcgcccgcgttcctgctggcgctgggcctgtttctggcgctggacttcccgctgttccgtcagcag
cttttcgcccacggccttgatgatcgcggcggccttggcctgcatatcccgattcaacggccccaggggcgtccagaacgggcttcaggcgc
tcccgaaggt (SEQ ID NO:6).

Figure 19A: Map of plasmid pDW34
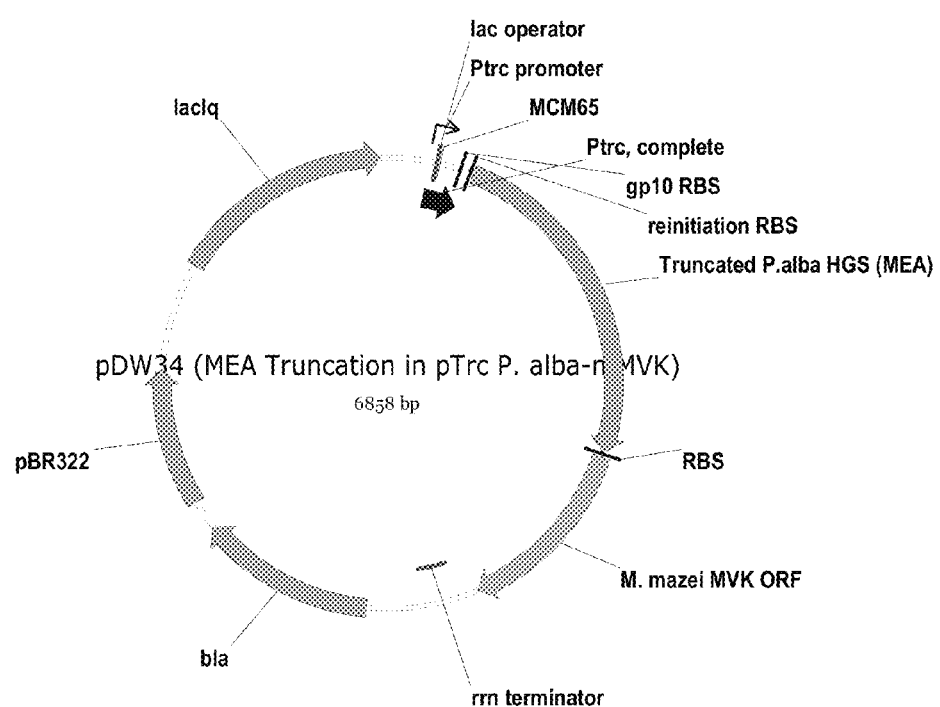

Figure 19B: Sequence of pDW34

5'- gtttgacagcttatcatcgactgcacggtgcaccaatgcttctggcgtcaggcagccatcggaagctgtggtatggctgtgcaggtcgtaaat cactgcataattcgtgtcgctcaaggcgcactcccgttctggataatgttttttgcgccgacatcataacggttctggcaaatattctgaaatgag ctgttgacaattaatcatccggctcgtataatgtgtggaattgtgagcggataacaatttcacacaggaaacagcgccgctgagaaaaagcg aagcggcactgctctttaacaatttatcagacaatctgtgtgggcactcgaccggaattatcgattaactttattattaaaaattaaagagggtatat attaatgtatcgattaaataaggaggaataaaccatggaagctcgtcgttctgcgaactacgaacctaacagctgggactatgattacctgctg tcctccgacacggacgagtccatcgaagtatacaaagacaaagcgaaaaagctggaagccgaagttcgtcgcgagattaataacgaaaaa gcagaattctgaccctgctggaactgattgacaacgtccagcgcctgggcctgggttaccgtttcgagtctgatatccgtggtgcgctggat cgcttcgtttcctccggcggcttcgatgcggtaaccaagacttccctgcacggtacggcactgtctttccgtctgctgcgtcaacacggttttg aggtttctcaggaagcgttcagcggcttcaaagaccaaaacggcaacttcctggagaacctgaaggaagatatcaaagctatcctgagcct gtacgaggccagcttcctggctctggaaggcgaaaacatcctggacgaggcgaaggttttcgcaatctctcatctgaaagaactgtctgaag aaaagatcggtaaagagctggcagaacaggtgaaccatgcactggaactgccactgcatcgccgtactcagcgtctggaagcagtatggt ctatcgaggcctaccgtaaaaaggaggacgcgaatcaggttctgctggagctggcaattctggattacaacatgatccagtctgtataccag cgtgatctgcgtgaaacgtcccgttggtggcgtcgtgtgggtctggcgaccaaactgcactttgctctgtgaccgcctgattgagagcttctac tgggccgtgggtgtagcattcgaaccgcaatactccgactgccgtaactccgtcgcaaaaatgttttctttcgtaaccattatcgacgatatcta cgatgtatacggcaccctggacgaactggagctgtttactgatgcagttgagcgttgggacgtaaacgccatcaacgacctgccggattaca tgaaactgtgctttctggctctgtataacactattaacgaaatcgcctacgacaacctgaaagataaaggtgagaacatcctgccgtatctgac caaagcctgggctgacctgtgcaacgctttcctgcaagaagccaagtggctgtacaacaaatctactccgacctttgacgactacttcggca acgcatggaaatcctcttctggcccgctgcaactggtgttcgcttacttcgctgtcgtgcagaacattaaaaaggaagagatcgaaaacctgc aaaaataccatgacaccatctctcgtccttcccatatcttccgtctgtgcaatgacctggctagcgcgtctgcggaaattgcgcgtggtgaaac cgcaaatagcgtttcttgttacatgcgcactaaaggtatctccgaagaactggctaccgaaagcgtgatgaatctgatcgatgaaacctggaa aaagatgaacaaggaaaaactgggtggtagcctgttcgcgaaaccgttcgtggaaaccgcgatcaacctggcacgtcaatctcactgcact tatcataacggcgacgcgcatacctctccggatgagctgacccgcaaacgcgttctgtctgtaatcactgaaccgattctgccgtttgaacgc taactgcataaaggaggtaaaaaaacatggtatcctgttctgcgccgggtaagatttacctgttcggtgaacacgccgtagtttatggcgaaa ctgcaattgcgtgtgcggtggaactgcgtacccgtgttcgcgcgcggaactcaatgactctatcactattcagagccagatcggccgcaccggt ctggatttcgaaaagcacccttatgtgtctgcggtaattgagaaaatgcgcaaatctattcctattaacggtgttttcttgaccgtcgattccgac atcccggtgggctccggtctgggtagcagcgcagccgttactatcgcgtctattggtgcgctgaacgagctgttcggctttggcctcagcct gcaagaaatcgctaaactgggccacgaaatcgaaattaaagtacaggggtgccgcgtccccaaccgatacgtatgtttctaccttcggcggc gtggttaccatcccggaacgtcgcaaactgaaaactccggactgcggcattgtgattggcgataccggcgtttctcctccaccaaagagtta gtagctaacgtacgtcagctgcgcgaaagctacccggatttgatcgaaccgctgatgacctctattggcaaaatctctcgtatcggcgaaca

Figure 19C: Sequence of pDW34 actggttctgtctggcgactacgcatccatcggccgcctgatgaacgtcaaccagggtctcctggacgccctgggcgttaacatcttagaact
gagccagctgatctattccgctcgtgcggcaggtgcgtttggcgctaaaatcacgggcgctggcggcggtggctgtatggttgcgctgacc
gctccggaaaaatgcaaccaagtggcagaagcggtagcaggcgctggcggtaaagtgactatcactaaaccgaccgagcaaggtctga
aagtagattaaagtctagttaaagtttaaacggtctccagcttggctgttttggcggatgagagaagattttcagcctgatacagattaaatcag
aacgcagaagcggtctgataaaacagaatttgcctggcggcagtagcgcggtggtcccacctgacccatgccgaactcagaagtgaaa
cgccgtagcgccgatggtagtgtggggtctccccatgcgagagtagggaactgccaggcatcaaataaaacgaaaggctcagtcgaaag
actgggcctttcgttttatctgttgtttgtcggtgaacgctctcctgagtaggacaaatccgccgggagcggatttgaacgttgcgaagcaacg
gcccggagggtggcgggcaggacgcccgccataaactgccaggcatcaaattaagcagaaggccatcctgacggatggcctttttgcgtt
tctacaaactcttttgtttatttttctaaatacattcaaatatgtatccgctcatgagacaataaccctgataaatgcttcaataatattgaaaaagga
agagtatgagtattcaacatttccgtgtcgcccttattccctttttgcggcattttgccttcctgttttgctcacccagaaacgctggtgaaagta
aaagatgctgaagatcagttgggtgcacgagtgggttacatcgaactggatctcaacagcggtaagatccttgagagttttcgccccgaaga
acgttttccaatgatgagcacttttaaagttctgctatgtggcgcggtattatcccgtgttgacgccgggcaagagcaactcggtcgccgcata
cactattctcagaatgacttggttgagtactcaccagtcacagaaaagcatcttacggatggcatgacagtaagagaattatgcagtgctgcc
ataaccatgagtgataacactgcggccaacttacttctgacaacgatcggaggaccgaaggagctaaccgcttttttgcacaacatggggga
tcatgtaactcgccttgatcgttgggaaccggagctgaatgaagccataccaaacgacgagcgtgacaccacgatgcctgtagcaatggca
acaacgttgcgcaaactattaactggcgaactacttactctagcttcccggcaacaattaatagactggatggaggcggataaagttgcagg
accacttctgcgctcggcccttccggctggctggtttattgctgataaatctggagccggtgagcgtgggtctcgcggtatcattgcagcact
ggggccagatggtaagccctcccgtatcgtagttatctacacgacggggagtcaggcaactatggatgaacgaaatagacagatcgctga
gataggtgcctcactgattaagcattggtaactgtcagaccaagtttactcatatatactttagattgatttaaaacttcattttaatttaaaaggat
ctaggtgaagatcctttttgataatctcatgaccaaaatcccttaacgtgagttttcgttccactgagcgtcagacccgtagaaaagatcaaag
gatcttcttgagatccttttttctgcgcgtaatctgctgcttgcaaacaaaaaaaccaccgctaccagcggtggtttgtttgccggatcaagagc
taccaactctttttccgaaggtaactggcttcagcagagcgcagataccaaatactgtccttctagtgtagccgtagttaggccaccacttcaa
gaactctgtagcaccgcctacatacctcgctctgctaatcctgttaccagtggctgctgccagtggcgataagtcgtgtcttaccgggttggac
tcaagacgatagttaccggataaggcgcagcggtcgggctgaacggggggttcgtgcacacagcccagcttggagcgaacgacctaca
ccgaactgagatacctacagcgtgagctatgagaaagcgccacgcttcccgaagggagaaaggcggacaggtatccggtaagcggcag
ggtcggaacaggagagcgcacgagggagcttccaggggggaaacgcctggtatctttatagtcctgtcgggtttcgccacctctgacttgag
cgtcgatttttgtgatgctcgtcagggggggcggagcctatggaaaaacgccagcaacgcggccttttacggttcctggccttttgctggcctt
ttgctcacatgttctttcctgcgttatcccctgattctgtggataaccgtattaccgcctttgagtgagctgataccgctcgccgcagccgaacga
ccgagcgcagcgagtcagtgagcgaggaagcggaagagcgcctgatgcggtattttctccttacgcatctgtgcggtatttcacaccgcat
atggtgcactctcagtacaatctgctctgatgccgcatagttaagccagtatacactccgctatcgctacgtgactgggtcatggctgcgcccc

Figure 19D: Sequence of pDW34 gacacccgccaacacccgctgacgcgccctgacgggcttgtctgctcccggcatccgcttacagacaagctgtgaccgtctccgggagct
gcatgtgtcagaggttttcaccgtcatcaccgaaacgcgcgaggcagcagatcaattcgcgcgcgaaggcgaagcggcatgcatttacgtt
gacaccatcgaatggtgcaaaacctttcgcggtatggcatgatagcgcccggaagagagtcaattcagggtggtgaatgtgaaaccagtaa
cgttatacgatgtcgcagagtatgccggtgtctcttatcagaccgtttcccgcgtggtgaaccaggccagccacgtttctgcgaaaacgcgg
gaaaaagtggaagcggcgatggcggagctgaattacattcccaaccgcgtggcacaacaactggcgggcaaacagtcgttgctgattgg
cgttgccacctccagtctggccctgcacgcgccgtcgcaaattgtcgcggcgattaaatctcgcgccgatcaactgggtgccagcgtggtg
gtgtcgatggtagaacgaagcggcgtcgaagcctgtaaagcggcggtgcacaatcttctcgcgcaacgcgtcagtgggctgatcattaact
atccgctggatgaccaggatgccattgctgtggaagctgcctgcactaatgttccggcgttatttcttgatgtctctgaccagacacccatcaa
cagtattattttctcccatgaagacggtacgcgactgggcgtggagcatctggtcgcattgggtcaccagcaaatcgcgctgttagcgggcc
cattaagttctgtctcggcgcgtctgcgtctggctggctggcataaatatctcactcgcaatcaaattcagccgatagcggaacgggaaggc
gactggagtgccatgtccggttttcaacaaaccatgcaaatgctgaatgagggcatcgttcccactgcgatgctggttgccaacgatcagat
ggcgctgggcgcaatgcgcgccattaccgagtccgggctgcgcgttggtgcggatatctcggtagtgggatacgacgataccgaagaca
gctcatgttatatcccgccgtcaaccaccatcaaacaggattttcgcctgctggggcaaaccagcgtggaccgcttgctgcaactctctcagg
gccaggcggtgaagggcaatcagctgttgcccgtctcactggtgaaaagaaaaaccaccctggcgcccaatacgcaaaccgcctctccc
cgcgcgttggccgattcattaatgcagctggcacgacaggtttcccgactggaaagcgggcagtgagcgcaacgcaattaatgtgagttag
cgcgaattgatctg -3' (SEQ ID NO:7)

SEQUENCE LISTING

```
<160> NUMBER OF SEQ ID NOS: 47

<210> SEQ ID NO 1
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 1
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcgggggc tccctttagg     180
gttccgattt agtgctttac ggcacctcga ccccaaaaaa cttgattagg gtgatggttc     240
acgtagtggg ccatcgccct gatagacggt ttttcgccct tgacgttgg agtccacgtt      300 ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcactt     480 tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatatttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgaaatac gcgatcgctg ttaaaaggac      960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca cacttcaag    1680 aactctgtag caccgcctac atacctcgct ctgctaatcc tgttaccagt ggctgctgcc    1740
agtggcgata agtcgtgtct taccgggttg gactcaagac gatagttacc ggataaggcg    1800
```

```
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcaggggg  cggagcctat ggaaaaacgc cagcaacgcg   2100 gccttttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca dacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacgcggga  tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
```

```
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcgttgt agcgtgtcca ccgaaaatgt    5100
gtctttcacc gaaactgaaa ccgaagctcg tcgttctgcg aactacgaac ctaacagctg    5160
ggactatgat tacctgctgt cctccgacac ggacgagtcc atcgaagtat acaaagacaa    5220
agcgaaaaag ctggaagccg aagttcgtcg cgagattaat aacgaaaaag cagaatttct    5280 gacccctgctg gaactgattg acaacgtcca gcgcctgggc ctgggttacc gtttcgagtc    5340
tgatatccgt ggtgcgctgg atcgcttcgt ttcctccggc ggcttcgatg cggtaaccaa    5400
gacttccctg cacggtacgg cactgtcttt ccgtctgctg cgtcaacacg gttttgaggt    5460
ttctcaggaa gcgttcagcg gcttcaaaga ccaaaacggc aacttcctgg agaacctgaa    5520
ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagagctgg cagaacaggt gaaccatgca ctggaactgc cactgcatcg    5700
ccgtactcag cgtctggaag cagtatggtc tatcgaggcc taccgtaaaa aggaggacgc    5760
gaatcaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880 cttttgctcgt gaccgcctga ttgagagctt ctactgggcc gtgggtgtag cattcgaacc    5940
gcaatactcc gactgccgta actccgtcgc aaaaatgttt tctttcgtaa ccattatcga    6000
cgatatctac gatgtatacg gcaccctgga cgaactggac ctgttactg atgcagttga    6060 gcgttgggac gtaaacgcca tcaacgacct gccggattac atgaaactgt gctttctggc    6120
tctgtataac actattaacg aaatcgccta cgacaacctg aaagataaag gtgagaacat    6180
cctgccgtat ctgaccaaag cctgggctga cctgtgcaac gcttcctgc aagaagccaa    6240 gtggctgtac aacaaatcta ctccgaccttt tgacgactac ttcggcaacg catggaaatc    6300
ctcttctggc ccgctgcaac tggtgttcgc ttacttcgct gtcgtgcaga acattaaaaa    6360
ggaagagatc gaaaacctgc aaaaatacca tgacaccatc tctcgtcctt cccatatctt    6420
ccgtctgtgc aatgacctgg ctagcgcgtc tgcggaaatt gcgcgtggtg aaaccgcaaa    6480 tagcgttttct tgttacatgc gcactaaagg tatctccgaa gaactggcta ccgaaagcgt    6540
```

```
gatgaatctg atcgatgaaa cctggaaaaa gatgaacaag gaaaaactgg gtggtagcct    6600
gttcgcgaaa ccgttcgtgg aaaccgcgat caacctggca cgtcaatctc actgcactta    6660
tcataacggc gacgcgcata cctctccgga tgagctgacc cgcaaacgcg ttctgtctgt    6720
aatcactgaa ccgattctgc cgtttgaacg ctaaggatcc gaattcgagc tccgtcgaca    6780
agcttgcggc cgcactcgag caccaccacc accaccactg agatccggct gctaacaaag    6840
cccgaaagga agctgagttg gctgctgcca ccgctgagca ataactagca taaccccttg    6900
gggcctctaa acgggtcttg aggggttttt tgctgaaagg aggaactata tccggat      6957
```

<210> SEQ ID NO 2
<211> LENGTH: 6068
<212> TYPE: DNA
<213> ORGANISM: Artificial Sequence
<220> FEATURE:
<223> OTHER INFORMATION: Synthetic Construct

<400> SEQUENCE: 2

```
gtttgacagc ttatcatcga ctgcacggtg caccaatgct tctggcgtca ggcagccatc      60
ggaagctgtg gtatggctgt gcaggtcgta atcactgcta taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgagatg     420
tagcgtgtcc accgaaaatg tgtctttcac cgaaactgaa accgaagctc gtcgttctgc     480
gaactacgaa cctaacagct gggactatga ttacctgctg tcctccgaca cggacgagtc     540
catcgaagta tacaaagaca agcgaaaaa gctggaagcc gaagttcgtc gcgagattaa     600
taacgaaaaa gcagaatttc tgaccctgct ggaactgatt gacaacgtcc agcgcctggg     660
cctgggttac cgtttcgagt ctgatatccg tggtgcgctg gatcgcttcg tttcctccgg     720
cggcttcgat gcggtaacca agacttccct gcacggtacg gcactgtctt ccgtctgct     780 gcgtcaacac ggttttgagg tttctcagga agcgttcagc ggcttcaaag accaaaacgg     840
caacttcctg gagaacctga aggaagatat caaagctatc ctgagcctgt acgaggccag     900
cttcctggct ctggaaggcg aaaacatcct ggacgaggcg aaggttttcg caatctctca     960
tctgaaagaa ctgtctgaag aaaagatcgg taaagagctg gcagaacagg tgaaccatgc    1020
actggaactg ccactgcatc gccgtactca gcgtctggaa gcagtatggt ctatcgaggc    1080
ctaccgtaaa aaggaggacg cgaatcaggt tctgctggag ctggcaattc tggattacaa    1140
catgatccag tctgtatacc agcgtgatct gcgtgaaacg tcccgttggt ggcgtcgtgt    1200
gggtctggcg accaaactgc actttgctcg tgaccgcctg attgagagct ctactgggc    1260 cgtgggtgta gcattcgaac cgcaatactc cgactgccgt aactccgtcg caaaaatgtt    1320
ttctttcgta accattatcg acgatatcta cgatgtatac ggcaccctgg acgaactgga    1380
gctgttactg gatgcagttg agcgttggga cgtaaacgcc atcaacgacc tgccggatta    1440
catgaaactg tgcttcctgg ctctgtataa cactattaac gaaatcgcct acgacaacct    1500
gaaagataaa ggtgagaaca tcctgccgta tctgaccaaa gcctgggctg acctgtgcaa    1560
cgcttttctg caagaagcca gtggctgta caacaaatct actccgacct ttgacgacta    1620
cttcggcaac gcatggaaat cctcttctgg cccgctgcaa ctggtgttcg cttacttcgc    1680
```

```
tgtcgtgcag aacattaaaa aggaagagat cgaaaacctg caaaaatacc atgacaccat    1740
ctctcgtcct tcccatatct tccgtctgtg caatgacctg gctagcgcgt ctgcggaaat    1800
tgcgcgtggt gaaaccgcaa atagcgtttc ttgttacatg cgcactaaag gtatctccga    1860
agaactggct accgaaagcg tgatgaatct gatcgatgaa acctggaaaa agatgaacaa    1920
ggaaaaactg ggtggtagcc tgttcgcgaa accgttcgtg gaaaccgcga tcaacctggc    1980
acgtcaatct cactgcactt atcataacgg cgacgcgcat acctctccgg atgagctgac    2040
ccgcaaacgc gttctgtctg taatcactga accgattctg ccgtttgaac gctaactgca    2100
gctggtacca tatgggaatt cgaagctttc tagaacaaaa actcatctca gaagaggatc    2160
tgaatagcgc cgtcgaccat catcatcatc atcattgagt ttaaacggtc tccagcttgg    2220
ctgttttggc ggatgagaga agattttcag cctgatacag attaaatcag aacgcagaag    2280
cggtctgata aaacagaatt tgcctggcgg cagtagcgcg gtggtcccac ctgaccccat    2340
gccgaactca gaagtgaaac gccgtagcgc cgatggtagt gtggggtctc cccatgcgag    2400
agtagggaac tgccaggcat caaataaaac gaaaggctca gtcgaaagac tgggcctttc    2460
gttttatctg ttgtttgtcg gtgaacgctc tcctgagtag acaaatccg ccgggagcgg    2520 atttgaacgt tgcgaagcaa cggcccggag ggtggcgggc aggacgcccg ccataaactg    2580
ccaggcatca aattaagcag aaggccatcc tgacggatgg ccttttgcg tttctacaaa    2640 ctctttttgt ttatttttct aaatacattc aaatatgtat ccgctcatga acaataacc    2700 ctgataaatg cttcaataat attgaaaaag gaagagtatg agtattcaac atttccgtgt    2760
cgcccttatt cccttttttg cggcattttg ccttcctgtt tttgctcacc cagaaacgct    2820
ggtgaaagta aaagatgctg aagatcagtt gggtgcacga gtgggttaca tcgaactgga    2880
tctcaacagc ggtaagatcc ttgagagttt tcgccccgaa gaacgttttc caatgatgag    2940
cacttttaaa gttctgctat gtggcgcggt attatcccgt gttgacgccg ggcaagagca    3000
actcggtcgc cgcatacact attctcagaa tgacttggtt gagtactcac cagtcacaga    3060
aaagcatctt acggatggca tgacagtaag agaattatgc agtgctgcca taaccatgag    3120
tgataacact gcggccaact tacttctgac aacgatcgga ggaccgaagg agctaaccgc    3180
ttttttgcac aacatggggg atcatgtaac tcgccttgat cgttgggaac cggagctgaa    3240
tgaagccata ccaaacgacg agcgtgacac cacgatgcct gtagcaatgg caacaacgtt    3300
gcgcaaacta ttaactggcg aactacttac tctagcttcc cggcaacaat taatagactg    3360
gatggaggcg gataaagttg caggaccact tctgcgctcg ccccttccgg ctggctggtt    3420
tattgctgat aaatctggag ccggtgagcg tgggtctcgc ggtatcattg cagcactggg    3480
gccagatggt aagccctccc gtatcgtagt tatctacacg acgggagtc aggcaactat    3540 ggatgaacga aatagacaga tcgctgagat aggtgcctca ctgattaagc attggtaact    3600
gtcagaccaa gttactcat atatacttta gattgattta aaacttcatt tttaatttaa    3660
aaggatctag gtgaagatcc ttttttgataa tctcatgacc aaaatccctt aacgtgagtt    3720
ttcgttccac tgagcgtcag accccgtaga aaagatcaaa ggatcttctt gagatccttt    3780
ttttctgcgc gtaatctgct gcttgcaaac aaaaaaacca ccgctaccag cggtggtttg    3840
tttgccggat caagagctac caactctttt tccgaaggta actggcttca gcagagcgca    3900
gataccaaat actgtccttc tagtgtagcc gtagttaggc caccacttca gaactctgt    3960 agcaccgcct acatacctcg ctctgctaat cctgttacca gtggctgctg ccagtggcga    4020
```

```
taagtcgtgt cttaccgggt tggactcaag acgatagtta ccggataagg cgcagcggtc      4080
gggctgaacg gggggttcgt gcacacagcc cagcttggag cgaacgacct acaccgaact      4140
gagataccta cagcgtgagc tatgagaaag cgccacgctt cccgaaggga gaaaggcgga      4200
caggtatccg gtaagcggca gggtcggaac aggagagcgc acgagggagc ttccaggggg      4260
aaacgcctgg tatctttata gtcctgtcgg gtttcgccac ctctgacttg agcgtcgatt      4320
tttgtgatgc tcgtcagggg gcggagcct atggaaaaac gccagcaacg cggccttttt       4380
acggttcctg gccttttgct ggcctttgc tcacatgttc tttcctgcgt tatcccctga       4440
ttctgtggat aaccgtatta ccgcctttga gtgagctgat accgctcgcc gcagccgaac      4500
gaccgagcgc agcgagtcag tgagcgagga agcggaagag cgcctgatgc ggtatttcct      4560
ccttacgcat ctgtgcggta tttcacaccg catatggtgc actctcagta caatctgctc      4620
tgatgccgca tagttaagcc agtatacact ccgctatcgc tacgtgactg ggtcatggct      4680
gcgccccgac acccgccaac acccgctgac gcgccctgac gggcttgtct gctcccggca      4740
tccgcttaca gacaagctgt gaccgtctcc gggagctgca tgtgtcagag gttttcaccg      4800
tcatcaccga aacgcgcgag gcagcagatc aattcgcgcg cgaaggcgaa gcggcatgca      4860
tttacgttga caccatcgaa tggtgcaaaa cctttcgcgg tatggcatga tagcgcccgg      4920
aagagagtca attcagggtg gtgaatgtga aaccagtaac gttatacgat gtcgcagagt      4980
atgccggtgt ctcttatcag accgtttccc gcgtggtgaa ccaggccagc cacgtttctg      5040
cgaaaacgcg ggaaaaagtg gaagcggcga tggcggagct gaattacatt cccaaccgcg      5100
tggcacaaca actggcgggc aaacagtcgt tgctgattgg cgttgccacc tccagtctgg      5160
ccctgcacgc gccgtcgcaa attgtcgcgg cgattaaatc tcgcgccgat caactgggtg      5220
ccagcgtggt ggtgtcgatg gtagaacgaa gcggcgtcga agcctgtaaa gcggcggtgc      5280
acaatcttct cgcgcaacgc gtcagtgggc tgatcattaa ctatccgctg gatgaccagg      5340
atgccattgc tgtggaagct gcctgcacta atgttccggc gttatttctt gatgtctctg      5400
accagacacc catcaacagt attatttttc tcccatgaaga cggtacgcga ctgggcgtgg      5460
agcatctggt cgcattgggt caccagcaaa tcgcgctgtt agcgggccca ttaagttctg      5520
tctcggcgcg tctgcgtctg gctggctggc ataaatatct cactcgcaat caaattcagc      5580
cgatagcgga acgggaaggc gactggagtg ccatgtccgg ttttcaacaa accatgcaaa      5640
tgctgaatga gggcatcgtt cccactgcga tgctggttgc caacgatcag atggcgctgg      5700
gcgcaatgcg cgccattacc gagtccgggc tgcgcgttgg tgcggatatc tcggtagtgg      5760
gatacgacga taccgaagac agctcatgtt atatcccgcc gtcaaccacc atcaaacagg      5820
attttcgcct gctggggcaa accagcgtgg accgcttgct gcaactctct cagggccagg      5880
cggtgaaggg caatcagctg ttgcccgtct cactggtgaa aagaaaaacc accctggcgc      5940
ccaatacgca aaccgcctct ccccgcgcgt tggccgattc attaatgcag ctggcacgac      6000
aggtttcccg actggaaagc gggcagtgag cgcaacgcaa ttaatgtgag ttagcgcgaa      6060
ttgatctg                                                              6068
```

<210> SEQ ID NO 3
<211> LENGTH: 6906
<212> TYPE: DNA
<213> ORGANISM: Artificial Sequence
<220> FEATURE:
<223> OTHER INFORMATION: Synthetic Construct

<400> SEQUENCE: 3

-continued

```
gtttgacagc ttatcatcga ctgcacggtg caccaatgct tctggcgtca ggcagccatc      60
ggaagctgtg gtatggctgt gcaggtcgta atcactgcaa taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgagatg     420
tagcgtgtcc accgaaaatg tgtctttcac cgaaactgaa accgaagctc gtcgttctgc     480
gaactacgaa cctaacagct gggactatga ttacctgctg tcctccgaca cggacgagtc     540
catcgaagta tacaaagaca aagcgaaaaa gctggaagcc gaagttcgtc gcgagattaa     600
taacgaaaaa gcagaatttc tgaccctgct ggaactgatt gacaacgtcc agcgcctggg     660
cctgggttac cgtttcgagt ctgatatccg tggtgcgctg gatcgcttcg tttcctccgg     720
cggcttcgat gcggtaacca agacttccct gcacggtacg gcactgtctt ccgtctgct      780 gcgtcaacac ggttttgagg tttctcagga agcgttcagc ggcttcaaag accaaaacgg     840
caacttcctg agaaacctga aggaagatat caaagctatc ctgagcctgt acgaggccag     900
cttcctggct ctggaaggcg aaaacatcct ggacgaggcg aaggttttcg caatctctca     960
tctgaaagaa ctgtctgaag aaaagatcgg taaagagctg cagaacagg tgaaccatgc    1020 actggaactg ccactgcatc gccgtactca gcgtctggaa gcagtatggt ctatcgaggc    1080
ctaccgtaaa aaggaggacg cgaatcaggt tctgctggag ctggcaattc tggattacaa    1140
catgatccag tctgtatacc agcgtgatct gcgtgaaacg tcccgttggt ggcgtcgtgt    1200
gggtctggcg accaaactgc actttgctcg tgaccgcctg attgagagct ctactgggc     1260 cgtgggtgta gcattcgaac cgcaatactc cgactgccgt aactccgtcg caaaaatgtt    1320
ttctttcgta accattatcg acgatatcta cgatgtatac ggcaccctgg acgaactgga    1380
gctgtttact gatgcagttg agcgttggga cgtaaacgcc atcaacgacc tgccggatta    1440
catgaaactg tgctttctgg ctctgtataa cactattaac gaaatcgcct acgacaacct    1500
gaaagataaa ggtgagaaca tcctgccgta tctgaccaaa gcctgggctg acctgtgcaa    1560
cgcttttctg caagaagcca agtggctgta caacaaatct actccgacct ttgacgacta    1620
cttcggcaac gcatggaaat cctcttctgg cccgctgcaa ctggtgttcg cttacttcgc    1680
tgtcgtgcag aacattaaaa aggaagagat cgaaaacctg caaaaatacc atgacaccat    1740
ctctcgtcct tcccatatct tccgtctgtg caatgacctg gctagcgcgt ctgcggaaat    1800
tgcgcgtggt gaaaccgcaa atagcgtttc ttgttacatg cgcactaaag gtatctccga    1860
agaactggct accgaaagcg tgatgaatct gatcgatgaa acctggaaaa agatgaacaa    1920
ggaaaaactg ggtggtagcc tgttcgcgaa accgttcgtg gaaaccgcga tcaacctggc    1980
acgtcaatct cactgcactt atcataacgg cgacgcgcat acctctccgg atgagctgac    2040
ccgcaaacgc gttctgtctg taatcactga accgattctg ccgtttgaac gctaactgca    2100
taaaggaggt aaaaaaacat ggtatcctgt tctgcgccgg gtaagattta cctgttcggt    2160
gaacacgccg tagtttatgg cgaaactgca attgcgtgtg cggtggaact gcgtaccgt     2220 gttcgcgcgg aactcaatga ctctatcact attcagagcc gatcggccg caccggtctg    2280 gatttcgaaa agcaccctta tgtgtctgcg gtaattgaga aaatgcgcaa atctattcct    2340
```

```
attaacggtg ttttcttgac cgtcgattcc gacatcccgg tgggctccgg tctgggtagc      2400
agcgcagccg ttactatcgc gtctattggt gcgctgaacg agctgttcgg ctttggcctc      2460
agcctgcaag aaatcgctaa actgggccac gaaatcgaaa ttaaagtaca gggtgccgcg      2520
tccccaaccg atacgtatgt ttctaccttc ggcggcgtgg ttaccatccc ggaacgtcgc      2580
aaactgaaaa ctccggactg cggcattgtg attggcgata ccggcgtttt ctcctccacc      2640
aaagagttag tagctaacgt acgtcagctg cgcgaaagct acccggattt gatcgaaccg      2700
ctgatgacct ctattggcaa aatctctcgt atcggcgaac aactggttct gtctggcgac      2760
tacgcatcca tcggccgcct gatgaacgtc aaccagggtc tcctggacgc cctgggcgtt      2820
aacatcttag aactgagcca gctgatctat tccgctcgtg cggcaggtgc gtttggcgct      2880
aaaatcacgg gcgctggcgg cggtggctgt atggttgcgc tgaccgctcc ggaaaaatgc      2940
aaccaagtgg cagaagcggt agcaggcgct ggcggtaaag tgactatcac taaaccgacc      3000
gagcaaggtc tgaaagtaga ttaaagtcta gttaaagttt aaacggtctc cagcttggct      3060
gttttggcgg atgagagaag atttttcagcc tgatacagat taaatcagaa cgcagaagcg      3120
gtctgataaa acagaatttg cctggcggca gtagcgcggt ggtcccacct gaccccatgc      3180
cgaactcaga agtgaaacgc cgtagcgccg atggtagtgt ggggtctccc catgcgagag      3240
tagggaactg ccaggcatca aataaaacga aaggctcagt cgaaagactg gcctttcgt       3300 tttatctgtt gtttgtcggt gaacgctctc ctgagtagga caaatccgcc gggagcggat      3360
ttgaacgttg cgaagcaacg gcccggaggg tggcgggcag gacgcccgcc ataaactgcc      3420
aggcatcaaa ttaagcagaa ggccatcctg acggatggcc ttttttgcgtt tctacaaact      3480 cttttttgttt attttctaa atacattcaa atatgtatcc gctcatgaga caataaccct      3540
gataaatgct tcaataatat tgaaaaagga agagtatgag tattcaacat ttccgtgtcg      3600
cccttattcc cttttttgcg gcattttgcc ttcctgtttt tgctcaccca gaaacgctgg      3660
tgaaagtaaa agatgctgaa gatcagttgg gtgcacgagt gggttacatc gaactggatc      3720
tcaacagcgg taagatcctt gagagttttc gccccgaaga acgttttcca atgatgagca      3780
cttttaaagt tctgctatgt ggcgcggtat tatcccgtgt tgacgccggg caagagcaac      3840
tcggtcgccg catacactat tctcagaatg acttggttga gtactcacca gtcacagaaa      3900
agcatcttac ggatggcatg acagtaagag aattatgcag tgctgccata accatgagtg      3960
ataacactgc ggccaactta cttctgacaa cgatcggagg accgaaggag ctaaccgctt      4020
ttttgcacaa catgggggat catgtaactc gccttgatcg ttgggaaccg gagctgaatg      4080
aagccatacc aaacgacgag cgtgacacca cgatgcctgt agcaatggca acaacgttgc      4140
gcaaactatt aactggcgaa ctacttactc tagcttcccg gcaacaatta atagactgga      4200
tggaggcgga taaagttgca ggaccacttc tgcgctcggc ccttccggct ggctggttta      4260
ttgctgataa atctggagcc ggtgagcgtg ggtctcgcgg tatcattgca gcactggggc      4320
cagatggtaa gccctcccgt atcgtagtta tctacacgac ggggagtcag gcaactatgg      4380
atgaacgaaa tagacagatc gctgagatag gtgcctcact gattaagcat tggtaactgt      4440
cagaccaagt ttactcatat atactttaga ttgatttaaa acttcatttt taatttaaaa      4500
ggatctaggt gaagatcctt tttgataatc tcatgaccaa aatcccttaa cgtgagtttt      4560
cgttccactg agcgtcagac cccgtagaaa agatcaaagg atcttcttga gatcctttttt   4620 ttctgcgcgt aatctgctgc ttgcaaacaa aaaaaccacc gctaccagcg gtggtttgtt      4680
tgccggatca agagctacca actctttttc cgaaggtaac tggcttcagc agagcgcaga      4740
```

```
taccaaatac tgtccttcta gtgtagccgt agttaggcca ccacttcaag aactctgtag   4800
caccgcctac atacctcgct ctgctaatcc tgttaccagt ggctgctgcc agtggcgata   4860
agtcgtgtct taccgggttg gactcaagac gatagttacc ggataaggcg cagcggtcgg   4920
gctgaacggg gggttcgtgc acacagccca gcttggagcg aacgacctac accgaactga   4980
gatacctaca gcgtgagcta tgagaaagcg ccacgcttcc cgaagggaga aaggcggaca   5040
ggtatccggt aagcggcagg gtcggaacag gagagcgcac gagggagctt ccagggggaa   5100
acgcctggta tctttatagt cctgtcgggt ttcgccacct ctgacttgag cgtcgatttt   5160
tgtgatgctc gtcagggggg cggagcctat ggaaaaacgc cagcaacgcg gcctttttac   5220
ggttcctggc cttttgctgg ccttttgctc acatgttctt tcctgcgtta tcccctgatt   5280
ctgtggataa ccgtattacc gcctttgagt gagctgatac cgctcgccgc agccgaacga   5340
ccgagcgcag cgagtcagtg agcgaggaag cggaagagcg cctgatgcgg tattttctcc   5400
ttacgcatct gtgcggtatt tcacaccgca tatggtgcac tctcagtaca atctgctctg   5460
atgccgcata gttaagccag tatacactcc gctatcgcta cgtgactggg tcatggctgc   5520
gccccgacac ccgccaacac ccgctgacgc gccctgacgg gcttgtctgc tcccggcatc   5580
cgcttacaga caagctgtga ccgtctccgg gagctgcatg tgtcagaggt tttcaccgtc   5640
atcaccgaaa cgcgcgaggc agcagatcaa ttcgcgcgcg aaggcgaagc ggcatgcatt   5700
tacgttgaca ccatcgaatg gtgcaaaacc tttcgcggta tggcatgata gcgcccggaa   5760
gagagtcaat tcagggtggt gaatgtgaaa ccagtaacgt tatacgatgt cgcagagtat   5820
gccggtgtct cttatcagac cgtttcccgc gtggtgaacc aggccagcca cgtttctgcg   5880
aaaacgcggg aaaaagtgga agcggcgatg gcggagctga attacattcc caaccgcgtg   5940
gcacaacaac tggcgggcaa acagtcgttg ctgattggcg ttgccacctc cagtctggcc   6000
ctgcacgcgc cgtcgcaaat tgtcgcggcg attaaatctc gcgccgatca actgggtgcc   6060
agcgtggtgg tgtcgatggt agaacgaagc ggcgtcgaag cctgtaaagc ggcggtgcac   6120
aatcttctcg cgcaacgcgt cagtgggctg atcattaact atccgctgga tgaccaggat   6180
gccattgctg tggaagctgc ctgcactaat gttccggcgt tatttcttga tgtctctgac   6240
cagacaccca tcaacagtat tattttctcc catgaagacg gtacgcgact gggcgtggag   6300
catctggtcg cattgggtca ccagcaaatc gcgctgttag cgggcccatt aagttctgtc   6360
tcggcgcgtc tgcgtctggc tggctggcat aaatatctca ctcgcaatca aattcagccg   6420
atagcggaac gggaaggcga ctggagtgcc atgtccggtt ttcaacaaac catgcaaatg   6480
ctgaatgagg gcatcgttcc cactgcgatg ctggttgcca acgatcagat ggcgctgggc   6540
gcaatgcgcg ccattaccga gtccgggctg cgcgttggtg cggatatctc ggtagtggga   6600
tacgacgata ccgaagacag ctcatgttat atcccgccgt caaccaccat caaacaggat   6660
tttcgcctgc tggggcaaac cagcgtggac cgcttgctgc aactctctca gggccaggcg   6720
gtgaagggca atcagctgtt gcccgtctca ctggtgaaaa gaaaaaccac cctggcgccc   6780
aatacgcaaa ccgcctctcc ccgcgcgttg gccgattcat taatgcagct ggcacgacag   6840
gtttcccgac tggaaagcgg gcagtgagcg caacgcaatt aatgtgagtt agcgcgaatt   6900
gatctg                                                              6906
```

<210> SEQ ID NO 4
<211> LENGTH: 3913
<212> TYPE: DNA

<213> ORGANISM: Artificial Sequence
<220> FEATURE:
<223> OTHER INFORMATION: Synthetic Construct

<400> SEQUENCE: 4

```
gcggccgcgc ccttgacgat gccacatcct gagcaaataa ttcaaccact aattgtgagc      60
ggataacaca aggaggaaac agccatggta tcctgttctg cgccgggtaa gatttacctg     120
ttcggtgaac acgccgtagt ttatggcgaa actgcaattg cgtgtgcggt ggaactgcgt     180
acccgtgttc gcgcggaact caatgactct atcactattc agagccagat cggccgcacc     240
ggtctggatt tcgaaaagca cccttatgtg tctgcggtaa ttgagaaaat gcgcaaatct     300
attcctatta acggtgtttt cttgaccgtc gattccgaca tcccggtggg ctccggtctg     360
ggtagcagcg cagccgttac tatcgcgtct attggtgcgc tgaacgagct gttcggcttt     420
ggcctcagcc tgcaagaaat cgctaaactg ggccacgaaa tcgaaattaa agtacagggt     480
gccgcgtccc caaccgatac gtatgttcct accttcggcg cgtggttac catcccggaa     540
cgtcgcaaac tgaaaactcc ggactgcggc attgtgattg cgataccgg cgttttctcc     600
tccaccaaag agttagtagc taacgtacgt cagctgcgcg aaagctaccc ggatttgatc     660
gaaccgctga tgacctctat tggcaaaatc tctcgtatcg cgaacaact ggttctgtct     720
ggcgactacg catccatcgg ccgcctgatg aacgtcaacc agggtctcct ggacgccctg     780
ggcgttaaca tcttagaact gagccagctg atctattccg ctcgtgcggc aggtgcgttt     840
ggcgctaaaa tcacgggcgc tggcggcggt ggctgtatgg ttgcgctgac cgctccggaa     900
aaatgcaacc aagtggcaga agcggtagca ggcgctggcg gtaaagtgac tatcactaaa     960
ccgaccgagc aaggtctgaa agtagattaa gccttgactt aatagctgct tatttcgccc    1020
ttatggtacc tagtaggagg aaaaaaacat ggaaatgcgt caaccggctg tcgcaggtca    1080
attctaccca ctgcgttgcg agaacctgga aaacgaactg aaacgctgct cgaaggcct     1140
ggagatccgc gaacaagaag tgctgggcgc agtctgtccg cacgccggtt atatgtactc    1200
tggcaaagtt gcggcgcacg tctatgccac tctgccggaa gctgatacct acgtaatctt    1260
cggcccgaac cacaccggct acggtagccc tgtctctgtg agccgtgaaa cttggaagac    1320
cccgttgggc aatatcgatg ttgacctgga actggcggac ggcttcctgg ttccatcgt    1380
agatgcggat gaactcggtc acaaatacga acactctatc gaagttcagc tgccgttctc   1440
gcaataccgt tttgaacgcg atttcaaaat tctgccaatc tgcatgggta tgcaagacga   1500
agaaaccgcg gtcgaagtag gtaacctgct ggcggatctg atcagcgagt ccggtaaacg   1560
tgctgtgatc atcgcaagct ctgatttcac ccactatgag acggctgaac gtgccaaaga   1620
aatcgattcc gaagttattg attctatcct gaactttgac atctctggca tgtacgatcg   1680
cctgtatcgc cgtaacgcct ctgtttgcgg ttacggcccg atcaccgcta tgctgacggc   1740
aagcaaaaag ctgggcggct ctcgtgcgac tttgctgaaa tacgcaaaca gcggtgacgt   1800
gtccggtgat aaagacgctg tggtgggcta cgccgccatc atcgttgagt aagctgatta   1860
aaggttgaac agataggatt tcgtcatgga tcctacaagg aggaaaaaaa catgaatgct   1920
tctaatgaac cggtgattct gaaactgggt ggctctgcta ttaccgacaa aggtgcctac    1980
gaaggcgtag ttaaggaagc tgatttgctg cgcatcgcac aggaagttag cggtttccgt    2040
ggcaagatga tcgtggttca tggtgctggt agcttcggcc atacgtacgc gaagaaatac    2100
ggcctggacc gtaccttcga cccagagggc gcaattgtta ctcatgaatc tgttaaaaag    2160
ctcgcctcca aagttgtagg tgctctgaat agcttcggcg tgcgtgctat gcggtgcat    2220
```

```
cctatggact gcgcagtatg ccgtaacggt cgtatcgaaa cgatgtatct ggactccatc    2280
aagttaatgc tggaaaaagg tctggtgccg gttctgcacg gcgacgtcgc aatggatatt    2340
gaactgggca cttgtatcct gtccggtgat caaatcgttc cttacctggc caagaactg     2400 ggtatctccc gcctcggcct gggcagcgca gaggatggtg tgctggatat ggagggcaaa    2460
cctgtaccgg aaatcacccc agaaactttc gaagagttcc gccactgcat cggtggttct    2520
ggttctactg atgtaaccgg tggcatgctg ggcaaagtgc tggaacttct ggaattgagc    2580
aaaaattctt ccattactag ctacattttc aacgctggta aagcagacaa catctaccgc    2640
tttctgaatg gtgagtccat cggcactcgc atcagcccgg acaagcgtgt ttaagctagt    2700
tattaaccta aatgctctaa accagttatg agctctacaa ggaggaaaaa aacatgatta    2760
acactaccag ccgccgcaaa attgaacacc tgaaactctg cgcagaatcc ccggttgaag    2820
cgcgtcaggt atctgccggc tttgaagacg ttactctgat ccaccgcgct ttaccggagc    2880
tgaacatgga tgaactggac ctcagcgttg atttcctggg taaacgcatc aaagcgccgt    2940
tcctgattgc gtctatcacg ggtggtcacc cagataccat cccggttaac gctgcgctgg    3000
cagctgctgc tgaggagctg ggtgttggca tcggcgttgg ctctcagcgc gcggccattg    3060
atgatccgag ccaggaagac agcttccgtg tagtgcgtga tgaagcccca gatgcgtttg    3120
tttatggcaa cgtcggcgca gcacagatcc gtcagtatgg tgttgaaggt gttgaaaaac    3180
tgatcgaaat gattgacgca gatgccttgg caatccacct gaactttctg caagaagcgg    3240
tccaaccgga aggtgaccgc gacgcgaccg gttgcctgga catgattacc gaaatttgct    3300
ctcagattaa aactccggta atcgtgaaag aaaccggtgc aggcattagc cgtgaagatg    3360
cgattctgtt ccagaaagct ggcgtgagcg caatcgacgt tggcggcgcg ggcggcacct    3420
cctgggctgg cgtcgaggtc taccgtgcta agaaagccg tgactctgtt agcgagcgtt    3480
taggtgagct gttttgggat tcggcattc cgacggtagc ttctctgatt gaatcccgcg    3540
tttccttgcc gctgatcgca accggcggta tccgtaacgg tctggacatt gctaaaagca    3600
ttgctctcgg cgcaagcgct gccagcgccg ctctgccgtt cgttggtccg tccctggagg    3660
gcaaagaatc cgttgtacgt gtgctgagct gcatgctgga agaatttaaa gcagcaatgt    3720
ttttgtgcgg ttgcggcaac atcaaagacc tgcacaactc tccagtagtg gtaactggtt    3780
ggacccgcga atacctggag cagcgcggtt ttaacgttaa ggacctctcc ctgccgggca    3840
acgctctgta agcttcaacg cgtctacaaa taaaaaaggc acgtcagatg acgtgccttt    3900
tttcttgtct aga                                                       3913
```

<210> SEQ ID NO 5
<211> LENGTH: 6647
<212> TYPE: DNA
<213> ORGANISM: Artificial Sequence
<220> FEATURE:
<223> OTHER INFORMATION: Synthetic Construct

<400> SEQUENCE: 5

```
aagggcgagc tcaacgatcc ggctgctaac aaagcccgaa aggaagctga gttggctgct      60
gccaccgctg agcaataact agcataaccc cttggggcct ctaaacgggt cttgaggagt     120 ttttgctga aaggaggaac tatatccgga tatcccgcaa gaggcccggc agtaccggca     180
taaccaagcc tatgcctaca gcatccaggg tgacggtgcc gaggatgacg atgagcgcat     240
tgttagattt catcacacggt gcctgactgc gttagcaatt taactgtgat aaactaccgc     300
```

| | |
|---|---|
| attaaagctt atcgatgata agctgtcaaa catgagaatt aattcttgaa gacgaaaggg | 360 |
| cctcgtgata cgcctatttt tataggttaa tgtcatgata ataatggttt cttagacgtc | 420 |
| aggtggcact tttcggggaa atgtgcgcgg aaccccctatt tgtttatttt tctaaataca | 480 |
| ttcaaatatg tatccgctca tgagacaata accctgataa atgcttcaat aatattgaaa | 540 |
| aaggaagagt atgattgaac aagatggatt gcacgcaggt tctccggccg cttgggtgga | 600 |
| gaggctattc ggctatgact gggcacaact gacaatcggc tgctctgatg ccgccgtgtt | 660 |
| ccggctgtca gcgcaggggc gcccggttct ttttgtcaag accgacctgt ccggtgccct | 720 |
| gaatgaactg caggacgagg cagcgcggct atcgtggctg gccacgacgg gcgttccttg | 780 |
| cgcagctgtg ctcgacgttg tcactgaagc gggaagggac tggctgctat tgggcgaagt | 840 |
| gccggggcag gatctcctgt catctcacct tgctcctgcc gagaaagtat ccatcatggc | 900 |
| tgatgcaatg cggcggctgc atacgcttga tccggctacc tgcccattcg accaccaagc | 960 |
| gaaacatcgc atcgagcggg cacgtactcg gatggaagcc ggtcttgtcg atcaggatga | 1020 |
| tctggacgaa gagcatcagg ggctcgcgcc agccgaactg ttcgccaggc tcaaggcgcg | 1080 |
| catgcccgac ggcgaggatc tcgtcgtgac acatggcgat gcctgcttgc cgaatatcat | 1140 |
| ggtggaaaat ggccgctttt ctggattcat cgactgtggc cggctgggtg tggcggaccg | 1200 |
| ctatcaggac atagcgttgg ctacccgtga tattgctgaa gagcttggcg gcgaatgggc | 1260 |
| tgaccgcttc ctcgtgcttt acggtatcgc cgctcccgat tcgcagcgca tcgccttcta | 1320 |
| tcgccttctt gacgagttct tctgagcggg actctggggt tcgaaatgac cgaccaagcg | 1380 |
| acgcctaact gtcagaccaa gtttactcat atatacttta gattgattta aaacttcatt | 1440 |
| tttaatttaa aaggatctag gtgaagatcc ttttttgataa tctcatgacc aaaatccctt | 1500 |
| aacgtgagtt ttcgttccac tgagcgtcag accccgtaga aagatcaaa ggatcttctt | 1560 |
| gagatccttt ttttctgcgc gtaatctgct gcttgcaaac aaaaaaacca ccgctaccag | 1620 |
| cggtggtttg tttgccggat caagagctac caactctttt tccgaaggta actggcttca | 1680 |
| gcagagcgca gataccaaat actgtccttc tagtgtagcc gtagttaggc caccacttca | 1740 |
| agaactctgt agcaccgcct acatacctcg ctctgctaat cctgttacca gtggctgctg | 1800 |
| ccagtggcga taagtcgtgt cttaccgggt tggactcaag acgatagtta ccggataagg | 1860 |
| cgcagcggtc gggctgaacg gggggttcgt gcacacagcc cagcttggag cgaacgacct | 1920 |
| acaccgaact gagatacccta cagcgtgagc tatgagaaag cgccacgctt cccgaaggga | 1980 |
| gaaaggcgga caggtatccg gtaagcggca gggtcggaac aggagagcgc acgagggagc | 2040 |
| ttccaggggg aaacgcctgg tatctttata gtcctgtcgg gtttcgccac ctctgacttg | 2100 |
| agcgtcgatt tttgtgatgc tcgtcagggg gcggagcct atggaaaaac gccagcaacg | 2160 |
| cggccttttt acggttcctg gccttttgct ggccttttgc tcacatgttc tttcctgcgt | 2220 |
| tatcccctga ttctgtggat aaccgtatta ccgcctttga gtgagctgat accgctcgcc | 2280 |
| gcagccgaac gaccgagcgc agcgagtcag tgagcgagga agcggaagag cgcctgatgc | 2340 |
| ggtattttct ccttacgcat ctgtgcggta tttcacaccg caatggtgca ctctcagtac | 2400 |
| aatctgctct gatgccgcat agttaagcca gtatacactc cgctatcgct acgtgactgg | 2460 |
| gtcatggctg cgccccgaca cccgccaaca cccgctgacg cgccctgacg ggcttgtctg | 2520 |
| ctcccggcat ccgcttacag acaagctgtg accgtctccg ggagctgcat gtgtcagagg | 2580 |
| ttttcaccgt catcaccgaa acgcgcgagg cagctgcggt aaagctcatc agcgtggtcg | 2640 |
| tgaagcgatt cacagatgtc tgcctgttca tccgcgtcca gctcgttgag tttctccaga | 2700 |

```
agcgttaatg tctggcttct gataaagcgg gccatgttaa gggcggtttt ttcctgtttg    2760
gtcactgatg cctccgtgta agggggattt ctgttcatgg gggtaatgat accgatgaaa    2820
cgagagagga tgctcacgat acgggttact gatgatgaac atgcccggtt actggaacgt    2880
tgtgagggta aacaactggc ggtatggatg cggcgggacc agagaaaaat cactcagggt    2940
caatgccagc gcttcgttaa tacagatgta ggtgttccac agggtagcca gcagcatcct    3000
gcgatgcaga tccggaacat aatggtgcag gcgctgact  tccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa    3480 tccatgccaa cccgttccat gtgctcgccg aggcggcata atcgccgtg  acgatcagcg    3540 gtccaatgat cgaagttagg ctggtaagag ccgcgagcga tccttgaagc tgtccctgat    3600
ggtcgtcatc tacctgcctg acagcatgg  cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg  cagggccaga ctggaggtgg caacgccaat cagcaacgac    4980
tgtttgcccg ccagttgttg tgccacgcgg ttgggaatgt aattcagctc cgccatcgcc    5040
```

```
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accataccca cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta ggggaattgt gagcggat     5580 aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catggtatcc tgttctgcgc    5760
cgggtaagat ttacctgttc ggtgaacacg ccgtagttta tggcgaaact gcaattgcgt    5820
gtgcggtgga actgcgtacc cgtgttcgcg cggaactcaa tgactctatc actattcaga    5880
gccagatcgg ccgcaccggt ctggatttcg aaaagcaccc ttatgtgtct gcggtaattg    5940
agaaaatgcg caaatctatt cctattaacg gtgttttctt gaccgtcgat tccgacatcc    6000
cggtgggctc cggtctgggt agcagcgcag ccgttactat cgcgtctatt ggtgcgctga    6060
acgagctgtt cggctttggc ctcagcctgc aagaaatcgc taaactgggc cacgaaatcg    6120
aaattaaagt acagggtgcc gcgtccccaa ccgatacgta tgtttctacc ttcggcggcg    6180
tggttaccat cccggaacgt cgcaaactga aactccggga ctgcggcatt gtgattggcg    6240
ataccggcgt tttctcctcc accaaagagt tagtagctaa cgtacgtcag ctgcgcgaaa    6300
gctacccgga tttgatcgaa ccgctgatga cctctattgg caaaatctct cgtatcggcg    6360
aacaactggt tctgtctggc gactacgcat ccatcggccg cctgatgaac gtcaaccagg    6420
gtctcctgga cgccctgggc gttaacatct agaactgag ccagctgatc tattccgctc    6480
gtgcggcagg tgcgtttggc gctaaaatca cgggcgctgg cggcggtggc tgtatggttg    6540
cgctgaccgc tccggaaaaa tgcaaccaag tggcagaagc ggtagcaggc gctggcggta    6600
aagtgactat cactaaaccg accgagcaag gtctgaaagt agattaa                 6647
```

<210> SEQ ID NO 6
<211> LENGTH: 7519
<212> TYPE: DNA
<213> ORGANISM: Artificial Sequence
<220> FEATURE:
<223> OTHER INFORMATION: Synthetic Construct

<400> SEQUENCE: 6

```
ctcgggccgt ctcttgggct tgatcggcct tcttgcgcat tcacgcgct cctgcggcgg      60 cctgtagggc aggctcatac ccctgccgaa ccgcttttgt cagccggtcg gccacggctt    120
ccggcgtctc aacgcgcttt gagattccca gcttttcggc caatccctgc ggtgcatagg    180
cgcgtggctc gaccgcttgc gggctgatgg tgacgtggcc cactggtggc cgctccaggg    240
cctcgtagaa cgcctgaatg cgcgtgtgac gtgccttgct gccctcgatg cccgttgca    300 gccctagatc ggccacagcg gccgcaaacg tggtctggtc gcgggtcatc tgcgctttgt    360
tgccgatgaa ctccttggcc gacagcctgc cgtcctgcgt cagcggcacc acgaacgcgg    420
tcatgtgcgg gctggtttcg tcacggtgga tgctggccgt cacgatgcga tccgccccgt    480
```

```
acttgtccgc cagccacttg tgcgccttct cgaagaacgc cgcctgctgt tcttggctgg      540
ccgacttcca ccattccggg ctggccgtca tgacgtactc gaccgccaac acagcgtcct      600
tgcgccgctt ctctggcagc aactcgcgca gtcggcccat cgcttcatcg gtgctgctgg      660
ccgcccagtg ctcgttctct ggcgtcctgc tggcgtcagc gttgggcgtc tcgcgctcgc      720
ggtaggcgtg cttgagactg gccgccacgt tgcccatttt cgccagcttc ttgcatcgca      780
tgatcgcgta tgccgccatg cctgcccctc ccttttggtg tccaaccggc tcgacggggg      840
cagcgcaagg cggtgcctcc ggcgggccac tcaatgcttg agtatactca ctagactttg      900
cttcgcaaag tcgtgaccgc ctacggcggc tgcggcgccc tacgggcttg ctctccgggc      960
ttcgccctgc gcggtcgctg cgctcccttg ccagcccgtg gatatgtgga cgatggccgc     1020
gagcggccac cggctggctc gcttcgctcg gccgtggac aaccctgctg gacaagctga     1080
tggacaggct gcgcctgccc acgagcttga ccacagggat gcccaccgg ctacccagcc     1140
ttcgaccaca tacccaccgg ctccaactgc gcggcctgcg gccttgcccc atcaattttt     1200
ttaattttct ctggggaaaa gcctccggcc tgcggcctgc gcgcttcgct tgccggttgg     1260
acaccaagtg gaaggcgggt caaggctcgc gcagcgaccg cgcagcggct tggccttgac     1320
gcgcctggaa cgacccaagc ctatgcgagt gggggcagtc gaaggcgaag cccgcccgcc     1380
tgccccccga gcctcacggc ggcgagtgcg ggggttccaa gggggcagcg ccaccttggg     1440
caaggccgaa ggccgcgcag tcgatcaaca agccccggag gggccacttt tgccggagg     1500
gggagccgcg ccgaaggcgt ggggg aaccc cgcagggtg cccttctttg ggcaccaaag     1560
aactagatat agggcgaaat gcgaaagact aaaaatcaa caacttaaaa aagggggta     1620
cgcaacagct cattgcggca cccccccgcaa tagctcattg cgtaggttaa agaaaatctg     1680
taattgactg ccacttttac gcaacgcata attgttgtcg cgctgccgaa aagttgcagc     1740
tgattgcgca tggtgccgca accgtgcggc accctaccgc atggagataa gcatggccac     1800
gcagtccaga gaaatcggca ttcaagccaa gaacaagccc ggtcactggg tgcaaacgga     1860
acgcaaagcg catgaggcgt gggccgggct tattgcgagg aaaccacgg cggcaatgct     1920
gctgcatcac ctcgtggcgc agatgggcca ccagaacgcc gtggtggtca gccagaagac     1980
actttccaag ctcatcggac gttctttgcg gacggtccaa tacgcagtca aggacttggt     2040
ggccgagcgc tggatctccg tcgtgaagct caacggcccc ggcaccgtgt cggcctacgt     2100
ggtcaatgac cgcgtggcgt ggggccagcc ccgcgaccag ttgcgcctgt cggtgttcag     2160
tgccgccgtg gtggttgatc acgacgacca ggacgaatcg ctgttggggc atggcgacct     2220
gcgccgcatc ccgaccctgt atccgggcga gcagcaacta ccgaccggcc ccggcgagga     2280
gccgccagc cagcccggca ttccgggcat ggaaccagac ctgccagcct tgaccgaaac     2340
ggaggaatgg gaacggcgcg gcagcagcg cctgccgatg cccgatgagc cgtgtttcct     2400
ggacgatggc gagccgttgg agccgccgac acggtcacg ctgccgcgcc ggtagcactt     2460
gggttgcgca gcaacccgta agtgcgctgt ccagactat cggctgtagc cgcctcgccg     2520
ccctatacct tgtctgcctc cccgcgttgc gtcgcggtgc atggagccgg gccacctcga     2580
cctgaatgga agccggcggc acctcgctaa cggattcacc gttttatca ggctctggga     2640
ggcagaataa atgatcatat cgtcaattat tacctccacg gggagagcct gagcaaactg     2700
gcctcaggca tttgagaagc acacggtcac actgcttccg gtagtcaata aaccggtaaa     2760
ccagcaatag acataagcgg ctatttaacg accctgcctg gaaccgacga ccgggtcgaa     2820
```

```
tttgctttcg aatttctgcc attcatccgc ttattatcac ttattcaggc gtagcaccag    2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggcagtga    3180
gcgcgcgtaa tacgactcac tatagggcga attggagctc caccgcggtg gcggccgctc    3240
tagaactagt ggatccccg gctgcatgc tcgagcggcc gccagtgtga tggatatctg    3300
cagaattcgc ccttcttgat atcttagtgt gcgttaacca ccacccacat tggtccctgc    3360
ccgaccgcat agcggccttt ttcatgcagt agccctgct cgccaacaat ttcgtatacc    3420
gagatgtggt gagatttttg cccggcggca atcagatact tgccgctgtg atcaacattg    3480
aagccgcgcg gctgggtttc cgttggctgg aagccttctt tactcaacac gctgccatct    3540
tccgaaacgc tgaaaacggt aatcaggctg gcggtacggt cgcaggcgta taaatggcga    3600
ccatccgggg tgatatgaat atcagccgcc caacgggtgt cggagaagtt ttccggcatc    3660
atatccagcg tctggacaca ttcgatatta ccgtgcggat ctttcagttc ccagacatcc    3720
actgagctgt ttaactcatt gacgcaatac gcatattgtt cgtttggatg gaataccata    3780
tgacgcgggc cggccccttc aacggtggtc acttccgcag ggtcctgcgc cacgagatga    3840
ccatcatcgc tgaccgtaaa caggcaaatg cgatcctgct taatgccgg aacccacagc    3900
gtacggttgt ccggtgagat attggcggaa tggcaaccgt ccagccctc gaccacatcg    3960
acgacgccca ctggcaggcc atcttccaga cgcgttacgc tcacgttacc cgcattgtaa    4020
gaacctacaa agacaaactg cccctggtga tcggtggaaa tatgcgtcgg actacccggc    4080
agcgcagact ctgcggcaaa ggtcagtgcg ccatcgtccg gggcgatacg atacgccagg    4140
acgcgaaact cagggcgaac accaacatag agataacgtt tgtccgggct gaccaccatc    4200
ggctgcacct gccccggcac atcgacaacc tgtgtcagcg tcagtcgcc ttcatgattc    4260
agattccaga cgtgaatttg ctggctctca gggctggcga tataaactgt ttgcttcatg    4320
aatgctcctt tgggttacct ccgggaaacg cggttgattt gtttagtggt tgaattatt    4380
gctcaggatg tggcatagtc aagggcgtga cggctcgcta atacaactca ctatagggct    4440
cgaggaagtt cctatacttt ctagagaata ggaacttccg cgccgcacac aaaaaccaac    4500
acacagatca tgaaaataaa gctcttttat tggtaccgaa ttcgccaggg agctctcaga    4560
cgtcgcttgg tcggtctta ttcgaacccc agagtcccgc ttacgccccg ccctgccact    4620
catcgcagta ctgttgtaat tcattaagca ttctgccgac atggaagcca tcacaaacgg    4680
catgatgaac ctgaatcgcc agcggcatca gcaccttgtc gccttgcgta taatatttgc    4740
ccatggtgaa aacgggggcg aagaagttgt ccatattggc cacgtttaaa tcaaaactgg    4800
tgaaactcac ccagggattg gctgagacga aaaacatatt ctcaataaac cctttaggga    4860
aataggccag gttttcaccg taacacgcca catcttgcga atatatgtgt agaaactgcc    4920
ggaaatcgtc gtggtattca ctccagagcg atgaaaacgt ttcagtttgc tcatggaaaa    4980
cggtgtaaca agggtgaaca ctatcccata tcaccagctc accgtctttc attgccatac    5040
ggaattccgg atgagcattc atcaggcggg caagaatgtg aataaaggcc ggataaaact    5100
tgtgcttatt tttctttacg gtcttttaaaa aggccgtaat atccagctga acggtctggt    5160
tataggtaca ttgagcaact gactgaaatg cctcaaaatg ttctttacga tgccattggg    5220
```

```
atatatcaac ggtggtatat ccagtgattt ttttctccat ggtttagttc ctcaccttgt   5280
cgtattatac tatgccgata tactatgccg atgattaatt gtcaacacgt gctgctgcag   5340
gtcgaaaggc ccggagatga ggaagaggag aacagcgcgg cagacgtgcg cttttgaagc   5400
gtgcagaatg ccgggcctcc ggaggacctt cgggcgcccg ccccgcccct gagcccgccc   5460
ctgagcccgc ccccggaccc acccctteee agcctctgag cccagaaagc gaaggagcaa   5520
agctgctatt ggccgctgcc ccaaaggcct acccgcttcc attgctcagc ggtgctgtcc   5580
atctgcacga gactagtgag acgtgctact ccatttgtc acgtcctgca cgacgcgagc    5640
tgcggggcgg gggggaactt cctgactagg ggaggagtgg aaggtggcgc gaaggggcca   5700
ccaaagaacg gagccggttg gcgcctaccg gtggatgtgg aatgtgtgcg aggccagagg   5760
ccacttgtgt agcgccaagt gcccagcggg gctgctaaag cgcatgctcc agactgcctt   5820
gggaaaagcg cctcccctac ccggtagaat gaagttccta tactttctag aataggaa    5880 cttcgcggcc gcccctttagt gagggttaat tcaactgact gtaacagcta aaattagtcg   5940
cttttggcgg taagggcgaa ttccagcaca ctggcggccg ttactagtgg atccgagctc   6000
ggtaccaagc ttgatgcagg aattcgatat caagcttatc gataccgtcg acctcgaggg   6060
ggggcccggt acccagcttt tgttcccttt agtgagggtt aattgcgcgc ttggcgtaat   6120
catggtcata gctgtttcct gtgtgaaatt gttatccgct cacaattcca cacaacatac   6180
gagccggaag cataaagtgt aaagcctggg gtgcctaatg agtgagctaa ctcacattaa   6240
ttgcgttgcg ctcactgccc gctttccagt cgggaaacct gtcgtgccag ctgcattaat   6300
gaatcggcca acgcgcgggg agaggcggtt tgcgtattgg gcgcatgcat aaaaactgtt   6360
gtaattcatt aagcattctg ccgacatgga agccatcaca aacggcatga tgaacctgaa   6420
tcgccagcgg catcagcacc ttgtcgcctt gcgtataata tttgcccatg gacgcacacc   6480
gtggaaacgg atgaaggcac gaacccagtt gacataagcc tgttcggttc gtaaactgta   6540
atgcaagtag cgtatgcgct cacgcaactg gtccagaacc ttgaccgaac gcagcggtgg   6600
taacggcgca gtggcggttt tcatggcttg ttatgactgt ttttttgtac agtctatgcc   6660
tcgggcatcc aagcagcaag gcgttacgc cgtgggtcga tgtttgatgt tatggagcag   6720
caacgatgtt acgcagcagc aacgatgtta cgcagcaggg cagtcgccct aaaacaaagt   6780
taggtggctc aagtatgggc atcattcgca catgtaggct cggccctgac caagtcaaat   6840
ccatgcgggc tgctcttgat cttttcggtc gtgagttcgg agacgtagcc acctactccc   6900
aacatcagcc ggactccgat tacctcggga acttgctccg tagtaagaca ttcatcgcgc   6960
ttgctgcctt cgaccaagaa gcggttgttg gcgctctcgc ggcttacgtt ctgcccaggt   7020
ttgagcagcc gcgtagtgag atctatatct atgatctcgc agtctccggc gagcaccgga   7080
ggcagggcat tgccaccgcg ctcatcaatc tcctcaagca tgaggccaac gcgcttggtg   7140
cttatgtgat ctacgtgcaa gcagattacg gtgacgatcc cgcagtggct ctctatacaa   7200
agttgggcat acgggaagaa gtgatgcact ttgatatcga cccaagtacc gccacctaac   7260
aattcgttca agccgagatc ggcttcccgg ccgcggagtt gttcggtaaa ttgtcacaac   7320
gccgccaggt ggcactttc ggggaaatgt gcgcgcccgc gttcctgctg gcgctgggcc   7380
tgtttctggc gctggacttc ccgctgttcc gtcagcagct tttcgcccac ggccttgatg   7440
atcgcggcgg ccttggcctg catatcccga ttcaacggcc caggggcgtc cagaacgggc   7500
ttcaggcgct cccgaaggt                                                 7519
```

<210> SEQ ID NO 7
<211> LENGTH: 6858
<212> TYPE: DNA
<213> ORGANISM: Artificial Sequence
<220> FEATURE:
<223> OTHER INFORMATION: Synthetic Construct

<400> SEQUENCE: 7

| | | | | | |
|---|---|---|---|---|---|
| gtttgacagc | ttatcatcga | ctgcacggtg | caccaatgct | tctggcgtca | ggcagccatc | 60 |
| ggaagctgtg | gtatggctgt | gcaggtcgta | aatcactgca | taattcgtgt | cgctcaaggc | 120 |
| gcactcccgt | tctggataat | gttttttgcg | ccgacatcat | aacggttctg | gcaaatattc | 180 |
| tgaaatgagc | tgttgacaat | taatcatccg | gctcgtataa | tgtgtggaat | tgtgagcgga | 240 |
| taacaatttc | acacaggaaa | cagcgccgct | gagaaaaagc | gaagcggcac | tgctctttaa | 300 |
| caatttatca | gacaatctgt | gtgggcactc | gaccggaatt | atcgattaac | tttattatta | 360 |
| aaaattaaag | aggtatatat | taatgtatcg | attaaataag | gaggaataaa | ccatggaagc | 420 |
| tcgtcgttct | gcgaactacg | aacctaacag | ctgggactat | gattacctgc | tgtcctccga | 480 |
| cacggacgag | tccatcgaag | tatacaaaga | caaagcgaaa | aagctggaag | ccgaagttcg | 540 |
| tcgcgagatt | aataacgaaa | aagcagaatt | tctgaccctg | ctggaactga | ttgacaacgt | 600 |
| ccagcgcctg | ggcctgggtt | accgtttcga | gtctgatatc | cgtggtgcgc | tggatcgctt | 660 |
| cgtttcctcc | ggcggcttcg | atgcggtaac | caagacttcc | ctgcacgtta | cggcactgtc | 720 |
| tttccgtctg | ctgcgtcaac | acggttttga | ggtttctcag | gaagcgttca | gcggcttcaa | 780 |
| agaccaaaac | ggcaacttcc | tggagaacct | gaaggaagat | atcaaagcta | tcctgagcct | 840 |
| gtacgaggcc | agcttcctgg | ctctggaagg | cgaaaacatc | ctggacgagg | cgaaggtttt | 900 |
| cgcaatctct | catctgaaag | aactgtctga | agaaaagatc | ggtaaagagc | tggcagaaca | 960 |
| ggtgaaccat | gcactggaac | tgccactgca | tcgccgtact | cagcgtctgg | aagcagtatg | 1020 |
| gtctatcgag | gcctaccgta | aaaaggagga | cgcgaatcag | ttctgctgg | agctggcaat | 1080 |
| tctggattac | aacatgatcc | agtctgtata | ccagcgtgat | ctgcgtgaaa | cgtcccgttg | 1140 |
| gtggcgtcgt | gtgggtctgg | cgaccaaact | gcactttgct | cgtgaccgcc | tgattgagag | 1200 |
| cttctactgg | gccgtgggtg | tagcattcga | accgcaatac | tccgactgcc | gtaactccgt | 1260 |
| cgcaaaaatg | ttttctttcg | taaccattat | cgacgatatc | tacgatgtat | acggcacccl | 1320 |
| ggacgaactg | gagctgtttta | ctgatgcagt | tgagcgttgg | gacgtaaacg | ccatcaacga | 1380 |
| cctgccggat | tacatgaaac | tgtgctttct | ggctctgtat | aacactatta | acgaaatcgc | 1440 |
| ctacgacaac | ctgaaagata | aggtgagaa | catcctgccg | tatctgacca | agcctgggc | 1500 |
| tgacctgtgc | aacgcttttcc | tgcaagaagc | caagtggctg | tacaacaaat | ctactccgac | 1560 |
| ctttgacgac | tacttcggca | acgcatggaa | atcctcttct | ggcccgctgc | aactggtgtt | 1620 |
| cgcttacttc | gctgtcgtgc | agaacattaa | aaaggaagag | atcgaaaacc | tgcaaaaata | 1680 |
| ccatgacacc | atctctcgtc | cttcccatat | cttccgtctg | tgcaatgacc | tggctagcgc | 1740 |
| gtctgcggaa | attgcgcgtg | gtgaaaccgc | aaatagcgtt | tcttgttaca | tgcgcactaa | 1800 |
| aggtatctcc | gaagaactgg | ctaccgaaag | cgtgatgaat | ctgatcgatg | aaacctggaa | 1860 |
| aaagatgaac | aaggaaaaac | tgggtggtag | cctgttcgcg | aaaccgttcg | tggaaaccgc | 1920 |
| gatcaacctg | gcacgtcaat | ctcactgcac | ttatcataac | ggcgacgcgc | atacctctcc | 1980 |
| ggatgagctg | acccgcaaac | gcgttctgtc | tgtaatcact | gaaccgattc | tgccgtttga | 2040 |
| acgctaactg | cataaaggag | gtaaaaaaac | atggtatcct | gttctgcgcc | gggtaagatt | 2100 |

```
tacctgttcg gtgaacacgc cgtagtttat ggcgaaactg caattgcgtg tgcggtggaa    2160
ctgcgtaccc gtgttcgcgc ggaactcaat gactctatca ctattcagag ccagatcggc    2220
cgcaccggtc tggatttcga aaagcaccct tatgtgtctg cggtaattga gaaaatgcgc    2280
aaatctattc ctattaacgg tgttttcttg accgtcgatt ccgacatccc ggtgggctcc    2340
ggtctgggta gcagcgcagc cgttactatc gcgtctattg gtgcgctgaa cgagctgttc    2400
ggctttggcc tcagcctgca agaaatcgct aaactgggcc acgaaatcga aattaaagta    2460
cagggtgccg cgtccccaac cgatacgtat gtttctacct tcggcggcgt ggttaccatc    2520
ccggaacgtc gcaaactgaa aactccggac tgcggcattg tgattggcga taccggcgtt    2580
ttctcctcca ccaaagagtt agtagctaac gtacgtcagc tgcgcgaaag ctacccggat    2640
ttgatcgaac cgctgatgac ctctattggc aaaatctctc gtatcggcga caactggtt    2700 ctgtctggcg actacgcatc catcggccgc ctgatgaacg tcaaccaggg tctcctggac    2760
gccctgggcg ttaacatctt agaactgagc cagctgatct attccgctcg tgcggcaggt    2820
gcgtttggcg ctaaaatcac gggcgctggc ggcggtggct gtatggttgc gctgaccgct    2880
ccggaaaaat gcaaccaagt ggcagaagcg gtagcaggcg ctggcggtaa agtgactatc    2940
actaaaccga ccgagcaagg tctgaaagta gattaaagtc tagttaaagt ttaaacggtc    3000
tccagcttgg ctgttttggc ggatgagaga agattttcag cctgatacag attaaatcag    3060
aacgcagaag cggtctgata aaacagaatt tgcctggcgg cagtagcgcg gtggtcccac    3120
ctgaccccat gccgaactca gaagtgaaac gccgtagcgc cgatggtagt gtggggtctc    3180
cccatgcgag agtagggaac tgccaggcat caaataaaac gaaaggctca gtcgaaagac    3240
tgggcctttc gttttatctg ttgtttgtcg gtgaacgctc tcctgagtag acaaatccg    3300 ccgggagcgg atttgaacgt tgcgaagcaa cggcccggag ggtggcgggc aggacgcccg    3360
ccataaactg ccaggcatca aattaagcag aaggccatcc tgacggatgg cctttttgcg    3420
tttctacaaa ctcttttttgt ttattttttct aaatacattc aaatatgtat ccgctcatga    3480
gacaataacc ctgataaatg cttcaataat attgaaaaag gaagagtatg agtattcaac    3540
atttccgtgt cgcccttatt ccctttttttg cggcattttg ccttcctgtt tttgctcacc    3600
cagaaacgct ggtgaaagta aaagatgctg aagatcagtt gggtgcacga gtgggttaca    3660
tcgaactgga tctcaacagc ggtaagatcc ttgagagttt tcgccccgaa gaacgttttc    3720
caatgatgag cacttttaaa gttctgctat gtggcgcggt attatcccgt gttgacgccg    3780
ggcaagagca actcggtcgc cgcatacact attctcagaa tgacttggtt gagtactcac    3840
cagtcacaga aaagcatctt acggatggca tgacagtaag agaattatgc agtgctgcca    3900
taaccatgag tgataacact gcggccaact tacttctgac aacgatcgga ggaccgaagg    3960
agctaaccgc ttttttgcac aacatggggg atcatgtaac tcgccttgat cgttgggaac    4020
cggagctgaa tgaagccata ccaaacgacg agcgtgacac cacgatgcct gtagcaatgg    4080
caacaacgtt gcgcaaacta ttaactggcg aactacttac tctagcttcc cggcaacaat    4140
taatagactg gatggaggcg gataaagttg caggaccact tctgcgctcg gcccttccgg    4200
ctggctggtt tattgctgat aaatctggag ccggtgagcg tgggtctcgc ggtatcattg    4260
cagcactggg gccagatggt aagccctccc gtatcgtagt tatctacacg acggggagtc    4320
aggcaactat ggatgaacga aatagacaga tcgctgagat aggtgcctca ctgattaagc    4380
attggtaact gtcagaccaa gtttactcat atatacttta gattgattta aaacttcatt    4440
```

```
tttaattttaa aaggatctag gtgaagatcc tttttgataa tctcatgacc aaaatccctt    4500
aacgtgagtt ttcgttccac tgagcgtcag accccgtaga aaagatcaaa ggatcttctt    4560
gagatccttt ttttctgcgc gtaatctgct gcttgcaaac aaaaaaacca ccgctaccag    4620
cggtggtttg tttgccggat caagagctac caactctttt tccgaaggta actggcttca    4680
gcagagcgca gataccaaat actgtccttc tagtgtagcc gtagttaggc caccacttca    4740
agaactctgt agcaccgcct acatacccg ctctgctaat cctgttacca gtggctgctg    4800
ccagtggcga taagtcgtgt cttaccgggt tggactcaag acgatagtta ccggataagg    4860
cgcagcggtc gggctgaacg gggggttcgt gcacacagcc cagcttggag cgaacgacct    4920
acaccgaact gagataccta cagcgtgagc tatgagaaag cgccacgctt cccgaaggga    4980
gaaaggcgga caggtatccg gtaagcggca gggtcggaac aggagagcgc acgagggagc    5040
ttccaggggg aaacgcctgg tatctttata gtcctgtcgg gtttcgccac ctctgacttg    5100
agcgtcgatt tttgtgatgc tcgtcagggg gcggagcct atggaaaaac gccagcaacg    5160 cggcctttt acgttcctg gccttttgct ggccttttgc tcacatgttc tttcctgcgt    5220
tatcccctga ttctgtggat aaccgtatta ccgcctttga gtgagctgat accgctcgcc    5280
gcagccgaac gaccgagcgc agcgagtcag tgagcgagga gcggaagag cgcctgatgc    5340 ggtattttct ccttacgcat ctgtgcggta tttcacaccg catatggtgc actctcagta    5400
caatctgctc tgatgccgca tagttaagcc agtatacact ccgctatcgc tacgtgactg    5460
ggtcatggct gcgccccgac acccgccaac accgctgac gcgccctgac gggcttgtct    5520
gctcccggca tccgcttaca gacaagctgt gaccgtctcc gggagctgca tgtgtcagag    5580
gttttcaccg tcatcaccga aacgcgcgag gcagcagatc aattcgcgcg cgaaggcgaa    5640
gcggcatgca tttacgttga caccatcgaa tggtgcaaaa cctttcgcgg tatggcatga    5700
tagcgcccgg aagagagtca attcaggtg gtgaatgtga aaccagtaac gttatacgat    5760
gtcgcagagt atgccggtgt ctcttatcag accgttccc gcgtggtgaa ccaggccagc    5820
cacgtttctg cgaaaacgcg ggaaaaagtg gaagcggcga tggcggagct gaattacatt    5880
cccaaccgcg tggcacaaca actggcgggc aaacagtcgt tgctgattgg cgttgccacc    5940
tccagtctgg ccctgcacgc gccgtcgcaa attgtcgcgg cgattaaatc tcgcgccgat    6000
caactgggtg ccagcgtggt ggtgtcgatg gtagaacgaa gcggcgtcga agcctgtaaa    6060
gcggcggtgc acaatcttct cgcgcaacgc gtcagtgggc tgatcattaa ctatccgctg    6120
gatgaccagg atgccattgc tgtggaagct gcctgcacta atgttccggc gttatttctt    6180
gatgtctctg accagacacc catcaacagt attattttct cccatgaaga cggtacgcga    6240
ctgggcgtgg agcatctggt cgcattgggt caccagcaaa tcgcgctgtt agcgggccca    6300
ttaagttctg tctcggcgcg tctgcgtctg gctggctggc ataaatatct cactcgcaat    6360
caaattcagc cgatagcgga acgggaaggc gactggagtg ccatgtccgg ttttcaacaa    6420
accatgcaaa tgctgaatga gggcatcgtt cccactgcga tgctggttgc caacgatcag    6480
atggcgctgg gcgcaatgcg cgccattacc gagtccgggc tgcgcgttgg tgcggatatc    6540
tcggtagtgg gatacgacga taccgaagac agctcatgtt atatcccgcc gtcaaccacc    6600
atcaaacagg atttcgcct gctggggcaa accagcgtgg accgcttgct gcaactctct    6660
cagggccagg cggtgaaggg caatcagctg ttgcccgtct cactggtgaa agaaaaaacc    6720
accctggcgc ccaatacgca aaccgcctct ccccgcgcgt tggccgattc attaatgcag    6780
ctggcacgac aggtttcccg actggaaagc gggcagtgag cgcaacgcaa ttaatgtgag    6840
```
ttagcgcgaa ttgatctg                                                    6858

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
gacgctttcg ccaagtcagg                                                    20

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
gtcaggctgg aatactcttc g                                                  21

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
accaattgca cccggcaga                                                     19

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
gctaaagcgc atgctccaga c                                                  21

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
gactggcctc agatgaaagc                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
caaacatgtg gcatggaaag                                                    20

<210> SEQ ID NO 14
<211> LENGTH: 52
<212> TYPE: DNA

```
<213> ORGANISM: Artificial Sequence
<220> FEATURE:
<223> OTHER INFORMATION: Synthetic Construct

<400> SEQUENCE: 14
gggcccgttt aaactttaac tagactctgc agttagcgtt caaacggcag aa          52

<210> SEQ ID NO 15
<211> LENGTH: 38
<212> TYPE: DNA
<213> ORGANISM: Artificial Sequence
<220> FEATURE:
<223> OTHER INFORMATION: Synthetic Construct

<400> SEQUENCE: 15
cgcatgcatg tcatgagatg tagcgtgtcc accgaaaa                          38

<210> SEQ ID NO 16
<211> LENGTH: 22
<212> TYPE: DNA
<213> ORGANISM: Artificial Sequence
<220> FEATURE:
<223> OTHER INFORMATION: Synthetic Construct

<400> SEQUENCE: 16
acaatttcac acaggaaaca gc                                           22

<210> SEQ ID NO 17
<211> LENGTH: 23
<212> TYPE: DNA
<213> ORGANISM: Artificial Sequence
<220> FEATURE:
<223> OTHER INFORMATION: Synthetic Construct

<400> SEQUENCE: 17
ccaggcaaat tctgttttat cag                                          23

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct

<400> SEQUENCE: 18
gcactgtctt tccgtctgct gc                                           22

<210> SEQ ID NO 19
<211> LENGTH: 66
<212> TYPE: DNA
<213> ORGANISM: Artificial Sequence
<220> FEATURE:
<223> OTHER INFORMATION: Synthetic Construct

<400> SEQUENCE: 19
gcgaacgatg cataaaggag gtaaaaaaac atggtatcct gttctgcgcc gggtaagatt  60
tacctg                                                             66

<210> SEQ ID NO 20
<211> LENGTH: 48
<212> TYPE: DNA
<213> ORGANISM: Artificial Sequence
<220> FEATURE:
<223> OTHER INFORMATION: Synthetic Construct

<400> SEQUENCE: 20
```

```
gggcccgttt aaactttaac tagactttaa tctactttca gaccttgc          48
```

<210> SEQ ID NO 21
<211> LENGTH: 24
<212> TYPE: DNA
<213> ORGANISM: Artificial Sequence
<220> FEATURE:
<223> OTHER INFORMATION: Synthetic Construct

<400> SEQUENCE: 21

```
gatagtaacg gctgcgctgc tacc                                    24
```

<210> SEQ ID NO 22
<211> LENGTH: 23
<212> TYPE: DNA
<213> ORGANISM: Artificial Sequence
<220> FEATURE:
<223> OTHER INFORMATION: Synthetic Construct

<400> SEQUENCE: 22

```
gacagcttat catcgactgc acg                                     23
```

<210> SEQ ID NO 23
<211> LENGTH: 22
<212> TYPE: DNA
<213> ORGANISM: Artificial Sequence
<220> FEATURE:
<223> OTHER INFORMATION: Synthetic Construct

<400> SEQUENCE: 23

```
caccatggta tcctgttctg cg                                      22
```

<210> SEQ ID NO 24
<211> LENGTH: 22
<212> TYPE: DNA
<213> ORGANISM: Artificial Sequence
<220> FEATURE:
<223> OTHER INFORMATION: Synthetic Construct

<400> SEQUENCE: 24

```
ttaatctact ttcagacctt gc                                      22
```

<210> SEQ ID NO 25
<211> LENGTH: 67
<212> TYPE: DNA
<213> ORGANISM: Artificial Sequence
<220> FEATURE:
<223> OTHER INFORMATION: Synthetic Construct

<400> SEQUENCE: 25

```
accgccaaaa gcgactaatt ttagctgtta cagtcagttg aattaaccct cactaaaggg    60
cggccgc                                                             67
```

<210> SEQ ID NO 26
<211> LENGTH: 152
<212> TYPE: DNA
<213> ORGANISM: Artificial Sequence
<220> FEATURE:
<223> OTHER INFORMATION: Synthetic Construct

<400> SEQUENCE: 26

```
gctggcgata taaactgttt gcttcatgaa tgctcctttg ggttacctcc gggaaacgcg    60
gttgatttgt ttagtggttg aattatttgc tcaggatgtg gcatagtcaa gggcgtgacg   120
```

```
gctcgctaat acgactcact atagggctcg ag                                          152
```

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27

```
accgccaaaa gcgactaatt ttagct                                                 26
```

<210> SEQ ID NO 28
<211> LENGTH: 30
<212> TYPE: DNA
<213> ORGANISM: Artificial Sequence
<220> FEATURE:
<223> OTHER INFORMATION: Synthetic Construct

<400> SEQUENCE: 28

```
cttgatatct tagtgtgcgt taaccaccac                                             30
```

<210> SEQ ID NO 29
<211> LENGTH: 21
<212> TYPE: DNA
<213> ORGANISM: Artificial Sequence
<220> FEATURE:
<223> OTHER INFORMATION: Synthetic Construct

<400> SEQUENCE: 29

```
cgtgaatttg ctggctctca g                                                      21
```

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct

<400> SEQUENCE: 30

```
ggtttagttc ctcaccttgt c                                                      21
```

<210> SEQ ID NO 31
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31

```
actgaaacgt tttcatcgct c                                                      21
```

<210> SEQ ID NO 32
<211> LENGTH: 81
<212> TYPE: DNA
<213> ORGANISM: Artificial Sequence
<220> FEATURE:
<223> OTHER INFORMATION: Synthetic Construct

<400> SEQUENCE: 32

```
aaagtagccg aagatgacgg tttgtcacat ggagttggca ggatgtttga ttaaaagcaa            60
ttaaccctca ctaaagggcg g                                                      81
```

<210> SEQ ID NO 33
<211> LENGTH: 199

<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 112
<223> OTHER INFORMATION: n = A,T,C or G

<400> SEQUENCE: 33

| | |
|---|---|
| taaatcttac ccggcgcaga acaggatacc atgttttttt acctcctttg caccttcatg | 60 |
| gtggtcagtg cgtcctgctg atgtgctcag tatcaccgcc agtggtattt angtcaacac | 120 |
| cgccagagat aatttatcac cgcagatggt tatctgtatg ttttttatat gaatttaata | 180 |
| cgactcacta tagggctcg | 199 |

<210> SEQ ID NO 34
<211> LENGTH: 24
<212> TYPE: DNA
<213> ORGANISM: Artificial Sequence
<220> FEATURE:
<223> OTHER INFORMATION: Synthetic Construct

<400> SEQUENCE: 34

| | |
|---|---|
| aaagaccgac caagcgacgt ctga | 24 |

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct

<400> SEQUENCE: 35

| | |
|---|---|
| gctctgaata gtgatagagt ca | 22 |

<210> SEQ ID NO 36
<211> LENGTH: 445
<212> TYPE: DNA
<213> ORGANISM: Artificial Sequence
<220> FEATURE:
<223> OTHER INFORMATION: Synthetic Construct

<400> SEQUENCE: 36

| | |
|---|---|
| aaagaccgac caagcgacgt ctgagagctc cctggcgaat tcggtaccaa taaaagagct | 60 |
| ttattttcat gatctgtgtg ttggttttg tgtgcggcgc ggaagttcct attctctaga | 120 |
| aagtatagga acttcctcga gccctatagt gagtcgtatt aaattcatat aaaaaacata | 180 |
| cagataacca tctgcggtga taaattatct ctggcggtgt tgacataaat accactggcg | 240 |
| gtgatactga gcacatcagc aggacgcact gaccaccatg aaggtgcaaa ggaggtaaaa | 300 |
| aaacatggta tcctgttctg cgccgggtaa gatttacctg ttcggtgaac acgccgtagt | 360 |
| ttatggcgaa actgcaattg cgtgtgcggt ggaactgcgt acccgtgttc gcgcggaact | 420 |
| caatgactct atcactattc agagc | 445 |

<210> SEQ ID NO 37
<211> LENGTH: 445
<212> TYPE: DNA
<213> ORGANISM: Artificial Sequence
<220> FEATURE:
<223> OTHER INFORMATION: Synthetic Construct

<400> SEQUENCE: 37

```
aaagaccgac caagcgacgt ctgagagctc cctggcgaat tcggtaccaa taaaagagct    60 ttatttcat gatctgtgtg ttggttttg tgtgcggcgc ggaagttcct attctctaga    120
aagtatagga acttcctcga gccctatagt gagtcgtatt aaattcatat aaaaaacata   180
cagataacca tctgcggtga taaattatct ctggcggtgt tgacctaaat accactggcg   240
gtgatactga gcacatcagc aggacgcact gaccaccatg aaggtgcaaa ggaggtaaaa   300
aaacatggta tcctgttctg cgccgggtaa gatttacctg ttcggtgaac acgccgtagt   360
ttatggcgaa actgcaattg cgtgtgcggt ggaactgcgt acccgtgttc gcgcggaact   420
caatgactct atcactattc agagc                                         445
```

```
<210> SEQ ID NO 38
<211> LENGTH: 442
<212> TYPE: DNA
<213> ORGANISM: Artificial Sequence
<220> FEATURE:
<223> OTHER INFORMATION: Synthetic Construct

<400> SEQUENCE: 38
aaagaccgac caagcgacgt ctgagagctc cctggcgaat tcggtaccaa taaaagagct    60 ttatttcat gatctgtgtg ttggttttg tgtgcggcgc ggaagttcct attctctaga    120
aagtatagga acttcctcga gccctatagt gagtcgtatt aaattcatat aaaaaacata   180
cagataacca tctgcggtga taaattatct ctggcggtgt tgacctaaat accactggcg   240
gtgatactga gcacatcagc aggacgcact gaccaccatg aaggtgcaaa ggtaaaaaaa   300
catggtatcc tgttctgcgc cgggtaagat ttacctgttc ggtgaacacg ccgtagttta   360
tggcgaaact gcaattgcgt gtgcggtgga actgcgtacc cgtgttcgcg cggaactcaa   420
tgactctatc actattcaga gc                                            442
```

```
<210> SEQ ID NO 39
<211> LENGTH: 445
<212> TYPE: DNA
<213> ORGANISM: Artificial Sequence
<220> FEATURE:
<223> OTHER INFORMATION: Synthetic Construct

<400> SEQUENCE: 39
aaagaccgac caagcgacgt ctgagagctc cctggcgaat tcggtaccaa taaaagagct    60 ttatttcat gatctgtgtg ttggttttg tgtgcggcgc ggaagttcct attctctaga    120
aagtatagga acttcctcga gccctatagt gagtcgtatt aaattcatat aaaaaacata   180
cagataacca tctgcggtga taaattatct ctggcggtgt tgacgtaaat accactggcg   240
gtgatactga gcacatcagc aggacgcact gaccaccatg aaggtgcaaa ggaggtaaaa   300
aaacatggta tcctgttctg cgccgggtaa gatttacctg ttcggtgaac acgccgtagt   360
ttatggcgaa actgcaattg cgtgtgcggt ggaactgcgt acccgtgttc gcgcggaact   420
caatgactct atcactattc agagc                                         445
```

```
<210> SEQ ID NO 40
<211> LENGTH: 30
<212> TYPE: DNA
<213> ORGANISM: Artificial Sequence
<220> FEATURE:
<223> OTHER INFORMATION: Synthetic Construct

<400> SEQUENCE: 40
gaggaataaa ccatggaagc tcgtcgttct                                     30
```

<210> SEQ ID NO 41
<211> LENGTH: 30
<212> TYPE: DNA
<213> ORGANISM: Artificial Sequence
<220> FEATURE:
<223> OTHER INFORMATION: Synthetic Construct

<400> SEQUENCE: 41
agaacgacga gcttccatgg tttattcctc                                   30

<210> SEQ ID NO 42

<400> SEQUENCE: 42

000

<210> SEQ ID NO 43

<400> SEQUENCE: 43

000

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct

<400> SEQUENCE: 44
ctcgtacagg ctcaggatag                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic Construct

<400> SEQUENCE: 45
ttacgtccca acgctcaact                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic Construct

<400> SEQUENCE: 46
cttcggcaac gcatggaaat                                              20

<210> SEQ ID NO 47

<400> SEQUENCE: 47

000

US 8,778,647 B2

METHODS OF PRODUCING ISOPRENE COMPRISING A MEMBRANE BIOREACTOR

CROSS-REFERENCE TO RELATED APPLICATIONS

This application claims priority to U.S. Provisional Patent Application No. 61/289,352, filed on Dec. 22, 2009, the disclosure of which is hereby incorporated herein by reference in its entirety.

FIELD OF THE INVENTION

This disclosure relates to improved methods for the production of isoprene.

BACKGROUND OF THE INVENTION

Isoprene (2-methyl-1,3-butadiene) is an important organic compound used in a wide array of applications. For instance, isoprene is employed as an intermediate or a starting material in the synthesis of numerous chemical compositions and polymers. Isoprene is also an important biological material that is synthesized naturally by many plants and animals, including humans.

The isoprene used in industrial applications is typically produced as a by-product of the thermal cracking of petroleum or naphtha or is otherwise extracted from petrochemical streams. This is a relatively expensive, energy-intensive process. With the worldwide demand for petrochemical based products constantly increasing, the cost of isoprene is expected to rise to much higher levels in the long-term and its availability is limited in any case. There is concern that future supplies of isoprene from petrochemical-based sources will be inadequate to meet projected needs and that prices will rise to unprecedented levels. Accordingly, there is a need to procure a source of isoprene from a low cost, renewable source which is environmentally friendly.

Several recent advancements have been made in the production of isoprene from renewable sources (see, for example, International Patent Application Publication No. WO 2009/076676 A2). Such methods produce isoprene at rates, titers, and purity that may be sufficient to meet the demands of a robust commercial process, however process improvements to reduce the operational costs associated with the production of isoprene derived from biological sources, and to increase yields of isoprene are needed.

All patents, patent applications, publications, documents, nucleotide and protein sequence database accession numbers, the sequences to which they refer, and articles cited herein are all incorporated herein by reference in their entireties.

BRIEF SUMMARY OF THE INVENTION

Disclosed herein are improved methods for the production of isoprene from biological materials, comprising the operation of a membrane bioreactor in conjunction with a bioreactor culturing isoprene-producing cells.

In one aspect, provided herein are improved methods of producing isoprene, the methods comprising: (a) culturing cells comprising a heterologous nucleic acid encoding an isoprene synthase polypeptide under suitable culture conditions for the production of isoprene, wherein the cells either (i) produce isoprene at a titer greater than 40 g/L or (ii) have an average volumetric productivity of isoprene greater than about 500 mg/$L_{broth}$/hr of isoprene; (b) removing a portion of the culture; (c) filtering the removed portion of the culture to produce a permeate and a retentate; (d) returning the retentate to the culture; and (e) producing isoprene; wherein the cultured cells undergoing steps (b), (c), and (d) either (i) produce isoprene at a higher titer, or (ii) have greater average volumetric productivity of isoprene than the same cells cultured without undergoing steps (b), (c), and (d).

In another aspect, provided herein are improved methods of producing isoprene, the methods comprising: (a) culturing cells comprising a heterologous nucleic acid encoding an isoprene synthase polypeptide under suitable culture conditions for the production of isoprene, wherein the cells either (i) produce isoprene at a titer greater than 40 g/L (ii) have an average volumetric productivity of isoprene greater than about 500 mg/$L_{broth}$/hr of isoprene; (b) removing a portion of the culture; (c) filtering the removed portion of the culture to produce a permeate and a retentate; (d) returning the retentate, to the culture; (e) producing isoprene; and (f) recovering the isoprene; wherein the cultured cells undergoing steps (b), (c), and (d) either (i) produce isoprene at a higher titer, or (ii) have greater average volumetric productivity of isoprene than the same cells cultured without undergoing steps (b), (c), and (d). In some aspects, the filtering is by tangential flow filtration.

In some aspects, the cells produce isoprene at a titer of greater than about 40 g/L. In some aspects, the cells produce isoprene at a titer of greater than about 50 g/L. In some aspects, the cells produce isoprene at a titer of greater than about 60 g/L. In some aspects, the cells produce isoprene at a titer of greater than about 70 g/L. In some aspects, the cells produce isoprene at a titer of greater than about 80 g/L. In some aspects, the cells produce isoprene at a titer of greater than about 90 g/L. In some aspects, the cells produce isoprene at a titer of greater than about 100 g/L. In some aspects, the cells produce isoprene at a titer of greater than about 110 g/L. In some aspects, the cells produce isoprene at a titer of greater than about 120 g/L. In some aspects, the cells produce isoprene at a titer of greater than about 130 g/L. In some aspects, the cells produce isoprene at a titer of greater than about 140 g/L. In some aspects, the cells produce isoprene at a titer of greater than about 150 g/L. In some aspects, the cells produce isoprene at a titer of greater than about 160 g/L. In some aspects, the cells produce isoprene at a titer of greater than about 170 g/L. In some aspects, the cells produce isoprene at a titer of greater than about 180 g/L. In some aspects, the cells produce isoprene at a titer of greater than about 190 g/L. In some aspects, the cells produce isoprene at a titer of greater than about 200 g/L. In some aspects, the cells produce isoprene at a titer between about 40 g/L and about 100 g/L. In some aspects, the cells produce isoprene at a titer between about 60 g/L and about 100 g/L. In some aspects, the cells produce isoprene at a titer between about 60 g/L and about 120 g/L. In some aspects, the cells produce isoprene at a titer between about 40 g/L and about 150 g/L. In some aspects, the cells produce isoprene at a titer between about 40 g/L and about 200 g/L. In some aspects, the cells produce isoprene at a titer between about 80 g/L and about 150 g/L. In some aspects, the cells produce isoprene at a titer between about 100 g/L and about 150 g/L. In some aspects, the cells produce isoprene at a titer between about 100 g/L and about 180 g/L. In some aspects, the cells produce isoprene at a titer between about 100 g/L and about 200 g/L. In some aspects, the cells produce isoprene at a titer between about 120 g/L and about 200 g/L. In some aspects, the cells have an average volumetric productivity of greater than about 500 mg/$L_{broth}$/hr of isoprene. In some aspects, the cells have an average volumetric productivity greater than about 1,000 mg/$L_{broth}$/hr of isoprene. In some aspects, the cells have an average volumetric productivity greater than about 1,500 mg/L$_{broth}$/hr of isoprene. In some aspects, the cells have an average volumetric productivity greater than about 2,000 mg/L$_{broth}$/hr of isoprene. In some aspects, the cells have an average volumetric productivity between about 500 mg/L$_{broth}$/hr and about 2,000 mg/L$_{broth}$/hr of isoprene.

In some aspects, the method further comprises a step of recycling the permeate back into the same cell culture or into another cell culture, wherein the cells cultured in the presence of recycled permeate have greater average specific productivity of isoprene than the same cells cultured in the absence of recycled permeate. In some aspects, the cells have about two times the average specific productivity of isoprene than the same cells cultured in the absence of recycled permeate. In some aspects, the cells have about three times the average specific productivity of isoprene than the same cells cultured in the absence of recycled permeate. In some aspects, the portion of the culture is removed continuously. In some aspects, the portion of the culture is removed discontinuously.

In some aspects, the isoprene synthase polypeptide is a plant isoprene synthase polypeptide. In some aspects, the cells further comprise a heterologous nucleic acid encoding an IDI polypeptide. In some aspects, the cells further comprise a chromosomal copy of an endogenous nucleic acid encoding an IDI polypeptide. In some aspects, the cells further comprise a heterologous nucleic acid encoding a DXP pathway polypeptide, in some aspects, the cells further comprise a heterologous nucleic acid encoding a DXS polypeptide. In some aspects, the cells further comprise a chromosomal copy of an endogenous nucleic acid encoding a DXS polypeptide. In some aspects, the cells further comprise one or more nucleic acids encoding an IDI polypeptide and a DXS polypeptide or a DXP pathway polypeptide. In some aspects, one nucleic acid encodes the isoprene synthase polypeptide, IDI polypeptide, and DXS polypeptide or a DXP pathway polypeptide, in some aspects, one plasmid encodes the isoprene synthase polypeptide, IDI polypeptide, and DXS polypeptide. In some aspects, the cells further comprise a heterologous nucleic acid encoding an MVA pathway polypeptide. In some aspects, the MVA pathway polypeptide is a mevalonate kinase (MVK) polypeptide. In some aspects, the MVK polypeptide is a polypeptide from the genus *Methanosarcina*. In some aspects, the *Methanosarcina* is *Methanosarcina mazei*.

In some aspects, the isoprene synthase polypeptide is a naturally-occurring polypeptide from the genus *Pueraria*. In some aspects, the isoprene synthase polypeptide is a naturally-occurring polypeptide from *Pueraia montarta*. In some aspects, the isoprene synthase polypeptide is a naturally-occurring polypeptide from the genus *Populus*. In some aspects, the isoprene synthase polypeptide is a naturally-occurring polypeptide from *Populus alba*. In some aspects, the cells further comprise a heterologous nucleic acid encoding an MVA pathway polypeptide. In some aspects, the MVA pathway polypeptide is a mevalonate kinase (MVK). In some aspects, the MVK is from the genus *Methanosarcina*. In some aspects, the MVK is from *Methanosarcina mazei*. In some aspects, the cells are bacterial cells. In some aspects, the cells are gram-positive bacterial cells. In some aspects, the cells are *Bacillus* cells. In some aspects, the cells are *Bacillus subtilis* cells. In some aspects, the cells are gram-negative bacterial cells. In some aspects, the cells are *Escherichia* or *Pantoea* cells. In some aspects, the cells are *Escherichia coli* or *Pantoea citrea* cells. In some aspects, the cells are fungal cells. In some aspects, the cells are *Trichoderma* cells. In some aspects, the cells are *Trichoderma reesei* cells. In some aspects, the cells are yeast cells. In some aspects, the cells are *Yarrowia* cells. In some aspects, the cells are *Yarrowia lipolytica* cells.

In some aspects, the cells comprise (i) pan integrated nucleic acid encoding the lower MVA pathway from *S. cerevisiae* comprising a glucose isomerase promoter and a nucleic acid encoding mevalonate kinase (MVK); a nucleic acid encoding phosphomevalonate kinase (PMK); a nucleic acid encoding diphosphomevalonate decarboxylase (MVD); and a nucleic acid encoding isopentenyl diphosphate isomerase (IDI); (ii) a nucleic acid encoding *P. alba* isoprene synthase; (iii) a nucleic acid encoding *M. mazei* mevalonate kinase; and (iv) a nucleic acid encoding the upper MVA pathway from *Enterococcus faecalis*, comprising a nucleic acid encoding an acetoacetyl-Coenzyme A synthase (thiolase) polypeptide; a nucleic acid encoding a 3-hydroxy-3-methylglutaryl-Coenzyme A synthase polypeptide; and a nucleic acid encoding a 3-hydroxy-3-methylglutaryl-Coenzyme A reductase polypeptide.

In another aspect, provided herein are improved methods of producing isoprene, the methods comprising: (a) culturing cells comprising a heterologous nucleic acid encoding an isoprene synthase polypeptide in a fermentor containing growth medium under suitable culture conditions for the production of isoprene, wherein the cells either (i) produce isoprene at a titer greater than 40 g/L or (ii) have an average volumetric productivity of isoprene greater than about 500 mg/L$_{broth}$/hr of isoprene; (b) removing a portion of the cell culture from the fermentor; (c) transferring the removed portion of the cell culture to a filter; (d) filtering the removed portion of the cell culture to form: (i) a permeate comprising spent growth medium; and (ii) a retentate comprising cells and other culture solids; (e) returning the retentate to the fermentor; (f) collecting the permeate; and (g) producing isoprene; wherein the cultured cells undergoing steps (b) (c), (d) and (e) either (i) produce isoprene at a higher titer, or (ii) have greater average volumetric productivity of isoprene than the same cells cultured without undergoing steps (b), (c), (d), and (e).

In another aspect, provided herein are improved methods of producing isoprene, the methods comprising: (a) culturing cells comprising a heterologous nucleic acid encoding an isoprene synthase polypeptide in a fermentor containing growth medium under suitable culture conditions for the production of isoprene, wherein the cells either (i) produce isoprene at a titer greater than 40 g/L or (ii) have an average volumetric productivity of isoprene greater than about 500 mg/L$_{broth}$/hr of isoprene; (b) removing a portion of the cell culture from the fermentor; (c) transferring the removed portion of the cell culture to a filter; (d) filtering the removed portion of the cell culture to form: (i) a permeate comprising spent growth medium; and (ii) a retentate comprising cells and other culture solids; (e) returning the retentate to the fermentor; (f) collecting the permeate; (g) producing isoprene; and (h) recovering the isoprene; wherein the cultured cells undergoing steps (b), (c), (d) and (e) either (i) produce isoprene at a higher titer, or (ii) have greater average volumetric productivity of isoprene than the same cells cultured without undergoing steps (b), (c), (d), and (e).

In some aspects, the fermentor and the filter are connected by a circulation loop and a circulation pump. In some aspects, the permeate is collected from the filter by a permeate collection outlet and a permeate pump and stored in a permeate collection tank. In some aspects, the permeate collection tank further comprises a vent to relieve pressure within the tank. In some aspects, the circulation pump and the permeate pump are peristaltic pumps. In some aspects, the filter is a microfilter. In some aspects, the filter is an ultrafilter. In some aspects, the microfilter is a tangential flow filter. In some aspects, the tangential flow filter has a filter pore size between about 0.005 µm and about 100 µm. In some aspects, the tangential flow filter has a filter pore size between about 0.05 µm and about 10 µm. In some aspects, the ultrafilter is a tangential flow filter. In some aspects, the tangential flow filter has a nominal molecular weight cutoff (NMWC) greater than about 100,000. In some aspects, the tangential flow filter has a NMWC greater than about 250,000. In some aspects, the tangential flow filter is a GE Healthcare Xampler™ Ultrafiltration Cartridge having a 500,000 nominal molecular weight cutoff (NMWC) and comprising a hollow fiber membrane.

In some aspects, the method further comprises the steps of (i) monitoring the inlet pressure of the filter with an inlet pressure gauge ($P_{in}$); (ii) monitoring the outlet pressure of the filter with an outlet pressure gauge ($P_{out}$); (iii) monitoring the pressure in the permeate collection outlet with a permeate pressure gauge ($P_{perm}$); and (iv) determining the transmembrane pressure (TMP) across the filter. In some aspects, the method further comprises the step of maintaining positive TMP across the filter. in some aspects, the fermentor further comprises an isoprene collection outlet connected to an isoprene storage tank.

In some aspects, the cells produce isoprene at a titer of greater than about 40 g/L. In some aspects, the cells produce isoprene at a titer of greater than about 50 g/L. In some aspects, the cells produce isoprene at a titer of greater than about 60 g/L. In some aspects, the cells produce isoprene at a titer of greater than about 70 g/L. In some aspects, the cells produce isoprene at a titer of greater than about 80 g/L. In some aspects, the cells produce isoprene at a titer of greater than about 90 g/L. In some aspects, the cells produce isoprene at a titer of greater than about 100 g/L. In some aspects, the cells produce isoprene at a titer of greater than about 110 g/L. In some aspects, the cells produce isoprene at a titer of greater than about 120 g/L. In some aspects, the cells produce isoprene at a titer of greater than about 130 g/L. In some aspects, the cells produce isoprene at a titer of greater than about 140 g/L. In some aspects, the cells produce isoprene at a titer of greater than about 150 g/L. In some aspects, the cells produce isoprene at a titer of greater than about 160 g/L. In some aspects, the cells produce isoprene at a titer of greater than about 170 g/L. In some aspects, the cells produce isoprene at a titer of greater than about 180 g/L. In some aspects, the cells produce isoprene at a titer of greater than about 190 g/L. In some aspects, the cells produce isoprene at a titer of greater than about 200 g/L. In some aspects, the cells produce isoprene at a titer between about 40 g/L and about 100 g/L. In some aspects, the cells produce isoprene at a titer between about 60 g/L and about 100 g/L. In some aspects, the cells produce isoprene at a titer between about 60 g/L and about 120 g/L. In some aspects, the cells produce isoprene at a titer between about 40 g/L and about 150 g/L. In some aspects, the cells produce isoprene at a titer between about 40 g/L and about 200 g/L. In some aspects, the cells produce isoprene at a titer between about 80 g/L and about 150 g/L. In some aspects, the cells produce isoprene at a titer between about 100 g/L and about 150 g/L. In some aspects, the cells produce isoprene at a titer between about 100 g/L and about 180 g/L. In some aspects, the cells produce isoprene at a titer between about 100 g/L, and about 200 g/L. In some aspects, the cells produce isoprene at a titer between about 120 g/L and about 200 g/L. In some aspects, the cells have an average volumetric productivity of greater than about 500 mg/$L_{broth}$/hr of isoprene. In some aspects, the cells have an average volumetric productivity greater than about 1,000 mg/$L_{broth}$/hr of isoprene. In some aspects, the cells have an average volumetric productivity greater than about 1,500 mg/$L_{broth}$/hr of isoprene. In some aspects, the cells have an average volumetric productivity greater than about 2,000 mg/$L_{broth}$/hr of isoprene. In some aspects, the cells have an average volumetric productivity between about 500 mg/$L_{broth}$/hr and about 2,000 mg/$L_{broth}$/hr of isoprene.

In some aspects, the method further comprises the steps of sterilizing the collected permeate and recycling it back into the same fermentor or into another fermentor, wherein the cells cultured in the presence of recycled permeate have greater average specific productivity of isoprene than the same cells cultured in the absence of recycled permeate. In some aspects, the cells have about two times the average specific productivity of isoprene than the same cells cultured in the absence of recycled permeate. In some aspects, the cells have about three times the average specific productivity of isoprene than the same cells cultured in the absence of recycled permeate. In some aspects, the portion of the culture is removed continuously. In some aspects, the portion of the culture is removed discontinuously.

In some aspects, the isoprene synthase polypeptide is a plant isoprene synthase polypeptide. In some aspects, the cells further comprise a heterologous nucleic acid encoding an IDI polypeptide. In some aspects, the cells further comprise a chromosomal copy of an endogenous nucleic acid encoding an IDI polypeptide. In some aspects, the cells further comprise a heterologous nucleic acid encoding a DXS polypeptide, in some aspects, the cells further comprise a chromosomal copy of an endogenous nucleic acid encoding a DXS polypeptide. In some aspects, the cells further comprise one or more nucleic acids encoding an DI polypeptide and a DXS polypeptide. In some aspects, one nucleic acid encodes the isoprene synthase polypeptide, IDI polypeptide, and DXS polypeptide. In some aspects, one plasmid encodes the isoprene synthase polypeptide, IDI polypeptide, and DXS polypeptide. In some aspects, the cells further comprise a heterologous nucleic acid encoding an MVA pathway polypeptide. In some aspects, the MVA pathway polypeptide is a mevalonate kinase (MVK) polypeptide. In some aspects, the MVK polypeptide is from the genus *Methanosarcina*. In some aspects, the MVK is from *Methanosarcina mazei*. In some aspects, the isoprene synthase polypeptide is a naturally-occurring polypeptide from the genus *Pueraria*. In some aspects, the isoprene synthase polypeptide is a naturally-occurring polypeptide from *Pueraria montana*. In some aspects, the isoprene synthase polypeptide is a naturally-occurring polypeptide from the genus *Populus*. In some aspects, the isoprene synthase polypeptide is a naturally-occurring polypeptide from *Populus alba*. In some aspects, the cells further comprise a heterologous nucleic acid encoding an MVA pathway polypeptide. In some aspects, the MVA pathway polypeptide, is a mevalonate kinase (MVK) polypeptide. In some aspects, the MVK polypeptide is from the genus *Methanosarcina*. In some aspects, the MVK polypeptide is from *Methanosarcina mazei*. In some aspects, the cells are bacterial cells.

In some aspects, the cells are gram-positive bacterial cells. In some aspects, the cells are *Bacillus* cells. In some aspects, the cells are *Bacillus subtilis* cells. In some aspects, the cells are gram-negative bacterial cells. In some aspects, the cells are *Escherichia* or *Pantoea* cells. In some aspects, the cells are *Escherichia coli* or *Pantoea citrea* cells. In some aspects, the cells are fungal cells. In some aspects, the cells are *Trichoderma* cells, in some aspects, the cells are *Trichoderma reesei* cells. In some aspects, the cells are yeast cells. In some aspects, the cells are *Yarrowia* cells. In some aspects, the cells are *Yarrowia lipolytica* cells.

In some aspects, the cells comprise (i) an integrated nucleic acid encoding the lower MVA pathway from *S. cerevisiae* comprising a glucose isomerase promoter and a nucleic acid encoding mevalonate kinase (MVK); a nucleic acid encoding phosphomevalonate kinase (PMK); a nucleic acid encoding diphosphomevalonate decarboxylase (MVD); and a nucleic acid encoding isopentenyl diphosphate isomerase (IDI); (ii) a nucleic acid encoding *P. alba* isoprene: synthase; (iii) a nucleic acid encoding *M. mazei* mevalonate kinase; and (iv) a nucleic acid encoding the upper MVA pathway from *Enterococcus faecalis*, comprising a nucleic acid encoding an acetoacetyl-Coenzyme A synthase (thiolase) polypeptide; a nucleic acid encoding a 3-hydroxy-3-methylglutaryl-Coenzyme A synthase polypeptide; and a nucleic acid encoding a 3-hydroxy-3-methylglutaryl-Coenzyme A reductase polypeptide.

BRIEF DESCRIPTION OF THE DRAWINGS

FIG. 3A-B are the nucleotide sequence of plasmid pET24 *P. alba* HGS (SEQ ID NO:1).

FIGS. 6A-B are the nucleotide sequence of plasmid EWL230 (SEQ ID NO:2).

FIGS. 9A-B are the nucleotide sequence of plasmid EWL244 (SEQ ID NO:3).

FIGS. 10B-C are the nucleotide sequence of the *M. mazei* archaeal Lower Pathway operon (SEQ ID NO:4).

FIGS. 11B-C are the nucleotide sequence of MCM376-MVK from *M. mazei* archaeal Lower in pET200D (SEQ ID NO:5).

FIGS. 13A-B are the nucleotide sequence of plasmid pRBRCMPCI1.5-pgl (SEQ ID NO:6).

FIG. 14A shows the time course of optical density within the 15-L bioreactor fed with glucose. FIG. 14B shows the time course of isoprene titer within the 15-L bioreactor fed with glucose. The titer is defined as the amount of isoprene produced per liter of fermentation broth. Method for calculating isoprene: cumulative isoprene produced in 59 hrs, g/Fermentor volume at 59 hrs, L [=] g/L broth. FIG. 14C also shows the time course of isoprene titer within the 15-L bioreactor fed with glucose. Method for calculating isoprene: ∫(instantaneous isoprene production rate, g/L/hr)dt from t=0 to 59 hours [=] g/L broth. FIG. 14D shows the time course of total isoprene produced from the 15-L bioreactor fed with glucose. FIG. 14E shows volumetric productivity within the 15-L bioreactor fed with glucose. FIG. 14F shows carbon dioxide evolution rate (CER), or metabolic activity profile, within the 15-L bioreactor fed with glucose.

FIG. 19A shows a map of plasmid pDW34, encoding a truncated version of P. alba isoprene synthase (MEA variant) under the control of the PTrc promoter and M. mazei MVK. FIG. 19B-D shows the complete nucleotide sequence of plasmid pDW34 (SEQ ID NO:7).

DETAILED DESCRIPTION OF THE INVENTION

Figure 1A:
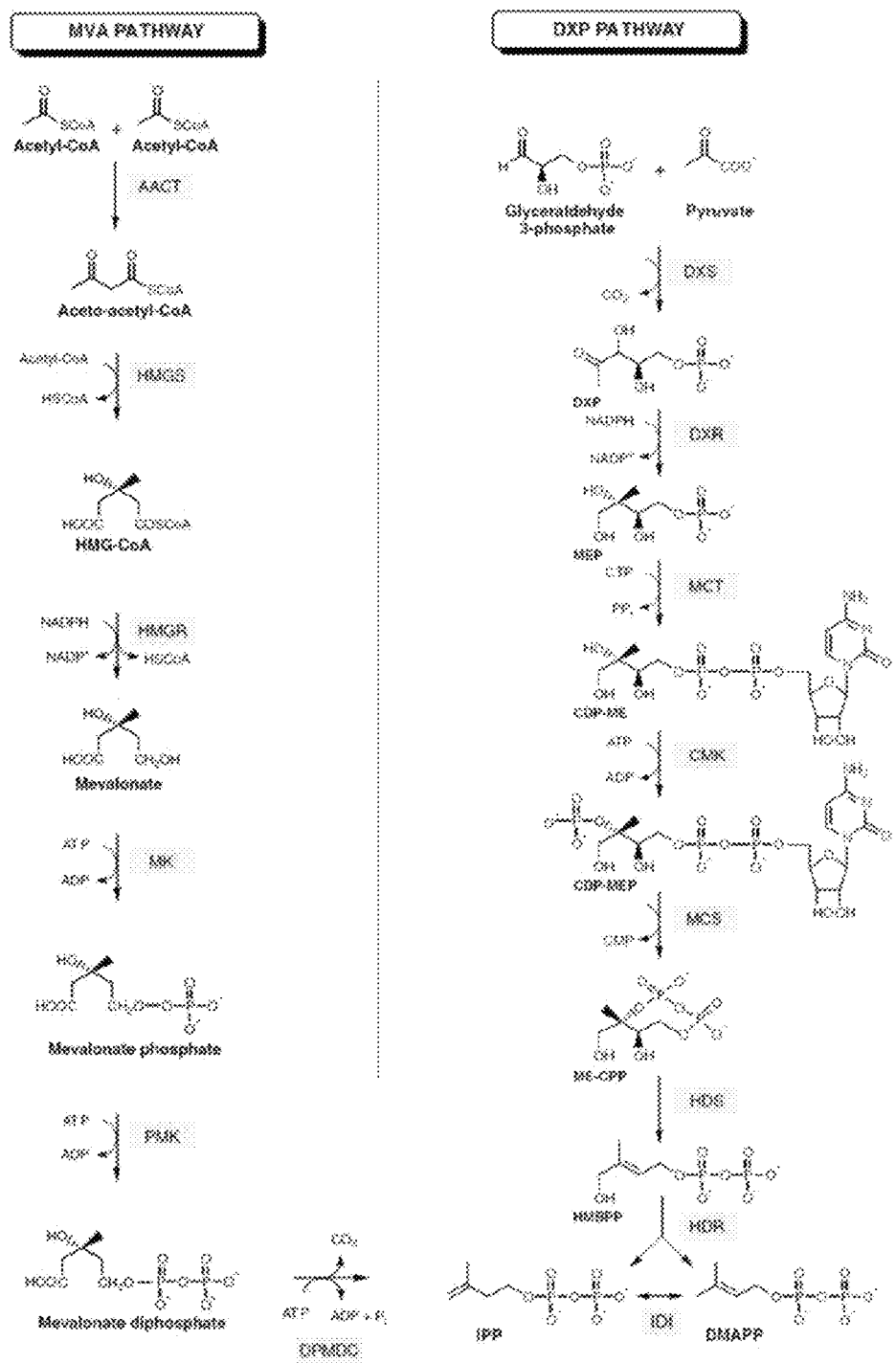
FIG. 1A shows the MVA and DXP metabolic pathways for isoprene (based on F. Bouvier et al., Progress in Lipid Res. 44:357-429, 2005). The following description includes alternative names for each polypeptide in the pathways and a reference that discloses an assay for measuring the activity of the indicated polypeptide (each of these references are each hereby incorporated herein by reference in their entireties). Mevalonate Pathway: AACT; Acetyl-CoA acetyltransferase, MvaE, EC 2.3.1.9. Assay: J. Bacteriol. 184:2116-2122, 2002; HMGS; Hydroxymethylglutaryl-CoA synthase, MvaS, EC 2.3.3.10. Assay: J. Bacteriol, 184:4065-4070, 2002; HMGR; 3-Hydroxy-3-methylglutaryl-CoA reductase, MvaE, EC 1.1.1.34. Assay: J. Bacteriol. 184:2116-2122, 2002; MVK; Mevalonate kinase, ERG12, EC 2.7.1.36. Assay: Curr Genet. 19:9-14, 1991, PMK; Phosphomevalonate kinase, ERG8, EC 2.7.4.2. Assay: Mol. Cell. Biol. 11:620-631, 1991; DPMDC; Diphosphomevalonate decarboxylase, MVD1, EC 4.1.1.33. Assay: Biochemistry 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay; PNAS 97: 6451-6456, 2000; CMK; 4-Diphosphocytidyl-2-C-methyl-D-erythritol kinase, IspE, EC 2.7.1.148. Assay: PNAS 97:1062-1067, 2000; MCS; 2C-Methyl-D-erythritol 2,4-cyclodiphosphate synthase, IspF, EC 4.6.1.12. Assay: PNAS 96:11758-11763, 1999; LIDS; 1-Hydroxy-2-methyl-2-(E)-butenyl. 4-diphosphate synthase, ispG, EC 1.17.4.3. Assay: J. Org. Chem. 70:9168-9174, 2005; HDR; 1-Hydroxy-2-methyl-2-(E)-butenyl 4-diphosphate reductase, IspH, EC 1.17.12. Assay: JACS 126:12847-12855, 2004.

A membrane bioreactor (MBR) can enhance fermentative production of isoprene gas by combining fermentation with recycling of select broth components that would otherwise be discarded. An MBR includes a liquid fermentation bioreactor culturing isoprene-producing cells operated in conjunction with a membrane filter, such as a crossflow filter or a tangential flow filter. The MBR filters fermentation broth and returns the non-permeating component (filter "retentate") to the reactor, effectively increasing reactor concentration of cells, cell debris and other broth solids, while maintaining specific productivity of the cells. This substantially improves titer, total production, and volumetric productivity of isoprene, leading to lower capital and operating costs.

The liquid filtrate ("permeate") is not returned to the reactor and thus provides a beneficial reduction in reactor volume, similar to collecting a broth draw-off. However, unlike a broth draw-off, the collected permeate is a clarified liquid that can be easily sterilized by filtration after storage in an ordinary vessel. Thus, the permeate can be readily reused as a nutrient and/or water recycle source, further reducing operating costs. A permeate, which contains soluble "spent medium," may be added to the same or another fermentation to enhance isoprene production.

The MBR is a potentially scalable and advantageous mode of the methods of producing isoprene from renewable resources described elsewhere (see, e.g., International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716). Besides providing a significantly higher isoprene titer than otherwise possible and increasing volumetric productivity, the MBR produces a clarified permeate which may be used as a nutrient and as a water source, thereby reducing raw material consumption and improving process sustainability.

Accordingly, in one aspect, provided herein are improved methods of producing isoprene comprising: (a) culturing cells comprising a heterologous nucleic acid encoding an isoprene synthase polypeptide under suitable culture conditions for the production of isoprene, wherein the cells either (i) produce isoprene at a titer greater than 40 g/L or (ii) have an average volumetric productivity of isoprene greater than about 500 mg/$L_{broth}$/hr of isoprene; (b) removing a portion of the culture; (c) filtering the removed portion of the culture to produce a permeate and a retentate; (d) returning the retentate to the culture; (e) producing isoprene; and optionally (f) recovering the isoprene; wherein the cultured cells undergoing steps (b), (c), and (d) either (i) produce isoprene at a higher titer, or (ii) have greater average volumetric productivity of isoprene than the same cells cultured without undergoing steps (b), (c), and (d).

In another aspect, provided herein are improved methods of producing isoprene comprising: (a) culturing cells comprising a heterologous nucleic acid encoding an isoprene synthase polypeptide in a fermentor containing growth medium under suitable culture conditions for the production of isoprene, wherein the cells either (i) produce isoprene at a titer greater than 40 g/L or (ii) have an average volumetric productivity of isoprene greater than about 500 mg/$L_{broth}$/hr of isoprene; (b) removing a portion of the cell culture from the fermentor; (c) transferring the removed portion of the cell culture to a filter; (d) filtering the removed portion of the cell culture to form: (i) a permeate comprising spent growth medium; and (ii) a retentate comprising cells and other culture solids; (e) returning the retentate to the fermentor; (f) collecting the permeate; (g) producing isoprene; and (h) recovering the isoprene; wherein the cultured cells undergoing steps (b), (c), (d) and (e) either (i) produce isoprene at a higher titer, or (ii) have greater average volumetric productivity of isoprene than the same cells cultured without undergoing steps (b), (c), (d), and (e).

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "Molecular Cloning; A Laboratory Manual", second edition (Sambrook et al., 1989); "Oligonucleotide Synthesis" (M. 3. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994). Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Genetically engineered cell cultures in bioreactors have produced isoprene more efficiently, in larger quantities, in higher purities and/or with unique impurity profiles, e.g., as described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Definitions

The term "isoprene" refers to 2-methyl-1,3-butadiene (CAS#78-79-5). Isoprene can be the direct and final volatile C5 hydrocarbon product from the elimination of pyrophosphate from 3,3-dimethylallyl pyrophosphate (DMAPP). In some cases, it may not involve the linking or polymerization of an IPP molecule(s) to a DMAPP molecule(s). The term "isoprene" is not generally intended to be limited to its method of production unless indicated otherwise herein.

As used herein, "biologically produced isoprene" or "bioisoprene" isoprene produced by any biological means, such as produced by genetically engineered cell cultures, natural microbials, plants or animals. A bioisoprene composition usually contains fewer hydrocarbon impurities than isoprene produced from petrochemical sources and often requires minimal treatment in order to be of polymerization grade. A bioisoprene composition also has a different impurity profile from a petrochemically produced isoprene composition.

As used herein, the term "permeate" refers to filtrate (i.e., spent growth medium) produced by filtering the contents of a fermentor or bioreactor containing growth medium and cells (i.e., containing cultured cells), for example, by crossflow filtration. The cells can be any of the exemplary isoprene-producing cells or cell types described herein, including, for example, those that comprise one or more heterologous nucleic acids encoding an isoprene synthase polypeptide, a DXS polypeptide, an IDI polypeptide, and/or an MVA pathway polypeptide operably linked to a promoter.

As used herein, the term "retentate" refers to solids retained on a filter (i.e., cells, debris and other culture, solids) after filtering the contents of a fermentor or bioreactor containing growth medium and cells (i.e., containing cultured cells), for example, by crossflow filtration. The cells can be any of the exemplary isoprene-producing cells or cell types described herein, including, for example, those that comprise one or more heterologous nucleic acids encoding an isoprene synthase polypeptide, a DXS polypeptide, an IDI polypeptide, and/or an MVA pathway polypeptide operably linked to a promoter.

As used herein, the terms "polypeptide" and "polypeptides" include polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide. An isolated polypeptide can be a non-naturally occurring polypeptide.

By "heterologous polypeptide" is meant a polypeptide whose amino acid sequence is not identical to that of another polypeptide naturally expressed in the same host cell. In particular, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic c acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In some cases a recombinant nucleic acid is a nucleic acid that encodes a non-naturally occurring polypeptide.

By "heterologous nucleic acid" is meant a nucleic acid whose nucleic acid sequence is not identical to that of another nucleic acid naturally found in the same host cell. In particular, a heterologous nucleic acid is not identical to a wild-type nucleic c acid that is found in the same host cell in nature.

As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

The term "selective marker" or "selectable marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, cerbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4.

Unless defined otherwise herein, all technical and scientific terms used herein have the same meaning as commonly understood by one of ordinary skill in the art to which this invention pertains. Although any methods and materials similar or equivalent to those described herein find use in the practice, of the present invention, the preferred methods and materials are described herein. Accordingly, the terms defined immediately below are more fully described by reference to the Specification as a whole. All documents cited are, in relevant part, incorporated herein by reference in their entirety. However, the citation of any document is not to be construed as an admission that it is prior art with respect to the present invention.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Methods for the Increased Production of Bioisoprene

Provided herein are improved methods of producing isoprene. In some aspects, the improved methods comprise (a) culturing cells comprising a heterologous nucleic acid encoding an isoprene synthase under culture conditions suitable for the production of isoprene, wherein the cells either (i) produce isoprene at a titer greater than 40 g/L or (ii) have an average volumetric productivity greater than about 500 mg/$L_{broth}$/hr of isoprene; (b) removing a portion of the culture; (c) filtering the removed portion of the culture to produce a permeate and a retentate; (d) returning the retentate to the culture; (e) producing isoprene; and optionally (f) recovering the isoprene; wherein the cultured cells undergoing steps (b), (c), and (d) either (i) produce isoprene at a higher titer, or (ii) have greater average volumetric productivity of isoprene than the same cells cultured without undergoing steps (b), (c), and (d). In some aspects, the cells are cultured in a fermentor, bioreactor, or other vessel suitable for commercial scale cell culture. In some aspects, the fermentor, bioreactor, or cell culture vessel is stainless steel, glass or copper. In some aspects, the fermentor, bioreactor, or cell culture vessel further comprises an isoprene collection outlet connected to an isoprene storage tank. In some aspects, the isoprene collection outlet further comprises a valve to control the flow of isoprene through the isoprene collection outlet.

In some aspects, the improved methods comprise (a) culturing cells comprising a heterologous nucleic acid encoding an isoprene synthase in a fermenter containing growth medium under culture conditions suitable for the production of isoprene, wherein the cells either (i) produce isoprene at a titer greater than 40 g/L or (ii) have an average volumetric productivity greater than about 500 mg/$L_{broth}$/hr of isoprene; (b) removing a portion of the cell culture from the fermentor; (c) transferring the removed portion of the cell culture to a filter; (d) filtering the removed portion of the cell culture to form; (i) a permeate comprising spent growth medium; and (ii) a retentate comprising cells and other culture solids; (e) returning the retentate to the fermentor; (f) collecting the permeate; (g) producing isoprene; and optionally (h) recovering the isoprene; wherein the cultured cells undergoing steps (b), (c), (d) and (e) either (i) produce isoprene at a higher titer, or (ii) have greater average volumetric productivity of isoprene than the same cells cultured without undergoing steps (b), (c), (d) and (e), in some aspects, the cells are cultured in a fermentor, bioreactor, or other vessel suitable for commercial scale cell culture. In some aspects, the fermentor, bioreactor, or cell culture vessel is stainless steel, glass or copper. In some aspects, the fermentor, bioreactor, or cell culture vessel further comprises an isoprene collection outlet connected to an isoprene storage tank. In some aspects, the isoprene collection outlet further comprises a valve to control the flow of isoprene through the isoprene collection outlet. In some aspects, the isoprene collection outlet comprises any suitable flexible tubing or rigid tubing described herein.

In some aspects, the fermentor, bioreactor, or cell culture vessel is connected to the filter by a circulation loop and a circulation pump. In some aspects, the circulation loop further comprises one or more valves to control the flow of material (i.e., of a portion of the cell culture or of the retentate) through the circulation loop. Generally, any type of pump having the ability to precisely regulate or control flow rate and pressure can be used with the methods described herein. In some aspects, the circulation pump comprises a positive displacement pump, such as a peristaltic pump, a reciprocating pump, or a rotary pump. In some aspects, the circulation pump is a peristaltic pump. In some aspects, the circulation pump is a velocity pump, such as a centrifugal pump, a radial flow pump, an axial flow pump, a mixed flow pump, or a gravity pump. In some aspects, the circulation pump is a centrifugal pump.

In some aspects, the circulation loop comprises flexible tubing. In some aspects, the flexible tubing is polyvinyl chloride (PVC), polyurethane (e.g., Super thane silicone (e.g., Silicon®), thermoplastic rubber (TPR; e.g., Suprene®), fluoropolymer, polyethylene, polypropylene (e.g., Prolite®), latex or metal tubing. In some aspects, the PVC tubing is braid reinforced (e.g., Nylobrade®), steel wire reinforced (e.g., Vardex®), or spiral reinforced (e.g., Newflex®). In some aspects, the polyurethane tubing is braid-reinforced (e.g., Urebrade® Pneumatic). In some aspects, the silicone tubing is braid reinforced (e.g., Silbrade®), platinum-cured medical grade tubing (e.g., Silicon® Med-X), or polyester and wire reinforced (e.g., Silvac®). In some aspects, the fluoropolymer tubing is polytetrafluoroethylene (PTFE; e.g., CONTEF™), fluorinated ethylene propylene (FEP; Coiltef™), perfluoroalkoxy (PFA; e.g., Coiltef™), ethylene tetrafluoroethylene (ETFE), ethylene chloro-trifluoroethylene (ECTFE), polyvinylidene fluoride (PDF) polyetherimide (PEI), or polyetheretherketone (PEEK). In some aspects, the polyethylene tubing is linear low density polyethylene tubing (LLDPE; e.g., Zelite™).

In some aspects, the circulation loop comprises rigid tubing or pipe. In some aspects, the rigid tubing is metal. In some aspects, the metal is carbon steel, stainless steel, galvanized steel, copper, brass, or any other suitable metal or alloy. In some aspects, the rigid tubing is plastic. In some aspects, the plastic is polyvinyl chloride (PVC), chlorinated polyvinyl chloride (CPVC), fiber reinforced plastic (FRP), reinforced polymer mortar (RPMP), polypropylene (PP), polyethylene (PE), cross-linked high density polyethylene (PEX), polybutylene (PB), high density polyurethane, acrylonitrile butadiene styrene (ABS), or any other suitable material.

In some aspects, the permeate is collected from the filter by a permeate collection outlet and a permeate pump and stored in a permeate collection tank. In some aspects, the permeate collection outlet further comprises a valve to control the flow of permeate through the permeate collection outlet. In some aspects, the permeate collection outlet comprises any suitable flexible tubing or rigid tubing described herein. In some aspects, the permeate collection outlet further comprises a permeate pressure gauge to monitor the pressure in the permeate collection outlet ($P_{perm}$). Generally, any type of pump having the ability to precisely regulate or control flow rate and pressure can be used with the methods described herein, in some aspects, the permeate pump comprises a positive displacement pump, such as a peristaltic pump, a reciprocating pump, or a rotary pump. In some aspects, the permeate pump is a peristaltic pump. In some aspects, the permeate pump is a velocity pump, such as a centrifugal pump, a radial flow pump, an axial flow pump, a mixed flow pump, or a gravity pump. In some aspects, the permeate pump is a centrifugal pump. In some aspects, the permeate collection tank further comprises a vent to relieve pressure within the tank.

In some aspects, the improved method further comprises a step of recycling, the permeate back into the same cell culture or into another culture. Recycling the permeate can allow for increased production of isoprene over a period of time, for example, more isoprene made per per hour. Accordingly, in one aspect, the cells cultured in the presence of recycled permeate have greater average specific productivity of isoprene than the same cells cultured in the absence of recycled permeate. In some aspects, the cells have about two times the average specific productivity of isoprene than the same cells cultured in the absence of recycled permeate. In some aspects, the cells have about three times the average specific productivity of isoprene than the same cells cultured in the absence of recycled permeate. In some aspects, the permeate is sterilized before being recycled back into the same cell culture or into another cell culture. In some aspects, the permeate is sterilized by filtration. In some aspects, the permeate is sterilized by autoclaving. In some aspects, the permeate is sterilized by ultraviolet or gamma irradiation. In some aspects, the permeate is not sterilized before being recycled back into the same cell culture or into another cell culture.

One advantage of this system described herein is that a minimal amount of the desired product (i.e., isoprene) is lost through the recycling or discarding of the permeate. In one aspect, at least about 50% of the isoprene that is produced in the fermentor before the circulation commences is recoverable after the circulation has been completed and thus is not lost in the recycling or discarding of permeate. In another aspect, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, at least about 99.5%, at least about 99.6%, at least about 99.7%, at least about 99.8%, or at least about 99.9% of the isoprene produced in the fermentor is recoverable and not lost in the permeate.

In some aspects, the circulation loop further comprises an inlet pressure gauge to monitor the inlet pressure ($P_{in}$) of the filter. In some aspects, the circulation loop further comprises an outlet gauge to monitor the outlet pressure ($P_{out}$) of the filter. In some aspects, the circulation loop further comprises an inlet pressure gauge to monitor the inlet pressure ($P_{in}$) of the filter and an outlet gauge to monitor the outlet pressure ($P_{out}$) of the filter. In some aspects, the improved method further comprises the steps of: (i) monitoring the inlet pressure of the filter with an inlet pressure gauge ($P_{in}$); (ii) monitoring the outlet pressure of the filter with an outlet pressure gauge ($P_{out}$); and (iii) monitoring the pressure in the permeate collection outlet with a permeate pressure gauge ($P_{perm}$) to determine the transmembrane pressure across the filter.

In some aspects, the filtering is by microfiltration. In some aspects, the microfiltering is by crossflow filtration. In some aspects, the filtering is by ultrafiltration. In some aspects, the ultrafiltering is by crossflow filtration. In crossflow filtration, the solution to be filtered is passed tangentially across the filter membrane at positive transmembrane pressure (TMP) relative to the permeate side. A proportion of the material which is smaller than the membrane pore size passes through the membrane as filtrate (i.e., permeate), while the rest of the solution remains on the feed side of the membrane as retentate. With crossflow filtration, the tangential motion of the bulk of the fluid across the membrane causes trapped particles or solids left on the filter surface to be rubbed off, so a crossflow filter can operate continuously at relatively high solids loads without folding. In addition, the retentate remains in the form of a mobile slurry, suitable for returning to the fermentor via the circulation loop. In some aspects, the filtering is by centrifugation or spin-filtration. In some aspects, the filtering is by vortex-flow filtration. In some aspects, the filtering is by hydrocyclone. In any of the aspects described herein, the filtration is by microfiltration. In any of the aspects described herein, the filtration is by ultrafiltration.

In some aspects, the filtering is by microfiltration. In some aspects, the microfiltration is crossflow filtration. In some aspects, the crossflow filtration is tangential flow filtration. In some aspects, the tangential flow filter comprises a membrane configuration selected from the group consisting of a hollow fiber membrane, a spiral wound membrane, a tubular membrane, or a plate-frame membrane. In some aspects, the tangential flow filter comprises a hollow fiber membrane. In some aspects, the hollow fiber membrane, the spiral wound membrane, the tubular membrane, or the plate-frame membrane comprises a polyethersulfone, (PES) membrane, a polysulfone (PS) membrane, a polyvinylidene, difluoride (PVDF) membrane, a polyarylsulfone membrane, a polyamide, membrane, a polypropylene membrane, a polyethylene membrane, a polytetrafluoroethylene (PTFE) membrane, a cellulose acetate membrane, a polyacrylonitrile membrane, a vinyl copolymer membrane, a cellulose membrane, a regenerated cellulose membrane, a polycarbonate membrane, a ceramic membrane, a steel membrane, or a stainless steel membrane.

The pore size of a microfiltration membrane, such as a tangential flow membrane, can vary depending on the membrane material and application. Any of the membrane configurations and membrane types described herein can have filter pore sizes in various ranges.

In some aspects, the tangential flow filter has a filter pore size suitable for use with any of the exemplary isoprene-producing cells or cell types described herein, including, for example, those that comprise one or more heterologous nucleic acids encoding an isoprene synthase polypeptide, a DXS polypeptide, an IDI polypeptide and/or an MVA pathway polypeptide operably linked to a promoter. In some aspects, the tangential flow filter has a filter pore size between about 0.005 µm and about 100 µm. In some aspects, the tangential flow filter has a filter pore size between about 0.005 µm and about 50 µmm. In some aspects, the tangential flow filter has a filter pore size between about 0.005 µm and about 10 µm, in some aspects, the tangential flow filter has a filter pore size between about 0.005 µm and about 5 µm. In some aspects, the tangential flow filter has a filter pore size between about 0.005 µm and about 2 µm. In some aspects, the tangential flow filter has a filter pore size between about 0.005 µm and about 1 µm. In some aspects, the tangential flow filter has a filter pore size between about 0.05 µm and about 100 µm. In some aspects, the tangential flow filter has a filter pore size between about 0.05 µm and about 50 µm. In some aspects, the tangential flow filter has a filter pore size between about 0.05 µm and about 10 µm. In some aspects, the tangential flow filter has a filter pore size between about 0.0.5 µm and about 5 µm. In some aspects, the tangential flow filter has a filter pore size between about 0.05 µm and about 2 µm. In some aspects, the tangential flow filter has a filter pore size between about 0.05 µm and about 1 µm. In some aspects, the tangential flow filter has a filter pore size between about 0.5 µm and about 100 µm. In some aspects, the tangential flow filter has a filter pore size between about 0.5 µm and about 50 µm. In some aspects, the tangential flow filter has a filter pore size between about 0.5 µm and about 10 µm. In some aspects, the tangential flow filter has a filter pore size between about 0.5 µm and about 5 µm. In some aspects, the tangential flow filter has a filter pore size between about 0.5 µm and about 2 µm. In some aspects, the tangential flow filter has a filter pore size between about 0.5 µm and 1 µm. In some aspects, the tangential flow filter has a filter pore size between about 1 µm and about 10 µm. In some aspects, the tangential flow filter has a filter pore size between about 1 µm and about 50 µm. In some aspects, the tangential flow filter has a filter pore size between about 1 µm and about 100 µm. In some aspects, the tangential flow filter has a filter pore size between about 5 µm and about 10 µm. In some aspects, the tangential flow filter has a filter pore size between about 5 µm and about 50 µm. In some aspects, the tangential flow filter has a filter pore size between about 5 µm and about 100 µm. In some aspects, the tangential flow filter has a filter pore size between about 0.05 µm and about 0.5 µm. In some aspects, the tangential flow filter has a filter pore size between about 0.5 µm and about 1 µm. In some aspects, the tangential flow filter has a filter pore size between about 1 µm and about 5 µm. In some aspects, the tangential flow filter has a filter pore size between about 5 microns and about 10 microns. In some aspects, the tangential flow filter has a filter pore size between about 10 microns and about 50 microns. In some aspects, the tangential flow filter has a filter pore size between about 10 microns and about 100 microns.

In some aspects, the filtering is by ultrafiltration. In some aspects, the ultrafiltration is crossflow filtration. In some aspects, the crossflow filtration is tangential flow filtration. In some aspects, the tangential flow filter comprises a membrane configuration selected from the group consisting of a hollow fiber membrane, a spiral wound membrane, a tubular membrane, or a plate-frame membrane. In some aspects, the tangential flow filter comprises a hollow fiber membrane. In some aspects, the hollow fiber membrane, the spiral wound membrane the tubular membrane, or the plate-frame membrane comprises a polyethersulfone, (PES) membrane, a polysulfone (PS) membrane, a polyvinylidene difluoride (PVDF) membrane, a polyarylsulfone membrane, a polyamide membrane, a polypropylene membrane, a polyethylene membrane, a polytetrafluoroethylene (PTFE) membrane, a cellulose acetate membrane, a polyacrylonitrile membrane, a vinyl copolymer membrane, a cellulose membrane, a regenerated cellulose membrane, a polycarbonate membrane, a ceramic membrane, a steel membrane, or a stainless steel membrane.

The nominal molecular weight cutoff (NMWC) of an ultrafiltration membrane, such as a tangential flow membrane, can vary depending on the membrane material and application. Any of the membrane configurations and membrane types described herein can have NMWCs in various ranges.

In some aspects, the tangential flow filter has a nominal molecular weight cutoff (NMWC) suitable for use with any of the exemplary isoprene-producing cells or cell types described herein, including, for example, those that comprise one or more heterologous nucleic acids encoding an isoprene synthase polypeptide, a DXS polypeptide, an IDI polypeptide, DXP pathway polypeptide and/or an MVA pathway polypeptide operably linked to a promoter. In some aspects the tangential flow filter has an NMWC between 1000 and 750,000. In some aspects, the tangential flow filter has an NMWC greater than 1000. In some aspects, the tangential flow filter has an NMWC greater than 5000. In some aspects, the tangential flow filter has an NMWC greater than 10,000. In some aspects, the tangential flow filter has an NMWC greater than 15,000. In some aspects, the tangential flow filter has an NMWC greater than 20,000. In some aspects, the tangential flow filter has an NMWC greater than 25,000. In some aspects, the tangential flow filter has an NMWC greater than 50,000. In some aspects, the tangential flow filter has an NMWC greater than 75,000. In some aspects, the tangential flow filter has an NMWC greater than 100,000. In some aspects, the tangential flow filter has an NMWC greater than 150,000. In some aspects, the tangential flow filter has an NMWC greater than 200,000. In some aspects, the tangential flow filter has an NMWC greater than 250,000. In some aspects, the tangential flow filter has an NMWC greater than 300,000. In some aspects, the tangential flow filter has an NMWC greater than 350,000. In some aspects, the tangential flow filter has an NMWC greater than 400,000. In some aspects, the tangential flow filter has an NMWC greater than 450,000. In some aspects, the tangential flow filter has an NMWC greater than 500,000. In some aspects, the tangential flow filter has an NMWC greater than 600,000. In some aspects, the tangential flow filter has an NMWC greater than 750,000.

In some aspects, the tangential flow filter is a GE Healthcare Xampler™ Ultrafiltration Cartridge (GE Healthcare Bio-Sciences, Corp., Piscataway, N.J.) having a 500,000 nominal molecular weight cutoff (NMWC), comprising a hollow fiber membrane having a 1 mm inner diameter. In some aspects, the tangential flow filter is an OPTISEP® 3000 filter module (NCSRT, Inc., Apex, N.C.), an OPTISEP® 7000 filter module, or an OPTISEP® 11000 filter module using a filter having a molecular weight cutoff suitable for use with any of the exemplary isoprene-producing cells or cell types described herein, including, for example, those that comprise one or more heterologous nucleic acids encoding an isoprene synthase polypeptide, a DXS polypeptide, an IDI polypeptide, and/or an MVA pathway polypeptide operably linked to a promoter.

In some aspects, the filter is a tangential flow filter has a nominal molecular weight cutoff (NMWC) suitable for use with any of the exemplary isoprene-producing cells or cell types described herein, including, for example, those that comprise one or more heterologous nucleic acids encoding an isoprene synthase polypeptide, a DXS polypeptide, an IDI polypeptide, a DXP pathway polypeptide and/or an MVA pathway polypeptide operably linked to a promoter. In some aspects the tangential flow filter has an NMWC between 1000 and 750,000. In some aspects the tangential flow filter has an NMWC between 10,000 and 750,000. In some aspects the tangential flow filter has an NMWC between 100,000 and 750,000. In some aspects the tangential flow filter has an NMWC between 250,000 and 750,000. In some aspects, the tangential flow filter has an NMWC greater than 1000. In some aspects, the tangential flow filter has an NMWC greater than 5000. In some aspects, the tangential flow filter has an NMWC greater than 10,000. In some aspects, the tangential flow filter has an NMWC greater than 15,000. In some aspects, the tangential flow filter has an NMWC greater than 20,000. In some aspects, the tangential flow filter has an NMWC greater than 25,000. In some aspects, the tangential flow filter has an NMWC greater than 50,000. In some aspects, the tangential flow filter has an NMWC greater than 75,000. In some aspects, the tangential flow filter has an NMWC greater than 100,000. In some aspects, the tangential flow filter has an NMWC greater than 150,000. In some aspects, the tangential flow filter has an NMWC greater than 200,000. In some aspects, the tangential flow filter has an NMWC, greater than 250,000, in some aspects, the tangential flow filter has an NMWC greater than 300,000. In some aspects, the tangential flow filter has an NMWC greater than 350,000. In some aspects, the tangential flow filter has an NMWC greater than 400,000. In some aspects, the tangential flow filter has an NMWC greater than 450,000. In some aspects, the tangential flow filter has an NMWC greater than 500,000. In some aspects, the tangential flow filter has an NMWC greater than 600,000. In some aspects, the tangential flow filter has an NMWC greater than 750,000.

In some aspects, the fermentor, bioreactor, or cell culture vessel lacks a circulation loop and a circulation pump, and the filtering is by a submerged membrane bioreactor. In some aspects, the submerged membrane bioreactor comprises a filtration module immersed in the cell culture within the fermentor, bioreactor, or cell culture vessel. In some aspects, the filtration module comprises a filter and a permeate side in fluid contact with the cell culture only through the filter. In some aspects, the filter comprises a comprises a polyethersulfone (PES) membrane, a polysulfone (PS) membrane, a polyvinylidene difluoride (PVDF) membrane, a polyarylsulfone membrane, a polyamide membrane, a polypropylene membrane, a polyethylene membrane, a polytetrafluoroethylene (PTFE) membrane, a cellulose acetate membrane, a polyacrylonitrile membrane, a vinyl copolymer membrane a cellulose membrane, a regenerated cellulose membrane, a polycarbonate membrane, a ceramic membrane, a steel membrane, or a stainless steel membrane.

In some aspects, the filter in the submerged membrane bioreactor is an ultrafilter having a nominal molecular weight cutoff (NMWC) suitable for use with any of the exemplary isoprene-producing cells or cell types described herein, including, for example, those that comprise one or more heterologous nucleic acids encoding an isoprene synthase polypeptide, a DXS polypeptide, an IDI polypeptide and/or an MVA pathway polypeptide operably linked to a promoter. In some aspects the filter has an NMWC between 1000 and 750,000. In some aspects, the filter has an NMWC greater than 1000. In some aspects, the filter has an NMWC, greater than 5000. In some aspects, the filter has an NMWC greater than 10,000. In some aspects, the filter has an NMWC greater than 15,000. In some aspects, the filter has an NMWC greater than 20,000. In some aspects, the filter has an NMWC greater than 25,000. In some aspects, the filter has an NMWC greater than 50,000. In some aspects, the filter has an NMWC greater than 75,000. In some aspects, the filter has an NMWC greater than 100,000. In some aspects, the filter has an NMWC greater than 150,000. In some aspects, the filter has an NMWC greater than 200,000. In some aspects, the filter has an NMWC greater than 250,000. In some aspects, the filter has an NMWC greater than 300,000. In some aspects, the filter has an NMWC greater than 350,000. In some aspects, the filter has an NMWC greater than 400,000. In some aspects, the filter has an NMWC greater than 450,000. In some aspects, the filter has an NMWC greater than 500,000. In some aspects, the filter has an NMWC greater than 600,000. In some aspects, the filter has an NMWC greater than 750,000.

In some aspects, the filter in the submerged membrane bioreactor is a microfilter having a filter pore size suitable for use with any of the exemplary isoprene-producing cells or cell types described herein, including, for example, those that comprise one or more heterologous nucleic acids encoding an isoprene synthase polypeptide, a DXS polypeptide, an MI polypeptide, a DXP pathway polypeptide and/or an MVA pathway polypeptide operably linked to a promoter. In some aspects, the filter has a filter pore size between about 0.005 μm and about 100 μm. In some aspects, the filter has a filter pore size between about 0.005 μm and about 50 μm. In some aspects, the filter has a filter pore size between about 0.005 μm and about 10 μm. In some aspects, the filter has a filter pore size between about 0.005 μm and about 5 μm. In some aspects, the filter has a filter pore size between about 0.005 μm and about 2 μm. In some aspects, the filter has a filter pore size between about 0.005 μm and about 1 μm. In some aspects, the filter has a filter pore size between about 0.05 μm and about 100 μm. In some aspects, the filter has a filter pore size between about 0.05 μm and about 50 μm. In some aspects, the filter has a filter pore size between about 0.05 μm and about 10 μm. In some aspects, the filter has a filter pore size between about 0.05 μm and about 5 μm. In some aspects, the filter has a filter pore size between about 0.05 μm and about 2 μm. In some aspects, the filter has a filter pore size between about 0.05 μm and about 1 μm. In some aspects, the filter has a filter pore size between about 0.5 µm and about 100 µm. In some aspects, the filter has a filter pore size between about 0.5 µm and about 50 µm. In some aspects, the filter has a filter pore size between about 0.5 µm and about 10 µm. In some aspects, the filter has a filter pore size between about 0.5 µm and about 5 µm. In some aspects, the tangential flow filter has a filter pore size between about 0.5 µm and about 2 µm. In some aspects, the filter has a filter pore size between about 0.5 µm and 1 µm. In some aspects, the filter has a filter pore size between about 1 µm and about 10 µm. In some aspects, the filter has a filter pore size between about 1 µm and about 50 µm. In some aspects, the filter has a filter pore size between about 1 µm and about 100 µm. In some aspects, the filter has a filter pore size between about 5 µm and about 10 µm. In some aspects, the filter has a filter pore size between about 5 µm and about 50 µm. In some aspects, the filter has a filter pore size between about 5 µm and about 100 µm. In some aspects, the filter has a filter pore size between about 0.05 µm and about 0.5 µm. In some aspects, the filter has a filter pore size between about 0.5 µm and about 1 µm. In some aspects, the filter has a filter pore size between about 1 µm and about 5 µm. In some aspects, the filter has a filter pore size between about 5 microns and about 10 microns. In some aspects, the filter has a filter pore size between about 10 microns and about 50 microns. In some aspects, the filter has a filter pore size between about 10 microns and about 100 microns.

In some aspects, the filtration module further comprises a permeate collection outlet and a permeate pump. In some aspects, the filtration module further comprises a permeate collection tank. In some aspects, the permeate pump comprises a positive displacement pump, such as a peristaltic pump, a reciprocating pump, or a rotary pump. In some aspects, the permeate pump is a peristaltic pump. In some aspects, the permeate pump is a velocity pump, such as a centrifugal pump, a radial flow pump, an axial flow pump, a mixed flow pump, or a gravity pump. In some aspects, the permeate pump is a centrifugal pump. In some aspects, the permeate collection tank further comprises a vent to relieve pressure within the tank.

In some aspects, the improved method further comprises the step of maintaining a positive transmembrane pressure, calculated as follows: TMP=$([P_{in}+P_{out}]/2)-P_{perm}$. In some aspects, the improved method further comprises the step of cleaning the filter by inverting the TMP (i.e., making the TMP negative). Inverting the TMP causes the permeate to flow back into the solution to be filtered, thereby lifting any solids fouling the filter off the surface of the membrane and improving flow through the filter and the circulation loop, Inverting the TMP usually requires pressurizing the permeate side of the membrane. Inverting the TMP is more commonly applied to ceramic and steel membrane filters, which are less susceptible to damage due to their intrinsic strength. Pressurization of the permeate may be achieved by connecting the permeate line to compressed air or water, among other methods. See, for example, Danisco application WO 2009/035700 for exemplary teachings on specific ways to invert TMP in a spiral-wound polymeric membrane In some aspects, the residence time within the filtration unit is 25 seconds and the glucose concentration within the fermentation broth is between 3 and 25 g/L. In some aspects, the residence time within the filtration unit is 10 seconds and the glucose concentration within the fermentation broth is between 1 and 3 g/L. In some aspects, the residence time within the filtration unit is between 5 and 60 seconds and the glucose concentration within the fermentation broth is between 0.2 and 25 g/L.

In some aspects, removal of a portion of the culture first begins when the culture reaches a target volume. In some aspects, the target volume is determined empirically. In some aspects, the target volume is ½ (one-half), ⅓ (one-third), ¼ (one-quarter), ⅕ (one-fifth), ⅙ (one-sixth), ⅐ (one-seventh), ⅛ (one-eighth), ⅑ (one ninth), ⅒ (one tenth), or less of the total volume of the fermentor, bioreactor, or cell culture vessel. In some aspects, the target volume is the working capacity of the fermentor, bioreactor, or cell culture vessel being used to culture the cells. In some aspects, removal of a portion of the culture first begins at 5 hours, 10 hours, 15 hours, 20 hours, 25 hours, 30 hours, 35 hours, or more after the start of cell culture (i.e., after the start of fermentation).

Continuous operation of the circulation loop costs energy (pumping against pressure) and adds stress to the cells. Thus, the option of delaying or suspending filtration, i.e. harvesting spent media at particular times during the fermentation or at intervals instead of continuously, may provide economic benefit as well as potentially improve fermentation outcome. In some aspects, the portion of the culture is removed continuously from the fermentor, bioreactor, or cell culture vessel. In some aspects, the portion of the culture is continuously removed at a rate of 1 ml/minute, 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 100 ml/minute, 250 ml/minute, 500 ml/minute, 1000 ml/minute or more. In some aspects, the portion of the culture is continuously removed at a rate of 1 ml/15 minutes, 5 ml/15 minutes, 10 ml/15 minutes, 15 ml/15 minutes, 20 ml/15 minutes, 25 ml/15 minutes, 30 ml/15 minutes, 35 ml/15 minutes, 40 ml/15 minutes, 45 ml/15 minutes, 50 ml/15 minutes, 100 ml/15 minutes. 250 ml/15 minutes. 500 ml/15 minutes. 1000 ml/15 minutes or more. In some aspects, the portion of the culture is continuously removed at a rate of 1 ml/30 minutes, 5 ml/30 minutes, 10 ml/30 minutes, 15 ml/30 minutes, 20 ml/30 minutes, 25 ml/30 minutes, 30 ml/30 minutes, 35 ml/30 minutes, 40 ml/30 minutes, 45 ml/30 minutes, 50 ml/30 minutes, 100 ml/30 minutes, 250 ml/30 minutes, 500 ml/30 minutes, 1000 ml/30 minutes or more. In some aspects, the portion of the culture is continuously removed at a rate of 1 ml/60 minutes, 5 ml/60 minutes, 10 ml/60 minutes, 15 ml/60 minutes, 20 mil/60 minutes, 25 ml/60 minutes, 30 ml/60 minutes, 35 ml/60 minutes, 40 ml/60 minutes, 45 ml/60 minutes, 50 ml/60 minutes, 100 ml/60 minutes, 250 ml/60 minutes, 500 ml/60 minutes, 1000 ml/60 minutes or more. In some aspects, the portion of the culture is continuously removed at a rate of 1 g/minute, 2 g/minute, 3 g/minute, 4 g/minute, 5 g/minute, 6 g/minute, 7 g/minute; 8 g/minute, 9 g/minute, 10 g/minute, 20 g/minute, 30 g/minute, 40 g/minute, 50 g/minute, 60 g/minute, 70 g/minute, 80 g/minute, 90 g/minute, 100 g/minute or more. In some aspects, the portion of the culture is continuously removed at a rate of 1 g/15 minutes, 2 g/15 minutes, 3 g/15 minutes, 4 g/15 minutes, 5 g/15 minutes, 6 g/15 minutes, 7 g/15 minutes, 8 g/15 minutes, 9 g/15 minutes, 10 g/15 minutes, 20 g/15 minutes, 30 g/15 minutes, 40 g/15 minutes, 50 g/15 minutes, 60 g/15 minutes, 70 g/15 minutes, 80 g/15 minutes, 90 g/15 minutes, 100 g/15 minutes or more. In some aspects, the portion of the culture is continuously removed at a rate of 1 g/30 minutes, 2 g/30 minutes, 3 g/30 minutes, 4 g/30 minutes, 5 g/30 minutes, 6 g/3 minutes, 7 g/30 minutes, 8 g/30 minutes, 9 g/30 minutes, 10 g/30 minutes, 20 g/30 minutes, 30 g/30 minutes, 40 g/30 minutes, 50 g/30 minutes, 60 g/30 minutes, 70 g/30 minutes, 80 g/30 minutes, 90 g/30 minutes, 100 g/30 minutes or more. In some aspects, the portion of the culture is continuously removed at a rate of 1 g/60 minutes, 2 g/60 minutes, 3 g/60 minutes, 4 g/60 minutes, 5 g/60 minutes, 6 g/60 minutes, 7 g/60 minutes, 8 g/60 minutes, 9 g/60 minutes, 10 g/60 minutes, 20 g/60 minutes, 30 g/60 minutes, 40 g/60 minutes, 50 g/60 minutes, 60 g/60 minutes, 70 g/60 minutes, 80 g/60 minutes, 90 g/60 minutes, 100 g/60 minutes or more. In some aspects, the portion of the culture is continuously removed at a rate of 0.2 kg/minute, 0.4 kg/minute, 0.6 kg/minute, 0.8 kg/minute, 1.0 kg/minute, 1.2 kg/minute, 1.4 kg/minute, 1.6 kg/minute, 1.8 kg/minute, 2.0 kg/minute, 3.0 kg/minute, 4.0 kg/minute, 5.0 kg/minute or more. In some aspects, the portion of the culture is continuously removed at a rate of 0.2 kg/15 minutes, 0.4 kg/15 minutes, 0.6 kg/15 minutes, 0.8 kg/15 minutes, 1.0 kg/15 minutes, 1.2 kg/15 minutes, 1.4 kg/15 minutes, 1.6 kg/15 minutes, 1.8 kg/15 minutes, 2.0 kg/15 minutes, 3.0 kg/15 minutes, 4.0 kg/15 minutes, 5.0 kg/15 minutes or more. In some aspects, the portion of the culture is continuously removed at a rate of 0.2 kg/30 minutes, 0.4 kg/30 minutes, 0.6 kg/30 minutes, 0.8 kg/30 minutes, 1.0 kg/30 minutes, 1.2 kg/30 minutes, 1.4 kg/30 minutes, 1.6 kg/30 minutes, 1.8 kg/30 minutes, 2.0 kg/30 minutes, 3.0 kg/30 minutes, 4.0 kg/30 minutes, 5.0 kg/30 minutes or more. In some aspects, the portion of the culture is continuously removed at a rate of 0.2 kg/60 minutes, 0.4 kg/60 minutes, 0.6 kg/60 minutes, 0.8 kg/60 minutes, 1.0 kg/60 minutes, 1.2 kg/60 minutes, 1.4 kg/60 minutes, 1.6 kg/60 minutes, 1.8 kg/60 minutes, 2.0 kg/60 minutes, 3.0 kg/60 minutes, 4.0 kg/60 minutes, 5.0 kg/60 minutes or more.

In some aspects, the portion of the culture is removed discontinuously from the fermenter, bioreactor, or cell culture vessel, at a desired time interval. In some aspects, a portion of the culture is removed from the fermenter, bioreactor, or cell culture vessel, every 5 minutes, every 10 minutes, every 15 minutes, every 20 minutes, every 25 minutes, every 30 minutes, every 35 minutes, every 40 minutes, every 45 minutes, every 50 minutes, every 55 minutes, every 60 minutes, or more. In some aspects, 1 ml, 5 ml, 10 ml, 15 ml, 20 ml, 25 ml, 30 ml, 35 ml, 40 ml, 45 ml, 50 ml, 75 ml, 100 ml, 125 ml, 150 ml, 175 ml, 200 ml, 225 ml, 250 ml, or more is removed from the culture at each interval. In some aspects, 0.2 kg, 0.4 kg, 0.6 kg, 0.8 kg, 1.0 kg, 1.2 kg, 1.4 kg, 1.6 kg, 1.8 kg, 2.0 kg, or more is removed from the culture at each interval.

In some aspects, the cells cultured in any of the improved methods described herein are any of the isoprene-producing cells described herein that comprise one or more heterologous nucleic acids encoding an isoprene synthase polypeptide, a DXS polypeptide, an IDI polypeptide, a DXP pathway polypeptide and/or an MVA pathway polypeptide operably linked to a promoter. In some aspects, the cells comprising a heterologous nucleic acid encoding an isoprene synthase either (i) produce isoprene at a titer greater than 40 g/L, or (ii) have an average volumetric productivity greater than about 500 mg/$L_{broth}$/hr of isoprene.

In some aspects, the DXP pathway polypeptide is selected from the group consisting of DXS (1-deoxy-D-xylulose-5-phosphate synthase), EAR (1-deoxy-D-xylulose-5-phosphate reductoisomerase), MCT (4-diphosphocytidyl-2C-methyl-D-erythritol synthase), CMK (4-diphosphocytidyl-2-C-methyl-D-erythritol kinase), MCS (2C-methyl-D-erythritol 2,4-cyclodiphosphate synthase), HDS (1-hydroxy-2-methyl-2-(E)-butenyl 4-diphosphate synthase), HDR (1-hydroxy-2-methyl-2-(E)-butenyl 4-diphosphate reductase), and IDI polypeptides.

In some aspects, the MVA pathway polypeptide is an upper MVA pathway polypeptide. In some aspects, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some aspects, the upper MVA pathway polypeptide is from the genus *Enterococcus*. In some aspects, the upper MVA pathway polypeptide is from *Enterococcus faecalis*. In some aspects, the upper MVA pathway polypeptide comprises an acetoacetyl-Coenzyme A synthase (thiolase) polypeptide, a 3-hydroxy-3-methylglutaryl-Coenzyme A reductase polypeptide and a 3-hydroxy-3-methylglutaryl-Coenzyme A synthase polypeptide from *Enterococcus faecalis*.

In some aspects, the MVA pathway polypeptide is a lower MVA pathway polypeptide. In some aspects, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (DI). In some aspects, the lower MVA pathway polypeptide is from the genus *Methanosarcina*. In some aspects, the lower MVA pathway polypeptide is from *Methanosarcina mazei*. In some aspects, the lower MVA pathway polypeptide comprises an MVK polypeptide from *Methanosarcina mazei*. In some aspects, the lower MVA pathway polypeptide comprises an MVK polypeptide, a PMK polypeptide, an MVD polypeptide, and an IDI polypeptide from *Saccharomyces cerevisiae*. In some aspects, the lower MVA polypeptide comprises an MVK polypeptide from *Methanosarcina mazei* and an MVK polypeptide, a PMK polypeptide, an MVD polypeptide, and an IDI polypeptide from *Saccharomyces cerevisiae*.

In some aspects, the isoprene synthase polypeptide is a naturally-occurring polypeptide from the genus *Pueraria*. In some aspects, the isoprene synthase polypeptide is a naturally-occurring polypeptide from *Pueraria montana*. In some aspects, the isoprene synthase polypeptide is a naturally-occurring polypeptide from the genus *Populus*. In some aspects, the isoprene synthase polypeptide is a naturally-occurring polypeptide from *Populus alba*.

In some aspects, the upper MVA pathway polypeptide comprises an acetoacetyl-Coenzyme A synthase (thiolase) polypeptide, a 3-hydroxy-3-methylglutaryl-Coenzyme A reductase polypeptide and a 3-hydroxy-3-methylglutaryl-Coenzyme A synthase polypeptide from *Enterococcus faecalis*; the lower MVA polypeptide comprises an MVK polypeptide from *Methanosarcina mazei* and an MVK polypeptide, a PMK polypeptide, an MVD polypeptide, and an IDI polypeptide from *Saccharomyces cerevisiae*; and the isoprene synthase polypeptide is from *Populus alba*.

In some aspects, the cells produce isoprene at a titer of greater than about 40 g/L. In some aspects, the cells produce isoprene at a titer of greater than about 50 g/L. In some aspects, the cells produce isoprene at a titer of greater than about 60 g/L. In some aspects, the cells produce isoprene at a titer of greater than about 70 g/L. In some aspects, the cells produce isoprene at a titer of greater than about 80 g/L. In some aspects, the cells produce isoprene at a titer of greater than about 90 g/L. In some aspects, the cells produce isoprene at a titer of greater than about 100 g/L. In some aspects, the cells produce isoprene at a titer of greater than about 110 g/L. In some aspects, the cells produce isoprene at a titer of greater than about 120 g/L. In some aspects, the cells produce isoprene at a titer of greater than about 130 g/L. In some aspects, the cells produce isoprene at a titer of greater than about 140 g/L. In some aspects, the cells produce isoprene at a titer of greater than about 150 g/L. In some aspects, the cells produce isoprene at a titer of greater than about 160 g/L. In some aspects, the cells produce isoprene at a titer of greater than about 170 g/L. In some aspects, the cells produce isoprene at a titer of greater than about 180 g/L. In some aspects, the cells produce isoprene at a titer of greater than about 190 g/L. In some aspects, the cells produce isoprene at a titer of greater than about 200 g/L. In some aspects, the cells produce isoprene at a titer between about 40 g/L and about 100 g/L. In some aspects, the cells produce isoprene at a titer between about 60 g/L and about 100 g/L. In some aspects, the cells produce isoprene at a titer between about 60 g/L and about 120 g/L. In some aspects, the cells produce isoprene at a titer between about 40 g/L and about 150 g/L. In some aspects, the cells produce isoprene at a titer between about 40 g/L and about 200 g/L. In some aspects, the cells produce isoprene at a titer between about 80 g/L and about 150 g/L. In some aspects, the cells produce isoprene at a titer between about 100 g/L and about 150 g/L. In some aspects, the cells produce isoprene at a titer between about 100 g/L and about 180 g/L. In some aspects, the cells produce isoprene at a titer between about 100 g/L, and about 200 g/L. In some aspects, the cells produce isoprene at a titer between about 120 g/L and about 200 g/L. In some aspects, the cells have an average volumetric productivity of greater than about 500 mg/$L_{broth}$/hr of isoprene. In some aspects, the cells have an average volumetric productivity greater than about 1,000 mg/$L_{broth}$/hr of isoprene. In some aspects, the cells have an average volumetric productivity greater than about 1,500 mg/$L_{broth}$/hr of isoprene. In some aspects, the cells have an average volumetric productivity greater than about 2,000 mg/$L_{broth}$/hr of isoprene. In some aspects, the cells have an average volumetric productivity between about 500 mg/$L_{broth}$/hr and about 2,000 mg/$L_{broth}$/hr of isoprene.

In some aspects, the isoprene synthase polypeptide is a plant isoprene synthase polypeptide. In some aspects, the cells further comprise a heterologous nucleic acid encoding an IDI polypeptide. In some aspects, the cells further comprise a chromosomal copy of an endogenous nucleic acid encoding an IDI polypeptide. In some aspects, the cells further comprise a heterologous nucleic acid encoding a DXS polypeptide. In some aspects, the cells further comprise a heterologous nucleic acid encoding a DXP pathway polypeptide. In some aspects, the cells further comprise a chromosomal copy of an endogenous nucleic acid encoding a DXS polypeptide. In some aspects, the cells further comprise one or more nucleic acids encoding an IDI polypeptide and a DXS polypeptide or a DXP pathway polypeptide. In some aspects, one nucleic acid encodes the isoprene synthase polypeptide, IDI polypeptide, and DXS polypeptide or a DXP pathway polypeptide. In some aspects, one plasmid encodes the isoprene synthase polypeptide, III polypeptide, and DXS polypeptide or a TAP pathway polypeptide. In some aspects, the cells further comprise a heterologous nucleic acid encoding an MVA pathway polypeptide. In some aspects, the cells further comprise a chromosomal copy of an endogenous nucleic acid encoding an MVA pathway polypeptide. In some aspects, the MVA pathway polypeptide is a mevalonate kinase (MVK). In some aspects, the MVK is a polypeptide from the genus *Methanosarcina*. In some aspects, the MVK is a polypeptide from *Methanosarcina mazei*.

In some aspects, the isoprene synthase polypeptide is a naturally-occurring polypeptide from the genus *Pueraria*. In some aspects, the isoprene synthase polypeptide is a naturally-occurring polypeptide from *Pueraria montana*. In some aspects, the isoprene synthase polypeptide is a naturally-occurring polypeptide from the genus *Populus*. In some aspects, the isoprene synthase polypeptide is a naturally-occurring polypeptide from *Populus alba*. In some aspects, the cells further comprise a heterologous nucleic acid encoding an MVA pathway polypeptide. In some aspects, the MVA pathway polypeptide, is a mevalonate kinase (MVK). In some aspects, the MVK is a polypeptide from the genus *Metha-nosarcina*. In some aspects, the MVK is a polypeptide from *Methanosarcina mazei*. In some aspects, the cells are bacterial cells. In some aspects, the cells are gram-positive bacterial cells. In some aspects, the cells are *Bacillus* cells. In some aspects, the cells are *Bacillus subtilis* cells. In some aspects, the cells are gram-negative bacterial cells. In some aspects, the cells are *Escherichia* or *Pantoea* cells. In some aspects, the cells are *Escherichia coli* or *Pantoea citrea* cells. In some aspects, the cells are fungal cells. In some aspects, the cells are *Trichoderma* cells. In some aspects, the cells are *Trichoderma reesei* cells. In some aspects, the cells are yeast cells. In some aspects, the cells are *Yarrowia* cells. In some aspects, the cells are *Yarrowia lipolytica* cells.

Exemplary Methods for Isolating Nucleic Acids

Isoprene synthase, DXS, IDI, DXP pathway polypeptides, MVA pathway polypeptides, PGL, hydrogenase, hydrogenase maturation and/or transcription factor nucleic acids can be isolated using standard methods. Methods of obtaining desired nucleic acids from a source organism of interest (such as a bacterial genome) are common and well known in the art of molecular biology (see, for example, WO 2004/033646 and references cited therein). Standard methods of isolating nucleic acids, including PCR amplification of known sequences, synthesis of nucleic acids, screening of genomic libraries, screening of cosmid libraries are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716).

Exemplary Promoters and Vectors

Any of the isoprene synthase, DXS, DXP pathway polypeptides, IDI, MVA pathway polypeptides, PGL, hydrogenase, hydrogenase maturation and/or transcription factor nucleic acids described herein can be included in one or more vectors. Accordingly, also described herein are vectors with one more nucleic acids encoding any of the isoprene synthase, DXS. IDI, DXP pathway polypeptides, MVA pathway polypeptides, PGL, hydrogenase, hydrogenase maturation and/or transcription factor polypeptides that are described herein. In some aspects, the vector contains a nucleic acid under the control of an expression control sequence. In some aspects, the expression control sequence is a native expression control sequence. In some aspects, the expression control sequence is a non-native expression control sequence. In some aspects, the vector contains a selective marker or selectable marker. In some aspects, an isoprene synthase, DXS, IDI, DXP pathway, MVA pathway, PGL, hydrogenase, hydrogenase maturation, or transcription regulatory nucleic acid integrates into a chromosome of the cells without a selectable marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Suitable vectors can be maintained in low, medium, or high copy number in the host cell. Protocols for obtaining and using such vectors are known to those in the art (see, for example, Sambrook et al., Molecular Cloning: A Laboratory Manual, $2^{nd}$ ed., Cold Spring Harbor, 1989). Suitable vectors compatible with the cells and methods described herein are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716).

Promoters are well known in the art. Any promoter that functions in the host cell can be used for expression of an isoprene synthase, DXS, DXP pathway, IDI, MVA pathway, PGL, hydrogenase, hydrogenase maturation and/or transcription factor nucleic acid in the host cell. Initiation control regions or promoters, which are useful to drive expression of isoprene synthase, DXS, DXP pathway, IDI, MVA pathway, PGL, hydrogenase, hydrogenase maturation and/or transcription factor nucleic acids in various host cells are numerous and familiar to those skilled in the art (see, for example, WO 2004/033646 and references cited therein). Virtually any promoter capable of driving these nucleic acids can be used including a glucose isomerase promoter (see, for example, U.S. Pat. No. 7,132,527 and references cited therein). Suitable promoters compatible with the cells and methods described herein are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716).

In some aspects, the expression vector also includes a termination sequence. Termination control regions may also be derived from various genes native to the host cell. In some aspects, the termination sequence and the promoter sequence are derived from the same source. Suitable termination sequences compatible with the cells and methods described herein are described in International Publication No. WO 2009/076676 A2 and U.S. patent application Ser. No. 12/335, 071, both of which are incorporated herein by reference.

An isoprene synthase, DXP pathway, IDI, MVA pathway, PGL, hydrogenase, hydrogenase maturation and/or transcription factor nucleic acid can be incorporated into a vector, such as an expression vector, using standard techniques (Sambrook et al., Molecular Cloning: A Laboratory Manual, Cold Spring Harbor, 1982). Suitable techniques compatible with the cells and methods described herein are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716).

In some aspects, it may be desirable to over-express isoprene synthase, DXP pathway polypeptides, IDI, MVA pathway polypeptides, PGL, hydrogenase, hydrogenase maturation and/or transcription factor nucleic acids at levels far higher than currently found in naturally-occurring cells. In some aspects, it may be desirable to under-express (e.g., mutate, inactivate, or delete) isoprene synthase, DXP pathway polypeptides, IDI, MVA pathway polypeptides, PGL, hydrogenase, hydrogenase maturation, or transcription factor polypeptide-encoding nucleic acids at levels far below that those currently found in naturally-occurring cells. Suitable methods for over- or under-expressing the isoprene synthase, DXP pathway polypeptides, IDI, MVA pathway polypeptides, PGL, hydrogenase, hydrogenase maturation and/or transcription factor nucleic acids compatible with cells and methods described herein are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716).

Exemplary Source Organisms

Figure 1B:
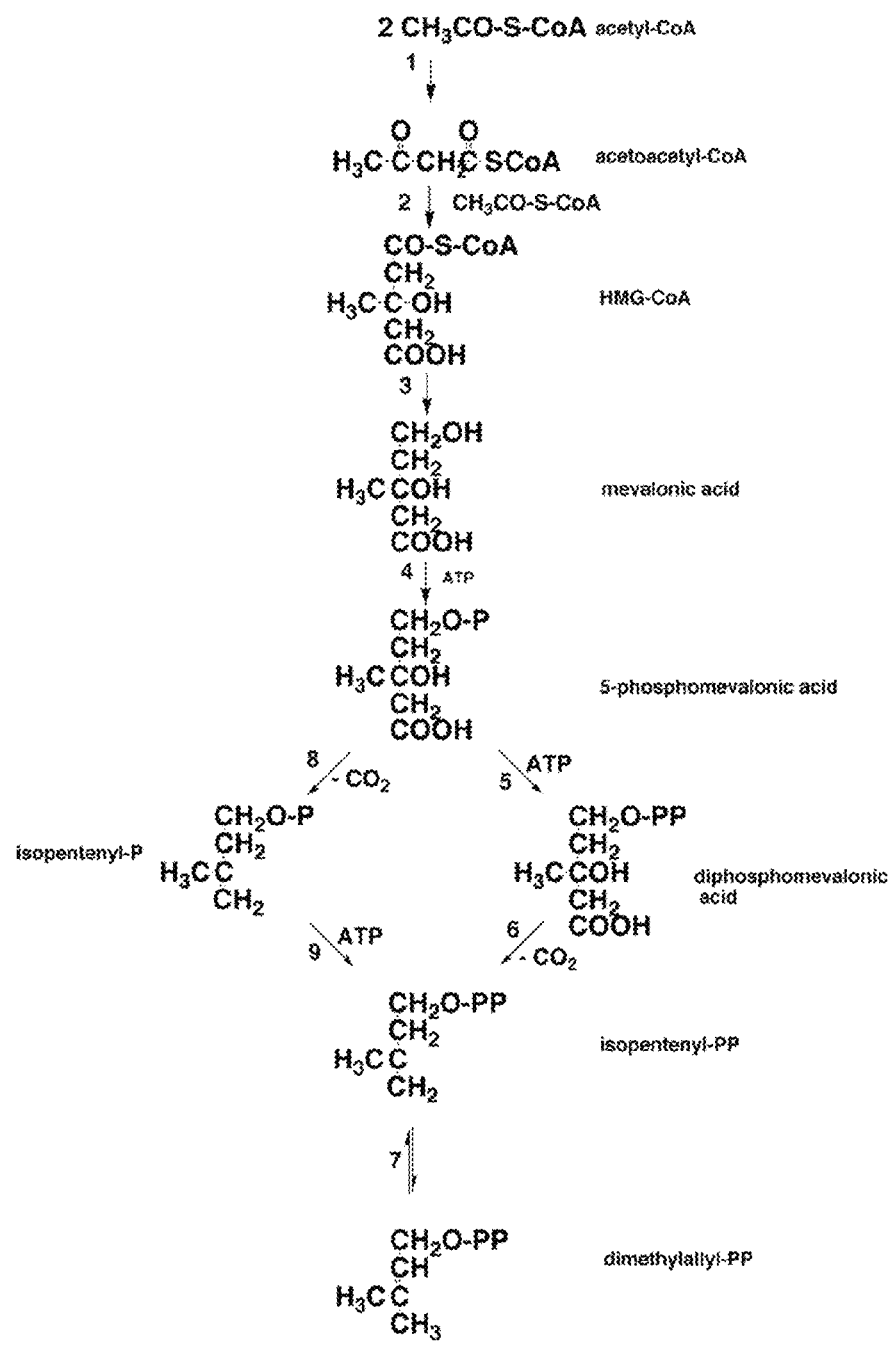
FIG. 1B illustrates the classical and modified MVA pathways. 1, acetyl-CoA acetyltransferase (AACT); 2, HMG-CoA synthase (HMGS); 3, HMG-CoA reductase (HMGR); 4, mevalonate kinase (MV K); 5, phosphomevalonate kinase (PMK); 6, diphosphomevalonate decarboxylase (MVD or DPMDC); 7, isopentenyl diphosphate isomerase (MI); 8, phosphomevalonate decarboxylase (PMDC); 9, isopentenyl phosphate kinase (IPK) The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology Reviews* 71:97-120, 2007, which is incorporated herein by reference in its entirety, particular with respect to nucleic acids and polypeptides of the modified MVA pathway. The modified MVA pathway is present, for example, in some archaeal organisms, such as *Methanosarcina mazei*.

Isoprene synthase, DXP pathway, IDI, MVA pathway, PGL, hydrogenase, hydrogenase maturation and/or transcription factor nucleic acids (and their encoded polypeptides) can be obtained from any organism that naturally contains isoprene synthase, DXP pathway, IDI, MVA pathway, PGL, hydrogenase, hydrogenase maturation and/or transcription factor nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIGS. 1A and 1B). Thus, DXP pathway nucleic acids can be obtained, e.g., from any organism that contains the DXP pathway or contains both the MVA and DXP pathways, IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways. Hydrogenase, nucleic acids can be obtained, e.g., from any organism that oxidizes hydrogen or reduces hydrogen ions. Fermentation side product genes can be obtained or identified, e.g., from any organism that undergoes oxygen-limited or anaerobic respiration, such as glycolysis.

The nucleic acid sequence of the isoprene synthase, DXP pathway, IDI, MVA pathway, PGL, hydrogenase, hydrogenase maturation and/or transcription factor nucleic acids can be isolated from a bacterium, fungus, plant, algae, or cyanobacterium. Exemplary source organisms include, for example, yeasts, such as species *Saccharomyces* (e.g., *S. cerevisiae*) or species of *Yarrowia* (e.g., *Yarrowia lipolytica*), other fungi, such as species of *Trichoderma* (e.g., *T. reesei*), bacteria, such as species of *Bacillus* (e.g., *B. subtilis*), species of *Escherichia* (e.g., *E. coli*), species of *Methanosarcina* (e.g., *Methanosarcina mazei*) or species of *Pantoea* (e.g., *P. citrea*), plants, such as kudzu or poplar (e.g., *Populus alba x tremula* CAC35696) or aspen (e.g., *Populus tremuloides*). Exemplary host organisms are described in U.S. Provisional Patent Application No. 61/187,959, International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary Host Cells

A variety of host cells can be used to express isoprene synthase, DXS, IDI, DXP pathway polypeptides, MVA pathway polypeptides, hydrogenase, hydrogenase maturation and/or transcription factor polypeptides and to co-produce isoprene and hydrogen in the methods described herein. Exemplary host cells include cells from any of the organisms listed in the prior section under the heading "Exemplary Source Organisms." The host cell may be a cell that naturally produces isoprene or a cell that does not naturally produce isoprene. In some aspects, the host cell naturally produces isoprene using the DXP pathway, and an isoprene synthase, DXS, and/or IDI nucleic acid is added to enhance production of isoprene using this pathway. In some aspects, the host cell naturally produces isoprene using the MVA pathway, and an isoprene synthase and/or one or more MVA pathway nucleic acids are added to enhance production of isoprene using this pathway. In some aspects, the host cell naturally produces isoprene using the DXP pathway and one or more MVA pathway nucleic acids are added to produce isoprene using part or all of the MVA pathway as well as the DXP pathway. In some aspects, the host cell naturally produces isoprene using both the DXP and MVA pathways and one or more isoprene synthase, DXS, IDI, or MVA pathway nucleic acids are added to enhance production of isoprene by one or both of these pathways.

Various types of host cells suitable for use with the methods described herein, including cells that naturally produce isoprene using both the DXP and MVA pathways, are discussed in International Publication No. WO 2009/076676, U.S. patent application Ser. No. 12/335,071 (US Publ. No, 2009/02031021, WO 2010/003007, US Publ. No. 2010/0048964, WO 2009/132220, and US Publ. No. 2010/0003716. Non-limiting host cells include: *Escherichia coli (E. coli) Panteoa citrea, Bacillus subtilis, Yarrowia lipolytica*, and *Trichoderma reesei*.

Exemplary Transformation Methods

Isoprene synthase, DXS, IDI, MVA pathway, PGL, hydrogenase, hydrogenase maturation and/or transcription factor nucleic acids or vectors containing them can be inserted into a host cell (e.g., a plant cell, a fungal cell, a yeast cell, or a bacterial cell described herein) using standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds.) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989). The introduced nucleic acids may be integrated into chromosomal DNA or maintained as extrachromosomal replicating sequences. Transformants can be selected by any method known in the art. Suitable methods for selecting transformants are described in U.S. Provisional Patent Application No. 61/187,959, International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary Cell Culture Media

By "cells in culture" is meant two or more cells in a solution (e.g., a cell growth medium) that allows the cells to undergo one or more cell divisions. "Cells in culture" do not include plant cells that are part of a living, multicellular plant containing cells that have differentiated into plant tissues. In various aspects, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

Various carbon sources suitable for culturing isoprene producing cells according to the methods described herein are described in International Application Publication WO 2009/076676 A2 and in U.S. patent application Ser. No. 12/335,071, both of which are incorporated herein by reference in their entireties.

In some aspects, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63.1298-1306, 1997). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate, carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein). In some aspects where an isoprene synthase, DXS, IDI, and/or MVA pathway nucleic acid is under the control of an inducible promoter, the inducing agent e.g., a sugar, metal salt or antimicrobial), is desirably added to the medium at a concentration effective to induce expression of an isoprene synthase, DXS, IDI, DXP pathway polypeptides and/or MVA pathway polypeptides. In some aspects, cell medium has an antibiotic (such as kanamycin) that corresponds to the antibiotic resistance nucleic acid (such as a kanamycin resistance nucleic acid) on a vector that has one or more isoprene synthase, DXS, IDI, DXP pathway nucleic acids or MVA pathway nucleic acids, Exemplary Cell Culture Conditions Materials and methods suitable for the maintenance and growth of bacterial cultures are well known in the art. Exemplary techniques may be found in *Manual of Methods for General Bacteriology* Gerhardt et al., eds.), American Society for Microbiology, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of one or more isoprene synthase, DXS, IDI, DXP pathway polypeptides or MVA pathway polypeptides encoded by a nucleic acid inserted into the host cells.

Standard cell culture conditions are suitable for culturing the cells (see, for example, WO 2004/033646 and references cited therein). Cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, e.g., cultures are cultured at approximately 28° C. in appropriate medium in shake cultures or fermentors until the desired amount of isoprene and hydrogen co-production is achieved. In some aspects, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells.

Standard culture conditions and modes of fermentation, such as batch, fed-batch, or continuous fermentation, are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716. Batch and Fed-Batch fermentations are common and well known in the art and examples may be found in Brock, Biotechnology, *A Textbook of Industrial Microbiology*, Second Edition (1989) Sinauer Associates, Inc.

In some aspects, a constitutive or leaky promoter (such as a Trc promoter) is used and a compound (such as IPTG) is not added to induce expression of the isoprene synthase, DXS, IDI, DXP pathway nucleic acids) or MVA pathway nucleic acid(s) operably linked to the promoter. In some aspects, a compound (such as IPTG) is added to induce expression of the isoprene synthase, DXS, IDI, DXP pathway nucleic acids) or MVA pathway nucleic acid(s) operably linked to the promoter.

Exemplary Isoprene Synthase Polypeptides and Nucleic Acids

In some aspects, the *E. coli* cells comprise a heterologous nucleic acid encoding an isoprene synthase polypeptide. In some aspects, the isoprene synthase polypeptide or nucleic acid is from the family Fabaceae, such as the Faboideae subfamily. In some aspects, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa*, or *Popular alba x tremula* (CAC35696) Miller et al., Planta 213:483-487, 2001) aspen (such as *Populus tremuloides*) Silver et al., 270 (22):13010-1316, 1995), or English Oak (*Quercus robur*) (Zimmer et al., WO 98/02550). In some aspects, the isoprene synthase polypeptide or nucleic acid is a naturally-occurring isoprene synthase polypeptide or nucleic acid. In some aspects, the isoprene synthase polypeptide or nucleic acid is not a naturally-occurring isoprene synthase polypeptide or nucleic acid. Exemplary isoprene synthase polypeptides and nucleic acids and methods of measuring isoprene synthase activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/1132220, and US Publ. No. 2010/0003716.

Exemplary DXP Pathway Polypeptides and Nucleic Acids

Exemplary DXP pathways polypeptides include, but are not limited to any of the following polypeptides: DXS polypeptides, DXR polypeptides, MCT polypeptides, CMK polypeptides, MCS polypeptides, HDS poly-peptides, HDR polypeptides, IDI polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids of any of the source organisms described herein.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde, 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptide activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptide activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptide activity by measuring the ability of the polypeptide, to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptide activity by measuring the ability of the polypeptide to convert CDP-MEP in vitro, in a cell extract, or in vivo.

HDS polypeptides convert 2-C-methyl-D-erythritol 2,4-cyclodiphosphate (ME-CPP or cMEPP) into (E)-4-hydroxy-3-methylbut-2-en-1-yl diphosphate (HMBPP or HDMAPP). Standard methods can be used to determine whether a polypeptide has HDS polypeptide activity by measuring the ability of the polypeptide, to convert ME-CPP or cMEPP in vitro, in a cell extract, or in vivo.

HDR polypeptides convert (E)-4-hydroxy-3-methylbut-2-en-1-yl diphosphate (HMBPP or HDMAPP) into isopentenyl diphosphate (IPP) and dimethylallyl diphosphate (DMAPP). Standard methods can be used to determine whether a polypeptide has HDR polypeptide activity by measuring the ability of the polypeptide to convert HMBPP or HDMAPP in vitro, in a cell extract, or in vivo.

IDI polypeptides convert isopentenyl diphosphate into dimethylallyl disphosphate. Standard methods can be used to determine whether a polypeptide has IDI polypeptide activity by measuring the ability of the polypeptide, to convert isopentenyl diphosphate in vitro, in a cell extract, or in vivo.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethyl allyl diphosphate (DMAPP) (e.g., converting IPP into DMAPP and/or converting DMAPP into IPP). Exemplary polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI polypeptides and nucleic acids and methods of measuring IDI activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonate decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides, in particular, MVA pathway polypeptides include polypeptides, fragments of polypeptides, peptides, and fusions polypeptides that have at least one activity of an MVA pathway polypeptide. Exemplary MVA pathway polypeptides and nucleic acids and methods of measuring IDI activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In some aspects, the cells contain the upper MVA pathway, which includes AA-CoA thiolase, HMG-CoA synthase, and HMG-CoA reductase nucleic acids, in some aspects, the cells contain the lower MVA pathway, which includes MVK, PMK, MVD, and IDI nucleic acids. In some aspects, the cells contain an entire MVA pathway that includes AA-CoA thiolase, HMG-CoA synthase, HMG-CoA reductase, MVK, PMK, MVD, and IDI nucleic acids. In some aspects, the cells contain an entire MVA pathway that includes AA-CoA thiolase, HMG-CoA synthase, HMG-CoA reductase, MVK. PMDC, IPK, and IDI nucleic acids.

The improved methods described herein can also be used to produce isoprene and a co-product, such as hydrogen. Exemplary hydrogenase polypeptides and nucleic acids, polypeptides and nucleic acids for genes related to production of fermentation side products, and polypeptides and nucleic acids for genes relating to hydrogen reuptake can also be used with the compositions and methods described in. Such polypeptides and nucleic acids are described in U.S. Provisional Patent Application No. 61/141,652, U.S. Provisional Patent Application No. 61/187,934, US Publ. No. 2010/0196988, WO 2010/078457, International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Isoprene Compositions Produced from Renewable Resources

Isoprene compositions produced from renewable resources (e.g. bioisoprene) are distinguished from petro-isoprene compositions in that bioisoprene is produced with other bio-byproducts (compounds derived from the biological sources and/or associated the biological processes that are obtained together with bioisoprene) that are not present or present in much lower levels in petro-isoprene compositions, such as alcohols, aldehydes, ketone and the like. The bio-byproducts may include, but are not limited to, ethanol, acetone, methanol, acetaldehyde, methacrolein, methyl vinyl ketone, 2-methyl-2-vinyloxirane, cis- and trans-3-methyl-1,3-pentadiene, a C5 prenyl alcohol (such as 3-methyl-3-buten-1-ol or 3-methyl-2-buten-1-ol), 2-heptanone, 6-methyl-5-hepten-2-one, 2,4,5-trimethylpyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, 3-hexen-1-ol, 3-hexen-1-yl acetate, limonene, geraniol (trans-3,7-dimethyl-2,6-octadien-1-ol), citronellol (3,7-dimethyl-6-octen-1-ol), (E)-3,7-dimethyl-1,3,6-octatriene, (Z)-3,7-dimethyl-1,3,6-octatriene, 2,3-cycloheptenolpyridine, or a linear isoprene polymer (such as a linear isoprene dimer or a linear isoprene trimer derived from the polymerization of multiple isoprene units). Products derived from bioisoprene contain one or more of the bio-byproducts or compounds derived from any of the by-products. In addition, products derived from bioisoprene may contain compounds formed from these by-products during subsequent chemical conversion. Examples of such compounds include those derived from Diels-Alder cycloaddition of dienophiles to isoprene, or the oxidation of isoprene.

Isoprene compositions produced from renewable resources including particular byproducts or impurities are described in more detail in U.S. Provisional Patent Application No. 61/187,959, U.S. application Ser. No. 12/818,090, PCT/US10/039,088, International Publication No. WO 2009/076676, U.S. patent application Ser. No. 12/335,071 (US Publ. No. 2009/0203102), WO 2010/003007, US Publ. No. 2010/0048964, WO 2009/132220 and US Publ. No. 2010/0003716.

Exemplary Purification Methods

In some aspects, any of the methods described herein further include a step of recovering the isoprene. Additional examples of efficient methods for the production and recovery of isoprene are described in U.S. Provisional Patent Application Ser. Nos. 61/187,959 and 61/187,934, International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716. Additional examples of efficient methods for the production and recovery of isoprene and a coproduct, such as hydrogen, are described in U.S. Provisional Patent Application Nos. 61/141,652, 61/187,934, and 61/187,959, and International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716. In addition, recovery may be achieved by absorption stripping as described in US Appl. No. 12/969,440.

Other Techniques

Isoprene production in cells by the methods described herein can be increased by decoupling isoprene production from cell growth, as described in U.S. Provisional Patent Application Ser. No. 61/187,959, U.S. patent application Ser. No. 12/496,573, International Publication No. WO 2009/076676, U.S. patent application Ser. No. 12/335,071 (US Publ. No. 2009/0203102), WO 2010/003007 US Publ. No. 2010/0048964, WO 2009/132220, and US Publ. No. 2010/0003716. The safety of methods of producing isoprene in cells by the methods described herein can be improved by producing isoprene within safe operating ranges, as described in U.S. Provisional Patent Application Ser. No. 61/187,959, U.S. patent application Ser. No. 12/496,573, International Publication No. WO 2009/076676, U.S. patent application Ser. No. 12/335,071 (US Publ. No. 2009/0203102), WO 2010/003007, US Publ. No. 2010/0048964 WO 2009/132220, and US Publ. No. 2010/0003716. Cell viability at high isoprene titers, such as those achieved by the improved methods of producing isoprene described herein, can be improved as described in U.S. Provisional Patent Application Ser. No. 61/187,959, International Publication No. WO 2009/076676, U.S. patent application Ser. No. 12/335,071 (US Publ. No. 2009/0203102), WO 2010/003007, US Publ. No. 2010/0048964, WO 2009/132220 and US Publ. No. 2010/000371.6.

Additional examples of efficient methods for the production and recovery of isoprene are described in U.S. Provisional Patent Application Ser. No. 61/187,959, International Publication No. WO 2009/076676, U.S. patent application Ser. No. 12/335,071 (US Publ. No. 2009/0203102), WO 2010/003007, US Publ. No. 2010/0048964, WO 2009/132220, US Publ. No. 2010/0003716 and U.S. application Ser. No. 12/969,440. Additional examples of efficient methods for the production and recovery of isoprene and a coproduct, such as hydrogen, are described in U.S. Provisional Patent Application No. 61/141,652, U.S. Provisional Patent Application No. 61/187,934, US Publ. No. 2010/0196977, and WO 2010/078457.

The invention can be further understood by reference to the following examples, which are provided by way of illustration and are not meant to be limiting.

EXAMPLES

Example 1

Construction of E. coli Strains Expressing the S. cerevisiae gi1.2KKDyI Operon, P. alba Isoprene Synthase, M. mazei Mevalonate Kinase, pCL Upper MVA (E. faecalis mvaE and mvaS) and ybhE (pgl)

(i) Construction of Strain EWL201 (BL21, Cm-GI1.2-KKDyI)

E. coli BL21 (Novagen brand, EMD Biosciences, Inc.) was a recipient strain, transduced with MCM331 P1 lysate (lysate prepared according to the method described in Ausubel, et al., Current Protocols in Molecular Biology, John Wiley and Sons, Inc.). MCM331 cells contain chromosomal construct gi1.21KKDyI encoding S. cerevisiae mevalonate kinase, mevalonate phosphate kinase, mevalonate pyrophosphate decarboxylase, and IPP isomerase (i.e., the gi1.2-KKDyI operon from S. cerevisiae). Transductants were selected for by spreading cells onto L Agar and 20 µg/µl chloramphenicol. The plates were incubated overnight at 30° C. Analysis of transductants showed no colonies on control plates (water+cells control plate for reversion and water and P1 lysate control plate for lysate contamination.

Four transductants were picked and used to inoculate 5 mL L Broth and 20 µg/µl chloramphenicol. The cultures were grown overnight at 30° C. with shaking at 200 rpm. To make genomic DNA preps of each transductant for PCR analysis, 1.5 mL of overnight cell culture were centrifuged. The cell pellet was resuspended with 400 µl Resuspension Buffer (20 mM Tris, 1 mM EDTA, 50 mM NaCl, pH 7.5) and 4 µl RNase, DNase-free (Roche) was added. The tubes were incubated at 37° C. for 30 minutes followed by the addition of 4 µl 10% SDS and 4 µl of 10 mg/ml Proteinase K stock solution (Sigma-Aldrich). The tubes were incubated at 37° C. for 1 hour. The cell lysate was transferred into 2 ml Phase Lock Light Gel tubes (Eppendorf) and 200 µl each of saturated phenol pH 7.9 (Ambion Inc.) and chloroform were added. The tubes were mixed well and microcentrifuged for 5 minutes. A second extraction was done with 400 µl chloroform and the aqueous layer was transferred to a new eppendorf tube. The genomic DNA was precipitated by the addition of 1 ml of 100% ethanol and centrifugation for 5 minutes. The genomic DNA pellet was washed with 1 ml 70% ethanol. The ethanol was removed and the genomic DNA pellet was allowed to air dry briefly. The genomic DNA pellet was resuspended with 200 µl TE.

Using Pfu Ultra II DNA polymerase (Strata gene) and 200 ng/µl of genomic DNA as template, 2 different sets of PCR reaction tubes were prepared according to manufacturer's protocol. For set 1, primers MCM130 and GB Cm-Rev (Table 1) were used to ensure transductants were successfully integrated into the attTn7 locus. PCR parameters for set 1 were 95° C. for 2 minutes (first cycle only), 95° C. for 25 seconds, 55° C. for 25 seconds, 72° C. for 25 seconds (repeat steps 2-4 for 28 cycles), 72° C. for 1 minute. For set 2, primers MVD For and MVD Rev (Table 1) were used to ensure that the gi1.2-KKDyI operon integrated properly. PCR parameters for set 2 were 95° C. for 2 minutes (first cycle only), 95° C. for 25 seconds, 55° C. for 25 seconds, 72° C. for 10 seconds (repeat steps 24 for 28 cycles), 72° C. for 1 minute. Analysis of PCR amplicons on a 1.2% E-gel (Invitrogen Corp) showed that all 4 transductant clones were correct. One was picked and designated as strain EWL201.

(ii) Construction of Strain EWL204 (BL21, Loopout-GI1.2-KKDyI)

The chloramphenicol marker was looped out of strain EWL201 using plasmid pCP2.0 as described by Datsenko and Wanner (2000) (Datsenko et al., Proc Natl. Acid. Sci USA 97:6640-6645, 2000). One-step inactivation of chromosomal genes in Escherichia coli K-12 using PCR products. (Datsenko et al., PNAS 97:6640-6645, 2000). EWL201 cells were grown in L Broth to midlog phase and then washed three times in ice-cold, sterile water. An aliquot of 50 µl of cell suspension was mixed with 1 µl of pCP20 and the cell suspension mixture was electroporated in a 2 mm cuvette (Invitrogen Corp.) at 2.5 Volts and 25 µFd using a Gene Pulser Electroporator (Bio-Rad Inc.). 1 ml of LB was immediately added to the cells, then transferred to a 14 ml polypropylene tube (Sarstedt) with a metal cap. Cells were allowed to recover by growing for 1 hour at 30° C. Transformants were selected on L Agar and 20 µg/µl chloramphenicol and 50 µg/µl carbenicillin and incubated at 30° C. overnight. The next day, a single done was grown in 10 ml L Broth and 50 µg/µl carbenicillin at 30° C. until early log phase. The temperature of the growing culture was then shifted to 42° C. for 2 hours. Serial dilutions were made, the cells were then spread onto LA plates (no antibiotic selection), and incubated overnight at 30° C. The next day, 20 colonies were picked and patched onto L Agar (no antibiotics) and LA and 20 µg/µl chloramphenicol plates. Plates were then incubated overnight at 30° C. Cells able to grow on LA plates, but not LA and 2.0 µg/µl chloramphenicol plates, were deemed to have the chloramphenicol marker looped out (picked one and designated as strain EWL204).

(iii) Construction of Plasmid pEWL230 (pTrc P. alba)

Figure 2:
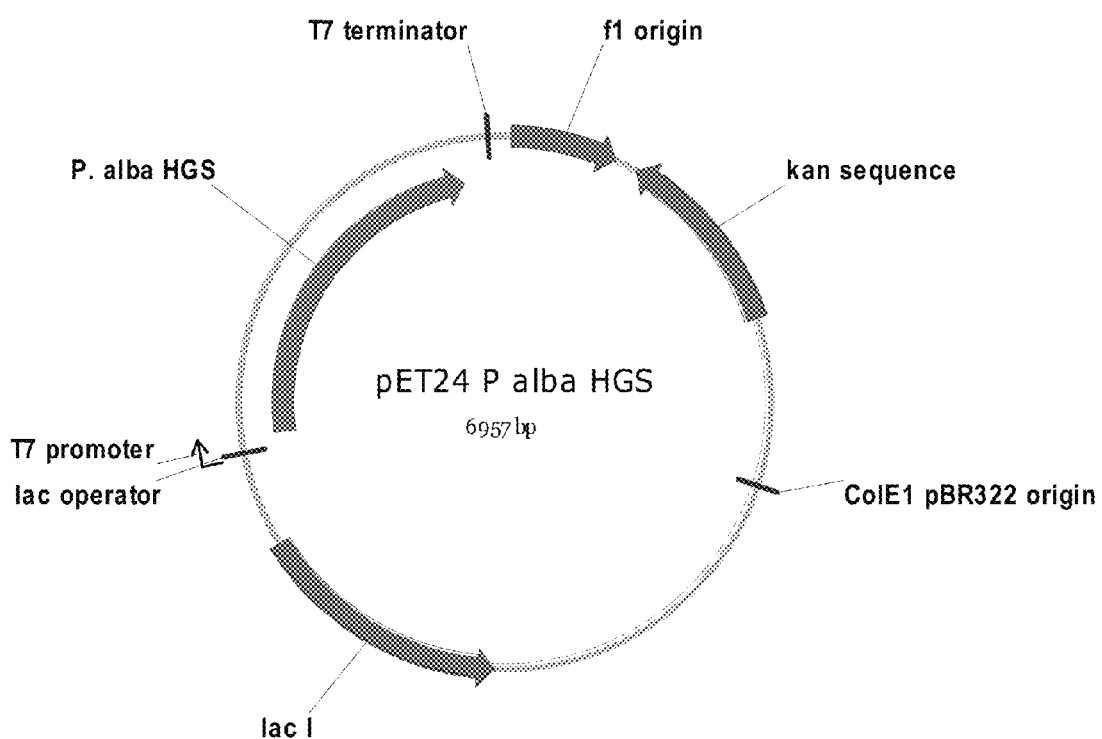
FIG. 2 is a map of plasmid pET24 *P. alba* HGS.

Generation of a synthetic gene encoding Populus alba isoprene synthase (P. alba HGS) was outsourced to DNA2.0 Inc. (Menlo Park, Calif.) based on their codon optimization method for E. coli expression. The synthetic gene was custom cloned into plasmid pET24a (Novagen brand, EMD Biosciences, Inc.) and delivered lyophilized (FIGS. 2, 3A-B; SEQ ID NO:1).

A PCR reaction was performed to amplify the P. alba isoprene synthase (P. alba HGS) gene using pET24 P. alba HGS as the template, primers MCM182 and MCM192, and Herculase II Fusion DNA polymerase (Stratagene) according to manufacturer's protocol. PCR conditions were as follows: 95° C. for 2 minutes (first cycle only), 95° C., for 25 seconds, 55° C., for 20 seconds, 72° C., for 1 minute, repeat for 25 cycles, with final extension at 72° C., for 3 minutes. The P. alba isoprene synthase PCR product was purified using QIAquick PCR Purification Kit (Qiagen Inc.).

Figure 4:
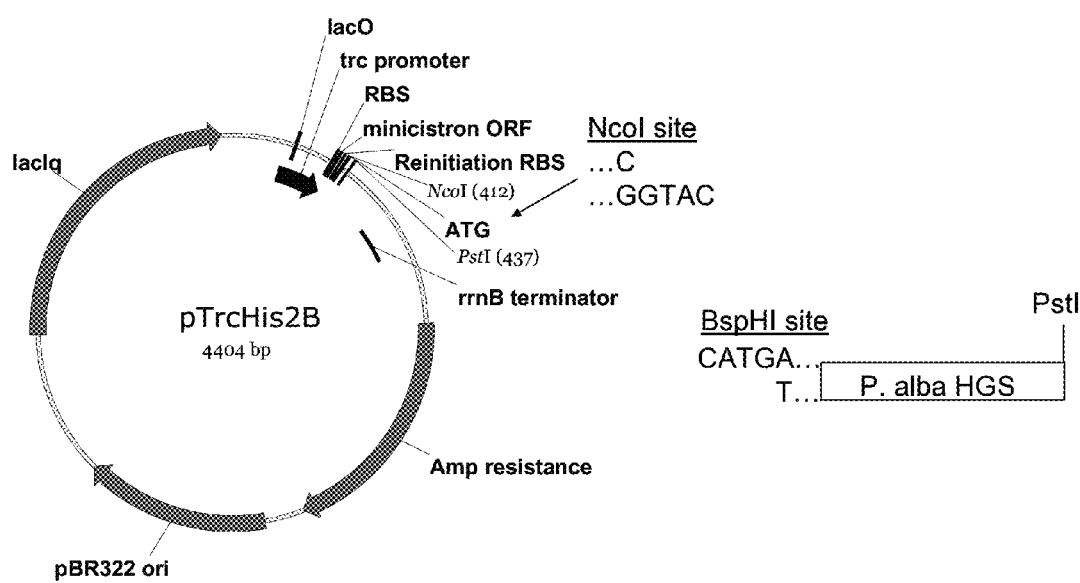
FIG. 4 is a schematic diagram showing restriction sites used for endonuclease digestion to construct plasmid EWL230 and compatible cohesive ends between BspHI and NcoI sites.
Figure 5:
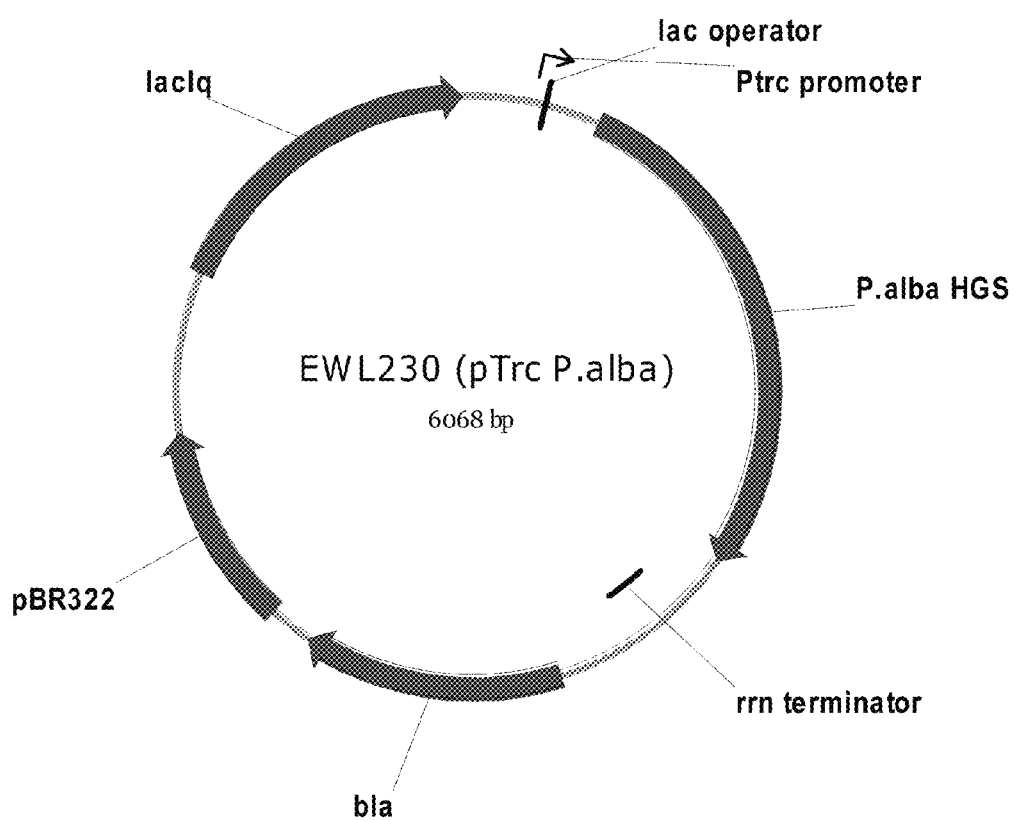
FIG. 5 is a map of plasmid EWL230.

P. alba isoprene synthase PCR product was then digested in a 20 µl reaction containing 1 µl BspHI endonuclease (New England Biolabs) with 2 µl 10×NEB Buffer 4. The reaction was incubated for 2 hours at 37° C. The digested PCR fragment was then purified using the QIAquick PCR Purification Kit. A secondary restriction digest was performed in a 20 µl reaction containing 1 µl PstI endonuclease (Roche) with 2 µl 10× Buffer H. The reaction was incubated for 2 hours at 37° C. The digested PCR fragment was then purified using the QIAquick PCR Purification Kit. Plasmid pTrcHis2B (Invitrogen Corp.) was digested in a 2 µl 10× reaction containing 1 µl NcoI endonuclease (Roche), 1 µl PstI endonuclease, and 2 µl 10× Buffer H. The reaction was incubated for 2 hours at 37° C. The digested pTrcHis2B vector was gel purified using a 1.2% E-gel (Invitrogen Corp.) and extracted using the QIAquick Gel Extraction Kit (Qiagen) (FIG. 4). Using the compatible cohesive ends of BspHI and NcoI sites, a 20 µl ligation reaction was prepared containing 5 µl *P. alba* isoprene synthase insert, 2 µl pTrc vector, 1 µl T4 DNA ligase (New England Biolabs), 2 µl 10× ligase buffer, and 10 µl ddH$_2$O. The ligation mixture was incubated at room temperature for 40 minutes. The ligation mixture was desalted by floating a 0.025 µm nitrocellulose membrane filter (Millipore) in a petri dish of ddH$_2$O and applying the ligation mixture gently on top of the nitrocellulose membrane filter for 30 minutes at room temperature. MCM446 cells (see Section II) were grown in LB to midlog phase and then washed three times in ice-cold, sterile water. An aliquot of 50 µl of cell suspension was mixed with 5 µl of desalted pTrc *P. alba* HGS ligation mix. The cell suspension mixture was electroporated in a 2 mm cuvette at 2.5 Volts and 25 µFd using a Gene Pulser Electroporator. 1 ml of LB is immediately added to the cells, then transferred to a 14 ml polypropylene tube (Sarstedt) with a metal cap. Cells were allowed to recover by growing for 2 hours at 30° C. Transformants were selected on L Agar and 50 µg/µl carbenicillin and 10 mM mevalonic acid and incubated at 30° C. The next day, 6 transformants were picked and grown in 5 ml L Broth and 50 µg/µl carbenicillin tubes overnight at 30° C. Plasmid preps were performed on the overnight cultures using QIAquick Spin Miniprep Kit (Qiagen). Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 µl reaction to ensure the correct sized linear fragment. All 6 plasmids were the correct size and shipped to Quintara Biosciences (Berkeley, Calif.) for sequencing with primers MCM65, MCM66, EL1000 (Table 1). DNA sequencing results showed all 6 plasmids were correct. One plasmid was picked designated as plasmid EWL230 (FIGS. 5, 6A-B; SEQ ID NO:2).

iv) Construction of Plasmid pEWL244 (pTrc *P. alba*-mMVK)

A PCR reaction was performed to amplify the *Methanosarcina mazei* (*M. mazei*) MVK gene using MCM376 as the template (see section (v) below), primers MCM165 and MCM177 (see Table 1), and Pfu Ultra II Fusion DNA polymerase (Stratagene) according to manufacturer's protocol, PCR conditions were as follows: 95° C., for 2 minutes (first cycle only), 95° C., for 25 seconds, 55° C. for 25 seconds, 72° C. for 18 seconds, repeat for 28 cycles, with final extension at 72° C., for 1 minute. The *M. mazei* MVK PCR product was purified using QIAquick PCR Purification Kit (Qiagen Inc.).

Figure 7:
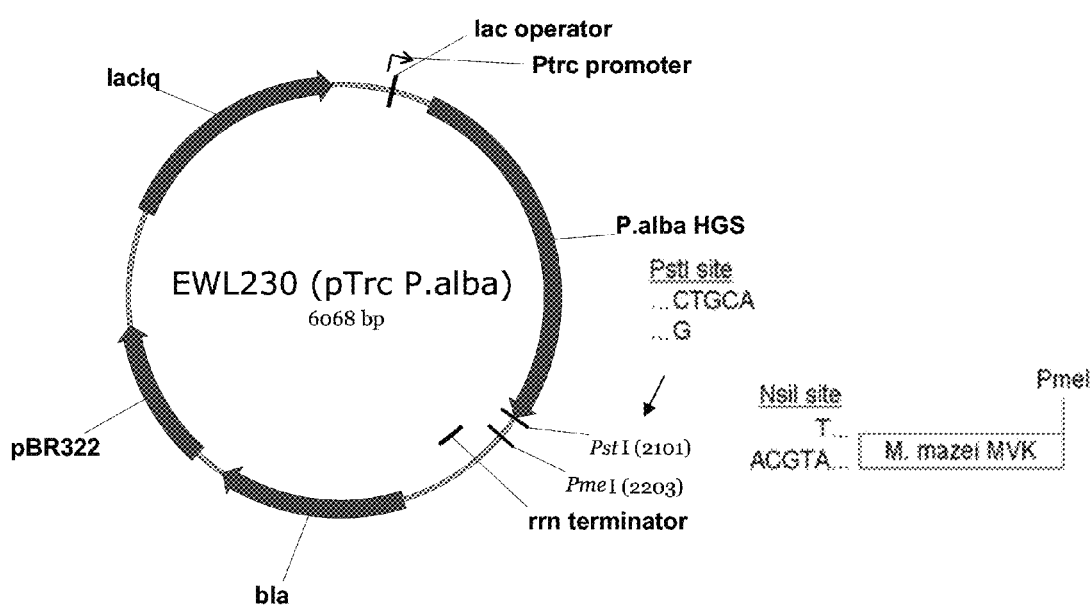
FIG. 7 is a schematic diagram showing restriction sites used for endonuclease digestion to construct plasmid EWL244 and compatible cohesive ends between NsiI and PstI sites.
Figure 8:
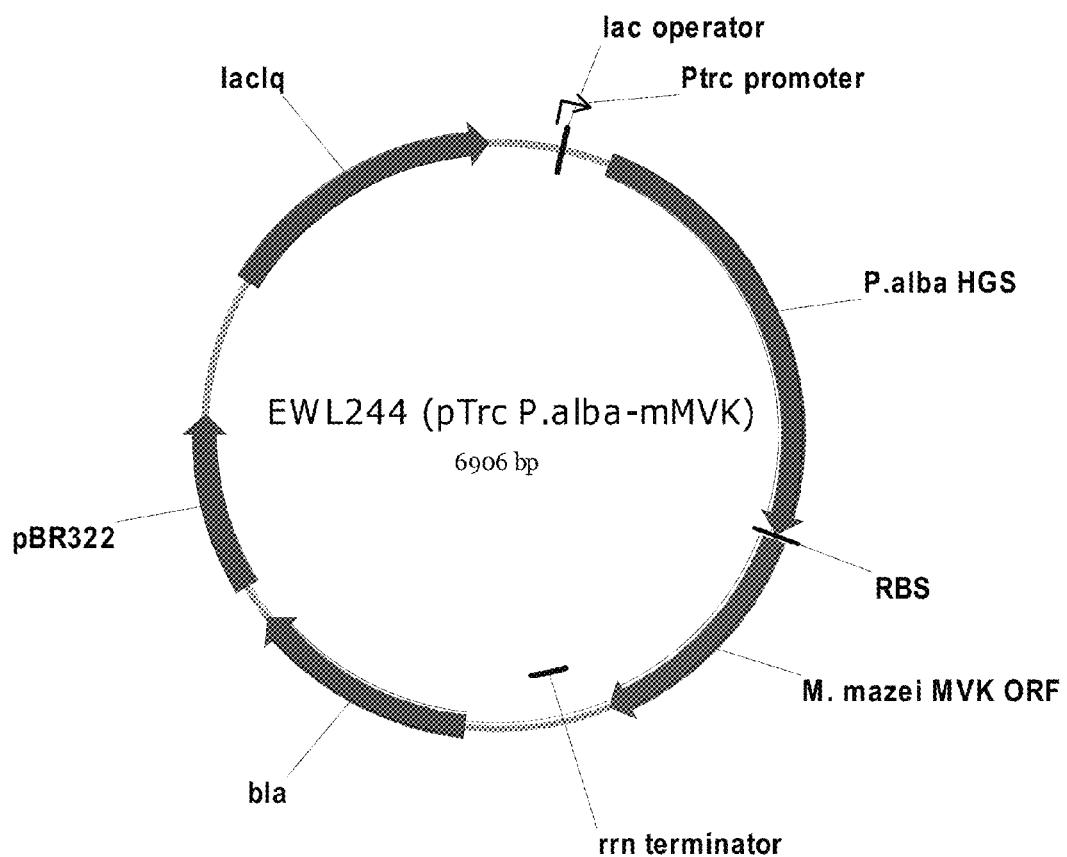
FIG. 8 is a map of plasmid EWL244.

The *M. mazei* MVK PCR product was then digested in a 40 µl reaction containing 8 µl PCR product, 2 µl PmeI endonuclease (New England Biolabs), 4 µl 10×NEB Buffer 4, 4 µl 10×NEB BSA, and 22 µl of ddH$_2$O. The reaction was incubated for 3 hours at 37° C. The digested PCR fragment was then purified using the QIAquick PCR Purification Kit. A secondary restriction digest was performed in a 47 µl reaction containing 2 µl NsiI endonuclease (Roche), 4.7 µl 10× Buffer H, and 40 µl of PmeI digested *M. mazei* MVK fragment. The reaction was incubated for 3 hours at 37° C. The digested PCR fragment was then gel purified using a 1.2% E-gel and extracted using the QIAquick Gel Extraction Kit. Plasmid EWL230 was digested in a 40 µl reaction containing 10 µl plasmid, 2 µl PmeI endonuclease, 4 µl 10×NEB Buffer 4, 4 µl 10×NEB BSA, and 20 µl of ddH$_2$O. The reaction was incubated for 3 hours at 37° C. The digested PCR fragment was then purified using the QIAquick PCR Purification Kit. A secondary restriction digest was performed in a 47 µl reaction containing 2 µl PstI endonuclease, 4.7 µl 10× Buffer H, and 40 µl of PmeI digested EWL230 linear fragment. The reaction was incubated for 3 hours at 37° C. The digested PCR fragment was then gel purified using a 12% E-gel and extracted using the QIAquick Gel Extraction Kit (FIG. 7). Using the compatible cohesive ends of NsiI and PstI sites, a 20 µl ligation reaction was prepared containing 8 µl *M. mazei* MVK insert, 3 µl EWL230 plasmid, 1 µl T4 DNA ligase, 2 µl 10× ligase buffer, and 6 µl ddH$_2$O. The ligation mixture was incubated overnight at 16° C. The next day, the ligation mixture was desalted by floating a 0.025 µm nitrocellulose membrane filter in a petri dish of ddH$_2$O and applying the ligation mixture gently on top of the nitrocellulose membrane filter for 30 minutes at room temperature. MCM446 cells were grown in LB to midlog phase and then washed three times in ice-cold, sterile water. An aliquot of 50 µl of cell suspension was mixed with 5 µl of desalted pTrc *P. alba*-mMVK ligation mix. The cell suspension mixture was electroporated in a 2 mm cuvette at 2.5 Volts and 25 µFd using a Gene Pulser Electroporator. 1 ml of LB is immediately added to the cells, then the cells are transferred to a 14 ml polypropylene tube with a metal cap. Cells were allowed to recover by growing for 2 hour at 30° C. Transformants were selected on LA and 50 µg/µl carbenicillin and 5 mM mevalonic acid plates and incubated at 30° C. The next day, 6 transformants were picked and grown in 5 ml LB and 50 µg/µl carbenicillin tubes overnight at 30° C. Plasmid preps were performed on the overnight cultures using QIAquick Spin Miniprep Kit. Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 µl reaction to ensure the correct sized linear fragment. Three of the 6 plasmids were the correct size and shipped to Quintara Biosciences for sequencing with primers MCM65, MCM66, EL1000, EL1003, and EL1006 (Table 1). DNA sequencing results showed all 3 plasmids were correct. One was picked and designated as plasmid EWL244 (FIGS. 8 and 9A-B; SEQ ID NO:3).

v) Construction of Plasmid MCM376-MVK from *M. mazei* Archaeal Lower in pET200D.

Figure 10A:
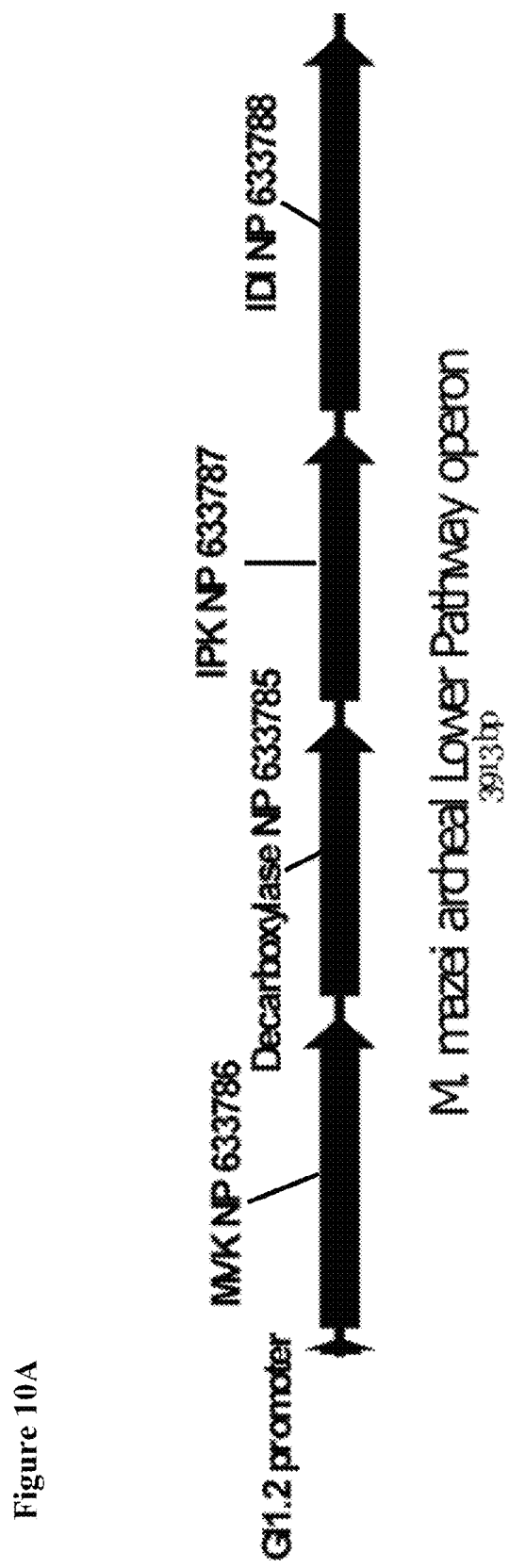
FIG. 10A is a map of the *M. mazei* archaeal Lower Pathway operon.
Figure 11A:
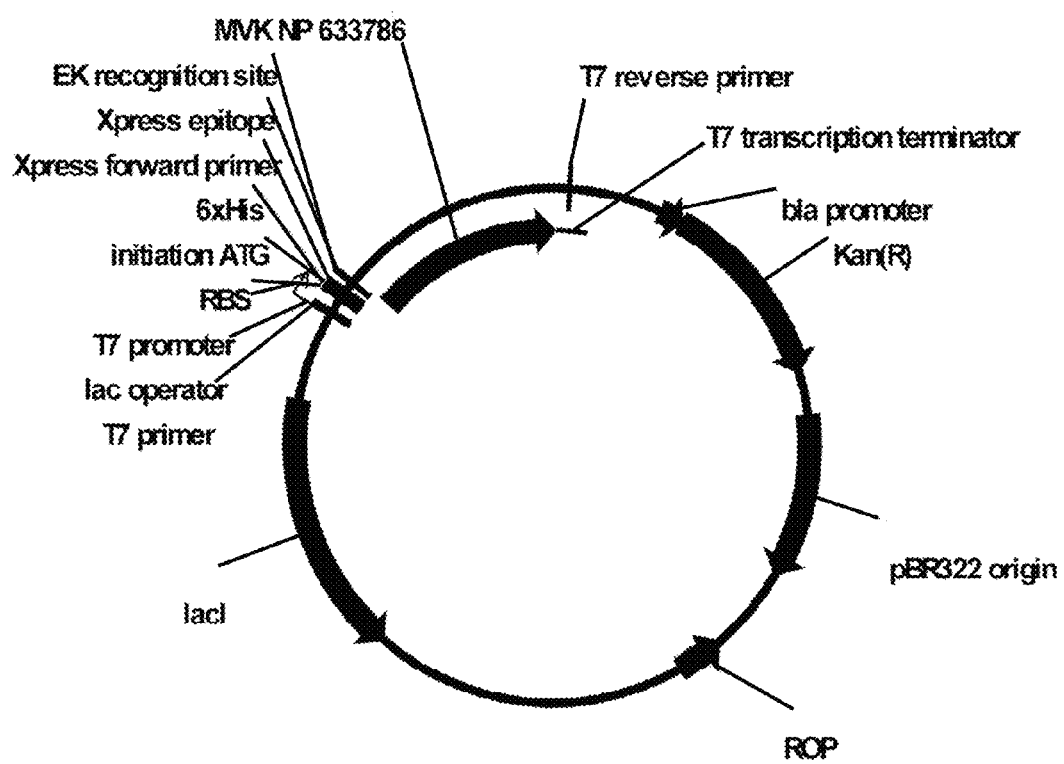
FIG. 11A is a map of MCM376-MVK from *M. mazei* archaeal Lower in pET200D.

The MVK ORF from the *M. mazei* archaeal Lower Pathway operon (FIGS. 10A-C; SEQ ID NO:4) was PCR amplified using primers MCM161 and MCM162 (Table 1) using the Invitrogen Platinum HiFi PCR mix. 45 µL of PCR mix was combined with 1 µL template, 1 µL of each primer at 10 µM, and 2 µL water. The reaction was cycled as follows: 94° C. for 2:00 minutes; 30 cycles of 94° C. for 0:30 minutes, 55° C. for 0:30 minutes and 68° C. for 1:15 minutes; and then 72° C. for 7:00 minutes, and 4° C. until cool. 3 µL of this PCR reaction was ligated to Invitrogen pET200D plasmid according to the manufacturer's protocol, 3 µL of this ligation was introduced into Invitrogen TOP10 cells, and transformants were selected on LA/kan50. A plasmid from a transformant was isolated and the insert sequenced, resulting in MCM376 (FIGS. 11A-C).

vi) Construction of Strain EWL251 (BL21 (DE3), Cm-GI1.2-KKDyI, pTrc *P. alba*-mMVK)

MCM331 cells (which contain chromosomal construct gi1.2KKDyI encoding *S. cerevisiae* mevalonate kinase, mevalonate phosphate kinase, mevalonate pyrophosphate decarboxylase, and IPP isomerase) were grown in LB to midlog phase and then washed three times in ice-cold, sterile water. Mixed 50 µl of cell suspension with 1 µl of plasmid EWL244. The cell suspension mixture was electroporated in a 2 mm cuvette at 2.5 Volts and 25 µFd using a Gene Pulser Electroporator. 1 ml of LB is immediately added to the cells, and then the cells were transferred to a 14 ml polypropylene tube with a metal cap. Cells were allowed to recover by growing for 2 hours at 30° C. Transformants were selected on LA and 50 µg/µl carbenicillin and 5 mM mevalonic acid plates and incubated at 37° C. One colony was selected and designated as strain EWL251.

vii) Construction of Strain EWL256 (BL21 (DE3), Cm-GI1.2-KKDyI, pTrc P. alba-mMVK, pCL Upper MVA)

EWL251 cells were grown in LB to midlog phase and then washed three times in ice-cold, sterile water. Mixed 50 µl of cell suspension with 1 µl of plasmid MCM82 (comprising pCL PtrcUpperPathway (also known as "pCL Upper MVA"), encoding E. faecalis mvaE and mvaS). Plasmid pCL Ptrc Upper Pathway was constructed as described in Example 8 of International Publication No. WO 2009/076676 A2 and U.S. patent application Ser. No. 12/335,071, both of which are incorporated herein by reference in their entireties. The cell suspension mixture was electroporated in a 2 mm cuvette at 2.5 Volts and 25 µFd using a Gene Pulser Electroporator. 1 ml of LB was immediately added to the cells. Cells were then transferred to a 14 ml polypropylene tube with a metal cap. Cells were allowed to recover by growing for 2 hours at 30° C. Transformants were selected on LA and 50 µg/µl carbenicillin and 50 µg/µl spectinomycin plates and incubated at 37° C. One colony was picked and designated as strain EWL256.

TABLE 1

Primer Sequences

| Primer name | Primer sequence |
| --- | --- |
| MCM130 | ACCAATTGCACCCGGCAGA (SEQ ID NO: 10) |
| GB Cm Rev | GCTAAAGCGCATGCTCCAGAC (SEQ ID NO: 11) |
| MVD For | GACTGGCCTCAGATGAAAGC (SEQ ID NO: 12) |
| MVD Rev | CAAACATGTGGCATGGAAAG (SEQ ID NO: 13) |
| MCM182 | GGGCCCGTTTAAACTTTAACTAGACTCTGCAGTTAGCGT TCAAACGGCAGAA (SEQ ID NO: 14) |
| MCM192 | CGCATGCATGTCATGAGATGTAGCGTGTCCACCGAAAA (SEQ ID NO: 15) |
| MCM65 | ACAATTTCACACAGGAAACAGC (SEQ ID NO: 16) |
| MCM66 | CCAGGCAAATTCTGTTTTATCAG (SEQ ID NO: 17) |
| EL1000 | GCACTGTCTTTCCGTCTGCTGC (SEQ ID NO: 18) |
| MCM165 | GCGAACGATGCATAAAGGAGGTAAAAAAACATGGTATCC TGTTCTGCGCCGGGTAAGATTTACCTG (SEQ ID NO: 19) |
| MCM177 | GGGCCCGTTTAAACTTTAACTAGACTTTAATCTACTTTC AGACCTTGC (SEQ ID NO: 20) |
| EL1003 | GATAGTAACGGCTGCGCTGCTACC (SEQ ID NO: 21) |
| EL1006 | GACAGCTTATCATCGACTGCACG (SEQ ID NO: 22) |

TABLE 1-continued

Primer Sequences

| Primer name | Primer sequence |
| --- | --- |
| MCM161 | CACCATGGTATCCTGTTCTGCG (SEQ ID NO: 23) |
| MCM162 | TTAATCTACTTTCAGACCTTGC (SEQ ID NO: 24) | viii) Construction of Strain RM111608-2 (Cm-GI1.2-KKDyI, pTrc P. alba-mMVK, pCL Upper MVA, pBBRC-MPGI1.5-pgl)

The BL21 strain of E. coli producing isoprene (EWL256) was constructed with constitutive expression of the ybhE gene (encoding E. coli 6-phosphogluconolactonase) on a replicating plasmid pBBR1MCS5 (Gentamycin) (obtained from Dr. K. Peterson, Louisiana State University).

FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers Pgl-F (SEQ ID NO:25) and PglGI1.5-R (SEQ ID NO:26) were used to amplify the resistance cassette from the FRT-gb2-Cm-FRT template using Stratagene Herculase II Fusion kit according to the manufacturer's protocol. The PCR reaction (50 µL final volume) contained: 5 µL buffer, 1 template DNA (FRT-gb2-Cm-F from Gene Bridges), 10 pmols of each primer, and 1.5 µL 25 mM dNTP mix, made to 50 µL with dH$_2$O. The reaction was cycled as follows: 1×2 minutes, 95° C. then 30 cycles of (30 seconds at 95° C.; 30 seconds at 63° C.; 3 minutes at 72° C.).

The resulting PCR product was purified using the QIAquick® PCR Purification Kit (Qiagen) and electroporated into electrocompetent MG1655 cells harboring the pRed-ET recombinase-containing plasmid as follows. MG1655 cells were prepared for electroporation by growing in 5 mLs of L broth to and OD$_{600}$~0.6 at 30° C. The cells were induced for recombinase expression by the addition of 4% arabinose and allowed to grow for 30 minutes at 30° C. followed by 30 minutes of growth at 37° C. An aliquot of 1.5 mLs of the cells was washed 3-4 times in ice cold dH$_2$O. The final cell pellet was resuspended in 40 µL of ice cold dH$_2$O and 2-5 of the PCR product was added. The electroporation was carried out in 1-mm gap cuvettes, at 1.3 kV in a Gene Pulser Electroporator (Bio-Rad Inc.). Cells were recovered for 1-2 hours at 30° C. and plated on L agar containing chloramphenicol (5 µg/mL). Five transformants were analyzed by PCR and sequencing using primers flanking the integration site (2 primer sets: pgl and 49 rev and 3' EcoRV-pglstop; Bottom Pgb2 and Top GB's CMP (946)). A correct transformant was selected and this strain was designated MG1655 GI1.5-pgl::CMP.

Figure 12:
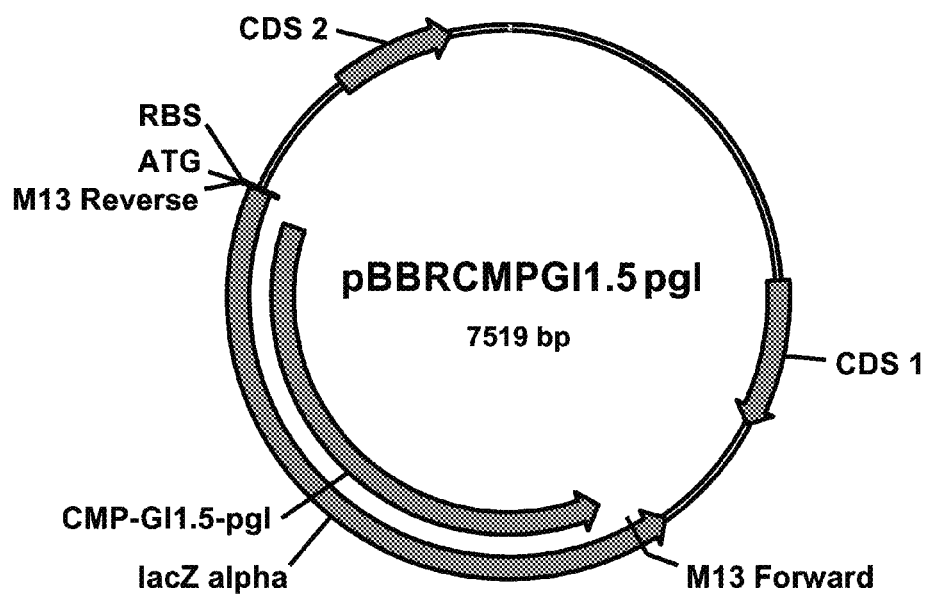
FIG. 12 is a map of plasmid pBBRCMPGI1.5-pgl.

The chromosomal DNA of MG1655 GI1.5-pgl::CMP was used as template to generate a PCR fragment containing the FRT-CMP-FRT-GI1.5 ybhE construct. This construct was cloned into pBBR1MCS5 (Gentamycin) as follows. The fragment, here on referred to as CMP-GI1.5-pgl, was amplified using the 5' primer Pglconfirm-F (SEQ ID NO:27) and 3' primer 3' EcoRV-pglstop (SEQ ID NO:28). The resulting fragment was cloned using the Invitrogen TOPO-Blunt cloning kit into the plasmid vector pCR-Blunt II-TOPO as suggested from the manufacturer. The NsiI fragment harboring the CMP-GI1.5-pgl fragment was cloned into the PstI site of pRBR1MCS5 (Gentamycin). A 20 µl ligation reaction was prepared containing 5 µl CMP-GI1.5-pgl insert, 2 µl pBBR1MCS5 (Gentamycin) vector, 1 µl T4 DNA ligase (New England Biolabs), 2 µl 10× ligase buffer, and 10 µl ddH₂O. The ligation mixture was incubated at room temperature for 40 minutes then 2-4 µL were electroporated into electrocompetent Top10 cells (Invitrogen) using the parameters disclosed above. Transformants were selected on L agar containing 10 µg/ml chloramphenicol and 5 µg/ml. Gentamycin. The sequence of the selected clone was determined using a number of the primers described above as well as with the in-house T3 and Reverse primers provided by Sequetech, CA. This plasmid was designated pBBRCMPGI1.5 pgl (FIGS. 12, 13A-B and SEQ ID NO:6).

Plasmid pBBRCMPGI1.5-pgl was electroporated into EWL256, as described herein and transformants were plated on L agar containing Chloramphenicol (10 µg/mL), Gentamycin (5 µg/mL), spectinomycin (50 µg/mL), and carbenicillin (50 µg/mL). One transformant was selected and designated strain RM111608-2.

```
Primers:
Pgl-F
                                        (SEQ ID NO: 25)
5'-ACCGCCAAAAGCGACTAATTTTAGCTGTTACAGTCAGTTGAATTAA

CCCTCACTAAAGGGCGGCCGC-3'

PglGI1.5-R
                                        (SEQ ID NO: 26)
5'-GCTGGCGATATAAACTGTTTGCTTCATGAATGCTCCTTTGGGTTAC

CTCCGGGAAACGCGGTTGATTTGTTTAGTGGTTGAATTATTTGCTCAGG

ATGTGGCATAGTCAAGGGCGTGACGGCTCGCTAATACGACTCACTATAG

GGCTCGAG-3'

3' EcoRV-pglstop:
                                        (SEQ ID NO: 28)
5'-CTT GAT ATC TTA GTG TGC GTT AAC CAC CAC pgl + 49 rev:
                                        (SEQ ID NO: 29)
CGTGAATTTGCTGGCTCTCAG Bottom Pgb2:
                                        (SEQ ID NO: 30)
GGTTTAGTTCCTCACCTTGTC Top GB's CMP (946):
                                        (SEQ ID NO: 31)
ACTGAAACGTTTTCATCGCTC Pglconfirm-F
                                        (SEQ ID NO: 27)
5'-ACCGCCAAAAGCGACTAATTTTAGCT-3'
```

Example 2

Improvement of Isoprene Production by Constitutive Expression of ybhE (pgl) in E. coli This example shows production of isoprene in a strain constitutively expressing E. coli ybhE (pgl) compared to a control strain expressing ybhE at wild-type levels (i.e., EWL256). The gene ybhE (pgl) encodes E. coli 6-phosphogluconolactonase that suppresses posttranslational gluconylation of heterologously expressed proteins and improves product solubility and yield while also improving biomass yield and flux through the pentose phosphate pathway (Aon et al., Applied and Environmental Microbiology 74 (4):950-958, 2008).

i) Small Scale Analysis

Media Recipe (per liter fermentation media): $K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 1 g, 1000× Trace Metals Solution 1 ml. All of the components were added together and dissolved in $diH_2O$. The pH was adjusted to 6.8 with ammonium hydroxide (30%) and brought to volume. Media was filter-sterilized with a 0.22 micron filter. Glucose 5.0 g and antibiotics were added after sterilization and pH adjustment.

1000× Trace Metal Solution (per liter fermentation media): Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZuSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The is adjusted to 3.0 with HCl/NaOH, and then the solution is brought to volume and filter-sterilized with a 0.22 micron filter.

(a) Experimental Procedure

Isoprene production was analyzed by growing the strains in a Cellerator™ from MicroReactor Technologies, Inc. The working volume in each of the 24 wells was 4.5 mL. The temperature was maintained at 30° C. the pH setpoint was 7.0, the oxygen flow setpoint was 20 sccm and the agitation rate was 800 rpm. An inoculum of E. coli strain taken from a frozen vial was streaked onto an LB broth agar plate (with antibiotics) and incubated at 30° C. A single colony was inoculated into media with antibiotics and grown overnight. The bacteria were diluted into 4.5 mL of media with antibiotics to reach an optical density of 0.05 measured at 550 nm.

Off-gas analysis of isoprene was performed using a gas chromatograph-mass spectrometer (GC-MS) (Agilent) headspace assay. Sample preparation was as follows: 100 µL of whole broth was placed in a sealed GC vial and incubated at 30° C. for a fixed time of 30 minutes. Following a heat kill step, consisting of incubation at 70° C. for 5 minutes, the sample was loaded on the GC.

Optical density (OD) at a wavelength of 550 nm was obtained using a microplate reader (Spectramax) during the course of the run. Specific productivity was obtained by dividing the isoprene concentration (µg/L) by the OD reading and the time (hour).

The two strains EWL256 and RM111608-2 were assessed at 200 and 400 µM IPTG induction levels. Samples were analyzed for isoprene production and cell growth (OD550) at 1, 2.5, 4.75, and 8 hours post-induction. Samples were done in duplicate.

(b) Results

The example demonstrated that at 2 different concentrations of IPTG the strain expressing the ybhE (pgl) had a dramatic 2-3 fold increase in specific productivity of isoprene compared to the control strain.

ii) Isoprene Fermentation from E. coli Expressing Cm-GI1.2-KKDyI, M. mazei Mevalonate Kinase, P. alba Isoprene Synthase, and ybhE (pgl) (RM111608-2) and Grown in Fed-Batch Culture at the 15-L Scale Medium Recipe (per liter fermentation medium): $K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified trace Metal Solution: Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in Di H$_2$O, pH to 3.0 with HCl/NaOH, then q.s. to volume and filter sterilized with a 0.22 micron filter Fermentation was performed in a 15-L bioreactor with BL21 (DE3) *E. coli* cells containing the upper mevalonic acid (MVA) pathway (pCL Upper), the integrated lower MVA pathway (gi-1.2KKDyI), high expression of mevalonate kinase from *M. mazei* and isoprene synthase from *P. alba* (pTrcAlba-mMVK), and high expression of *E. coli* pgl (pBBR-pgl). This example was carried out to monitor isoprene formation from glucose at the desired fermentation pH 7.0 and temperature 34° C. A frozen vial of the *E. coli* strain was thawed and inoculated into tryptone-yeast extract medium. After the inoculum grew to OD 1.0, measured at 550 nm, 500 mL was used to inoculate a 15-L bioreactor bringing the initial volume to 5-L.

Figure 14A:
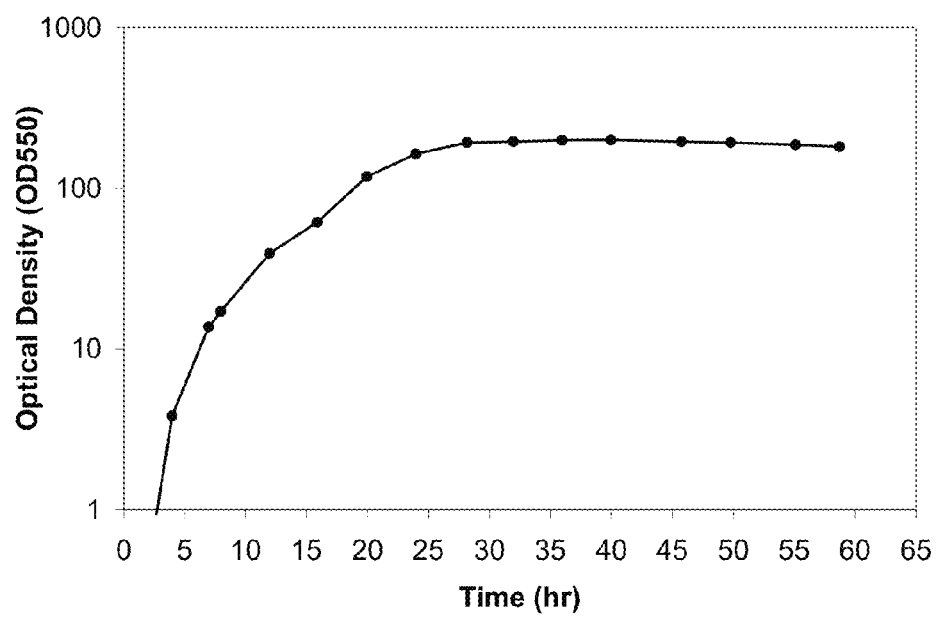
FIGS. 14A-F are graphs of isoprene production by *E. coli* strain expressing *M. mazei* mevalonate kinase, *P. alba* isoprene synthase, and pgl (RHM111608-2), and grown in fed-batch culture at the 15-L scale.
Figure 14B:
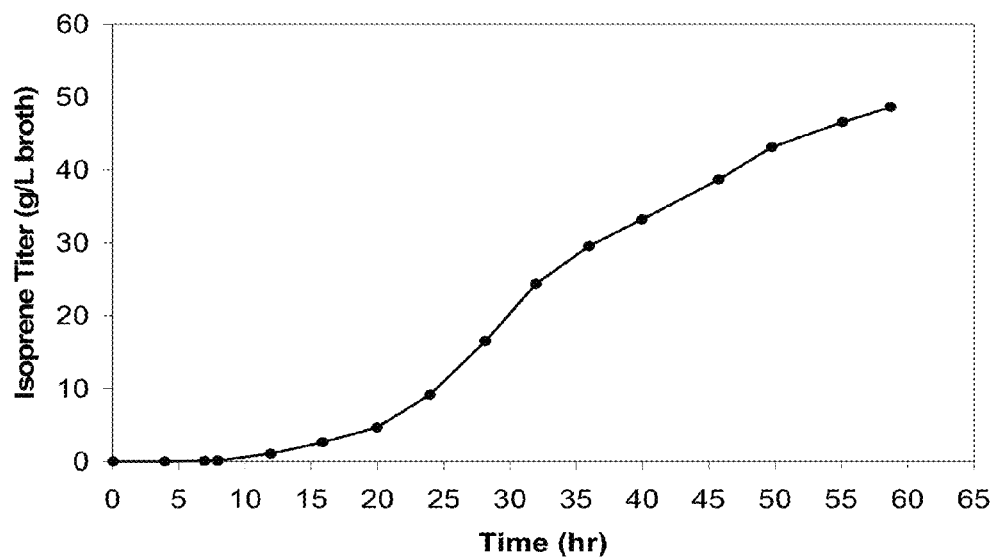
Figure 14C:
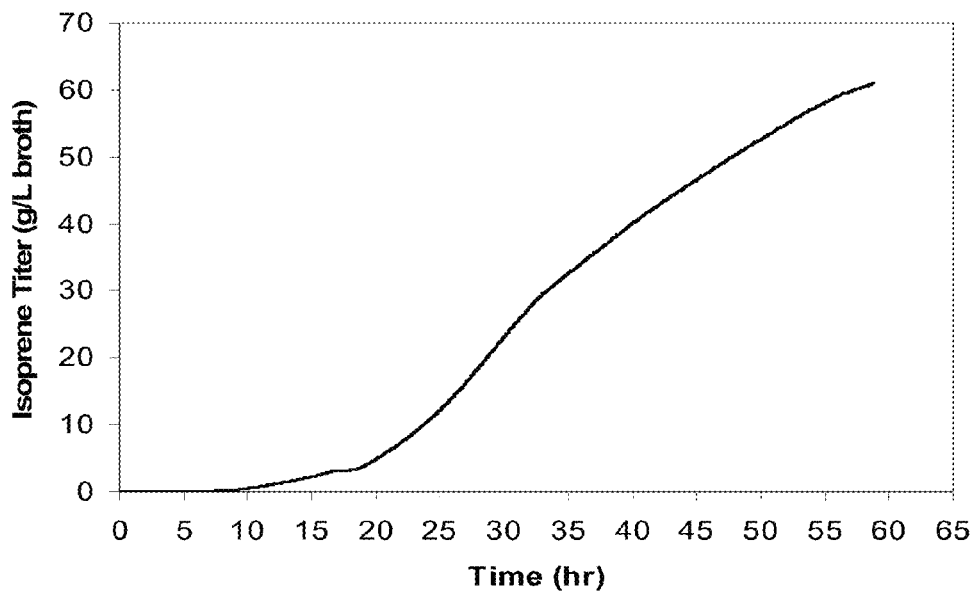
Figure 14D:
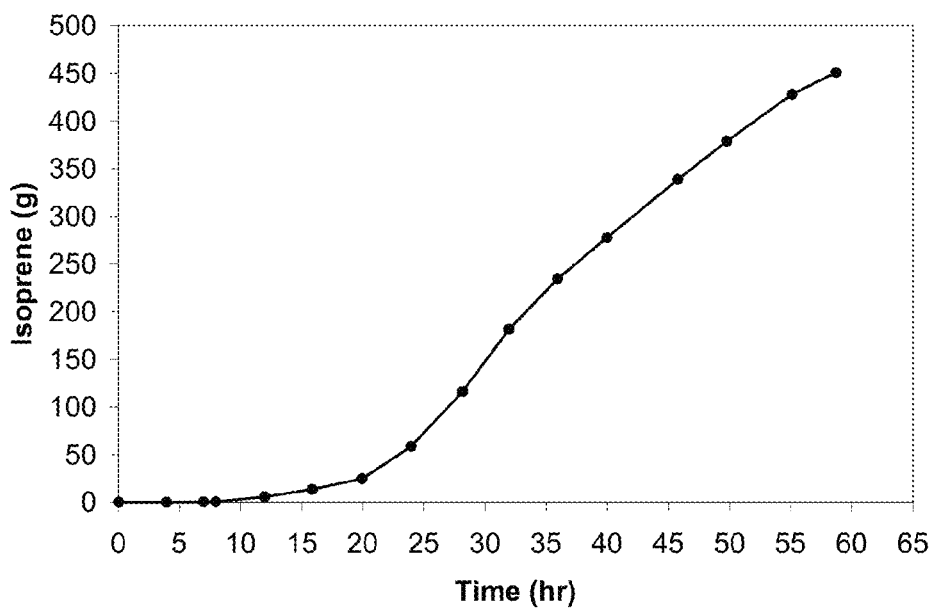
Figure 14E:
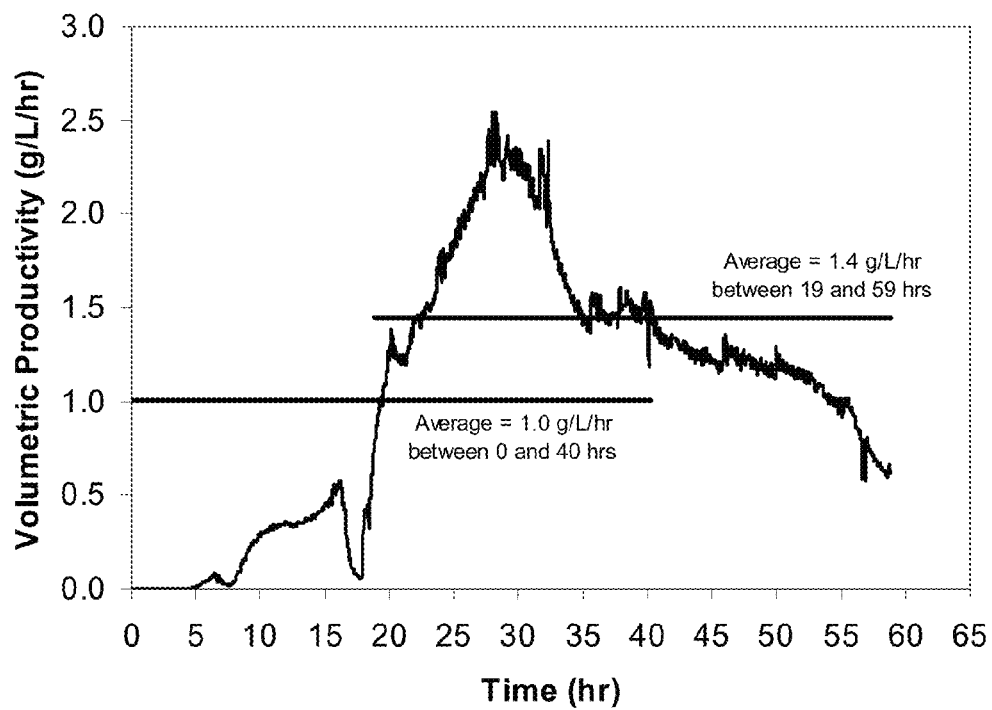
Figure 14F:
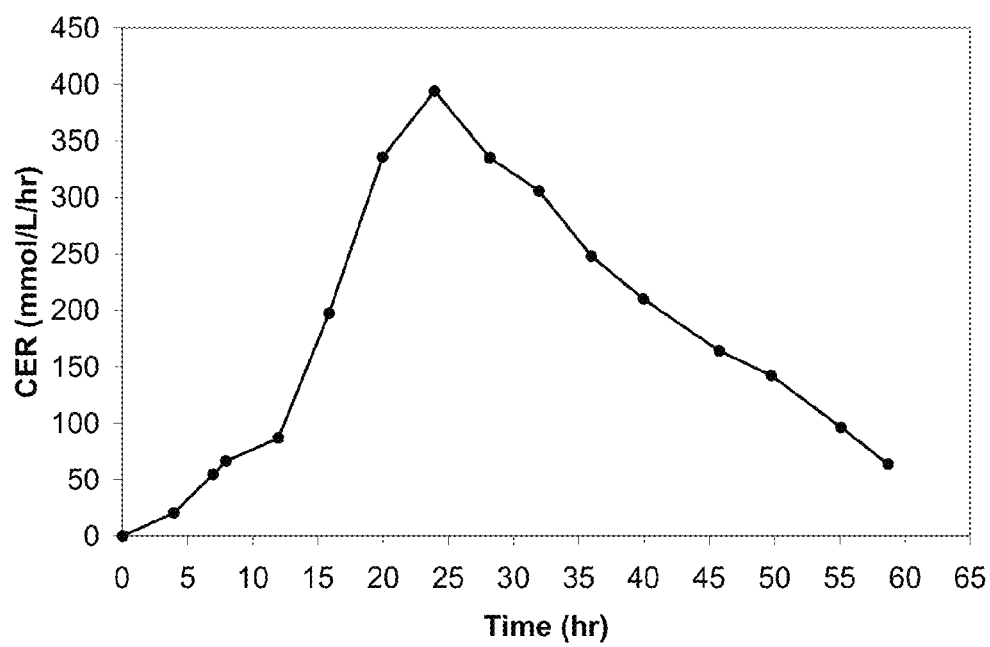
Figure 15:
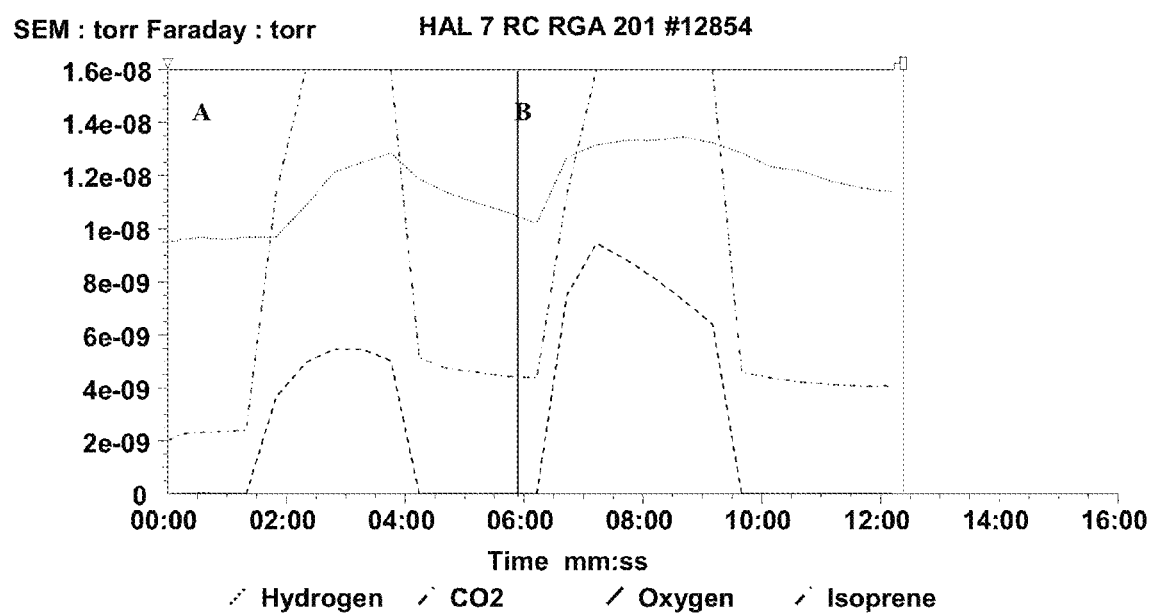
FIGS. 15A-B are graphs showing analysis of off-gas from fermentation in 15 L bioreactors. Sample A is strain RM111608-2 sampled at 64.8 hours. Sample B is strain EWL256 was *E. coli* BL21 (DE3), pCL upper, cmR-gi1.2-yKKDyI, pTrcAlba-mMVK sampled at 34.5 hours. Hydrogen is detected above the baseline ($0.95 \times 10^{-8}$ torr) for both samples.

Glucose was fed at an exponential rate until cells reached the stationary phase. After this time the glucose feed was decreased to meet metabolic demands. The total amount of glucose delivered to the bioreactor during the 40 hour (59 hour) fermentation was 3.1 kg (4.2 kg at 59 hour). Induction was achieved by adding IPTG. The IPTG concentration was brought to 110 µM when the optical density at 550 nm (OD$_{550}$) reached a value of 4. The IPTG concentration was raised to 192 µM when OD$_{550}$ reached 150. The OD$_{550}$ profile within the bioreactor over time is shown in FIG. 14A. The isoprene level in the off gas from the bioreactor was determined using a Hiden mass spectrometer. The isoprene titer increased over the course of the fermentation to a maximum value of 33.2 g/L at 40 hours (48.6 g/L at 59 hours) (FIG. 14B). The isoprene titer increased over the course of the fermentation to a maximum value of 40.0 g/L at 40 hours (60.5 g/L at 59 hours) (FIG. 14C). The total amount of isoprene produced during the 40-hour (59-hour) fermentation was 281.3 g (451.0 g at 59 hours) and the time course of production is shown in FIG. 14D. The time course of volumetric productivity is shown in FIG. 14E and shows that an average rate of 1.0 g/L/hr was maintained between 0 and 40 hours (1.4 g/L/hour between 19 and 59 hour). The metabolic activity profile, as measured by CER, is shown in FIG. 14F. The molar yield of utilized carbon that went into producing isoprene during fermentation was 19.6% at 40 hours (23.6% at 59 hours). The weight percent yield of isoprene from glucose was 8.9% at 40 hours (10.7% at 59 hours).

Example 3

Recovery of Isoprene Produced from Renewable Resources

Figure 16A:
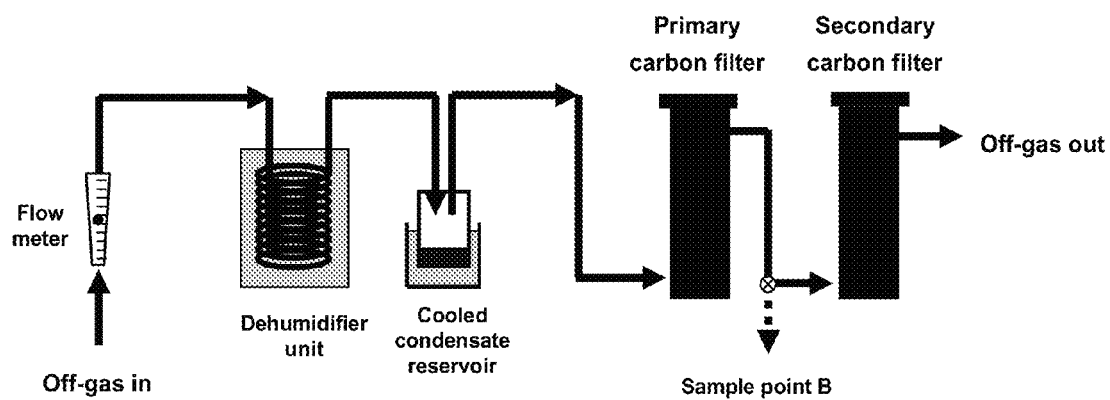
FIG. 16A shows an exemplary isoprene recovery unit.
Figure 16B:
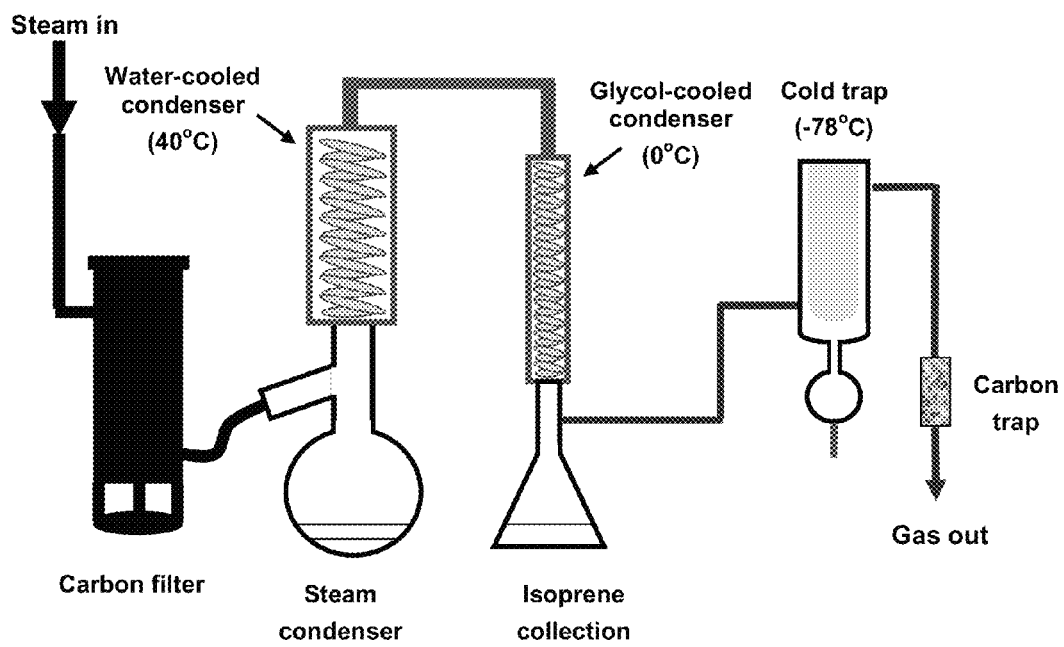
FIG. 16B shows an exemplary isoprene desorption/condensation setup.

Isoprene was recovered from a set of four 15-L scale fermentations in a two-step operation involving stripping of isoprene from the fermentation off-gas stream by adsorption to activated carbon, followed by off-line steam desorption and condensation to give liquid bioisoprene (FIGS. 16A and 16B). The total amount of isoprene produced by the four fermentors was 1150 g (16.9 mol), of which 953 g (14 mol, 83%) was adsorbed by the carbon fillers. Following the steam desorption/condensation step, the amount of liquid isoprene recovered was 810 g, corresponding to an overall recovery yield of 70%. The recovered isoprene was analyzed for the presence of impurities.

Figure 17:
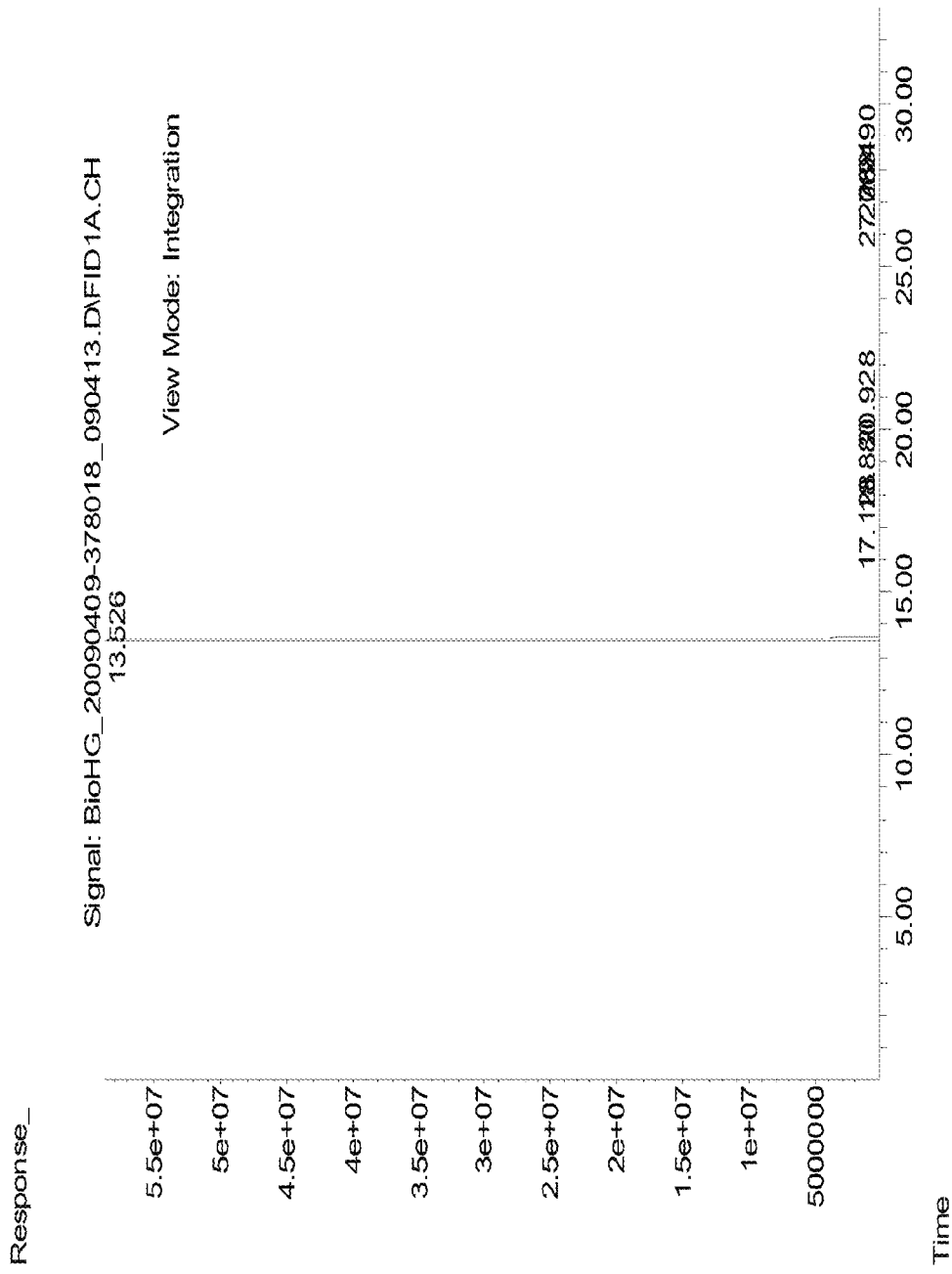
FIG. 17 shows a GC/FID chromatogram of an isoprene product. The material was determined to be 99.7% pure.

Analysis and Impurity Profile of Isoprene Liquid Produced from Renewable Resources Recovered bioisoprene liquid was analyzed by GC/MS and gas chromatography/flame ionization detection (GC/FID) to determine the nature and levels of impurities. The product was determined to be >99.5% pure and contained several dominant impurities in addition to many minor components. The GC/FID chromatogram is depicted in FIG. 17, and the typical levels of impurities are shown in Table 2. The impurity profile was similar to other bioisoprene, batches produced on this scale.

TABLE 2

Summary of the nature and levels of impurities seen in several batches of isoprene produced from renewable resources.

| Compound | Retention Time (min) | | Conc. Range |
|---|---|---|---|
| | GC/MS | GC/FID | |
| Ethanol | 1.59 | 11.89 | <50 ppm |
| Acetone | 1.624 | 12.673 | <100 ppm |
| Methacrolein | 1.851 | 15.369 | <200 ppm |
| Methyl vinyl ketone | 1.923 | 16.333 | <20 ppm |
| Ethyl acetate | 2.037 | 17.145 | 100 to 800 ppm |
| 3-Methyl-1,3-pentadiene | 2.27 | 18.875 | 50 to 500 ppm |
| Methyl vinyl oxirane | 2.548 | 19.931 | <100 ppm |
| Isoprenol | 2.962 | 21.583 | <500 ppm |
| 3-methyl-1-butanol | 2.99 | 21.783 | <50 ppm |
| 3-hexen-1-ol | 4.019 | 24.819 | <100 ppm |
| Isopentenyl acetate | 4.466 | 25.733 | 200 to 1000 ppm |
| 3-hexen-1-yl acetate | 5.339 | 27.223 | <400 ppm |
| limonene | 5.715 | 27.971 | <500 ppm |
| Other cyclics | 5.50-6.50 | 27.5-28.0 | <200 ppm |

Figure 18A:
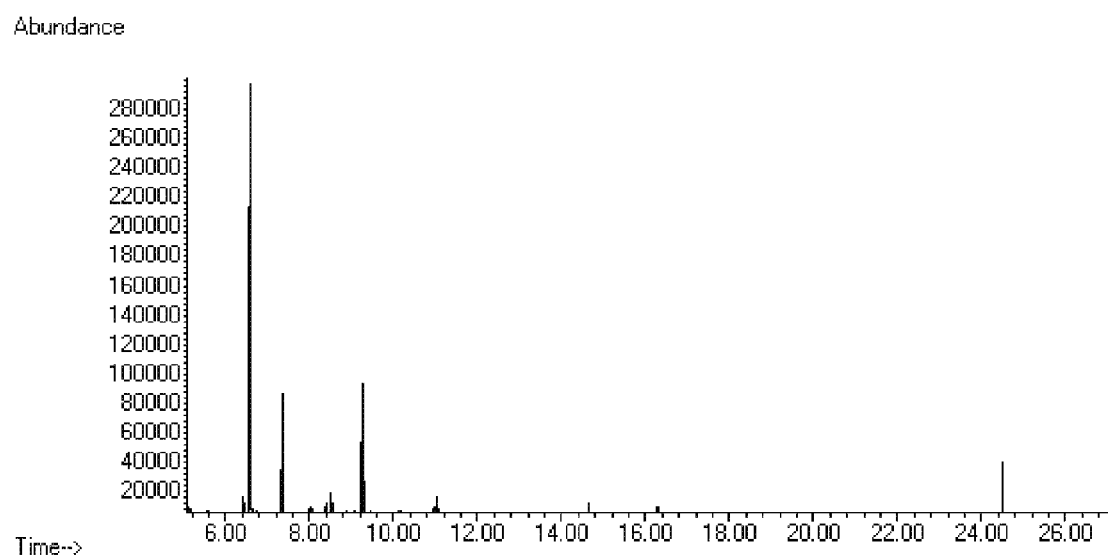
FIG. 18A-C show the GC/FID chromatograms of an isoprene sample before (A) and after treatment with alumina (B) or silica (C). The isoprene peak is not shown in these chromatograms.
Figure 18B:
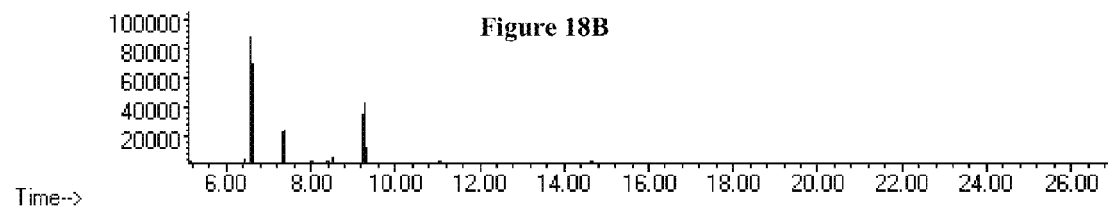
Figure 18C:
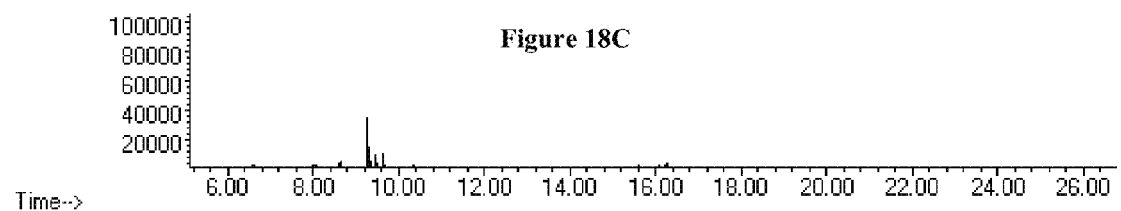

Purification of Isoprene Produced from Renewable Resources by Treatment with Adsorbents Adsorbents are widely used by industry for the removal of trace impurities from hydrocarbon feedstocks. Suitable adsorbents include zeolite, alumina and silica-based materials. Isoprene can be substantially purified by passage over silica gel, and to a lesser extent with alumina. FIG. 18 shows the GC/FID chromatograms of an isoprene sample before (A) and after treatment with alumina (B) or silica (C). The Selexsorb™ adsorbent products from BASF is one of the adsorbents of choice for the removal of polar impurities from isoprene produced from renewable resources. Specifically, the Selexsorb CD and CDX products are preferred given their proven utility for removal of polar impurities from isoprene and butadiene feedstocks.

Example 4

Increased Production of Isoprene Gas Using a Membrane Bioreactor System

I. Construction of *E. coli* Strain CMP234

P1 transduction enables movement of up to 100 kb of DNA between bacterial strains (Thomason et al. 2007). A 17,257 bp deletion in *E. coli* BL21 (DE3) was replaced by moving a piece of the bacterial chromosome from *E. coli* K12 MG1655 to *E. coli* BL21. (DE3) using P1 transduction.

Two strategies were used employing different selectable markers to identify colonies containing the recombined bacterial chromosome. First, we inserted an antibiotic marker in a gene close to the 17,257 bp sequence to be transferred, whose deletion was not likely to be detrimental to the strain. A strain containing that antibiotic marker will likely have the 17,257 bp piece of bacterial chromosome transduced at the same time as the marker. In this case, we inserted a gene encoding kanamycin resistance ("kan$^R$") into the ybgS gene, encoding a 126 amino acid protein of unknown function. Second, since it is known that a number of genes involved in utilization of galactose are close to pgl in the 17,257 bp piece to be transduced into *E. coli* BL21 (DE3), colonies transduced with a P1 lysate obtained from *E. coli* K12 MG1655 (which contains the 17,257 bp sequence deleted in *E. coli* BL21 (DE3)) and isolated in M9 medium (6 g/L Na$_2$PO$_4$, 3 g/L KH$_2$PO$_4$, 0.5 g/L NaCl, 0.5 g/L NH$_4$Cl, 0.1 mM CaCl$_2$, 2 mM MgSO$_4$) containing 0.4% (w/v) galactose will likely contain the 17,257 bp piece of bacterial chromosome.

Primers MCM120 (SEQ ID NO:32) and MCM224 (SEQ ID NO:33) were used to amplify the chloramphenicol resistance ("Cm$^R$") cassette from the GeneBridges FRT-gb2-Cm-FRT template using the Stratagene Herculase™ II Fusion kit (Agilent Technologies, Stratagene Products Division, La Jolla, Calif.) according to the manufacturer's protocol. Four 50 μL PCR reactions were cycled as follows: 95° C./2 minutes; 30 cycles of 95° C./20 seconds, 55° C./20 seconds, 72° C./1 minute; and 72° C./3 minutes. Reactions were then cooled to 4° C. The four reactions were pooled, loaded onto a Qiagen PCR column according to the manufacturer's protocol and eluted with 60 μL elution buffer ("EB") at 55° C.

Plasmid pRedET-carbenicillin$^R$ (GeneBridges, Heidelberg, Germany) was electroporated into *E. coli* BL21 (DE3) strain MCM446 (Cm$^R$, gi1.6mKKDyI A1-3) using standard procedures. Transformants were recovered by shaking for one hour in SOC medium at 30° C., and then selected on LB+50 μg/mL carbenicillin ("LB/carb50") plates at 30° C. overnight. A carbenicillin-resistant colony was frozen as strain MCM508.

Strain MCM508 was grown from a fresh streak in 5 nit LB/carb50 at 30° C. to an OD$_{600}$ of ~0.5. At that point, 40 mM L-arabinose was added, and the culture was incubated at 37° C. for 1.5 hours. Cells were then harvested by centrifugation, electroporated with 3 μL of purified amplicons as described above, and then recovered in 500 μL SOC medium at 37° C. for 1.5-3 hours. Transformants were selected on LB+10 μg/mL kanamycin (LB/kan10) plates at 37° C.

Recombination of the amplicon at the target locus was confirmed by PCR with primers (SEQ ID NO:34) and MCM208 (SEQ ID NO:35). The resulting amplicons were sequenced to identify four clones having the sequences listed below. Four carbenicillin-sensitive clones were frozen as strains MCM515-MCM521.

Strains MCM518-MCM521 were re-streaked onto LB/kan10 and grown overnight at 37° C. Colonies of strains MCM518-MCM521 were picked, cultured in LB/kan10 at 37° C. and electrotransformed with plasmid pCP20, which encodes the yeast Flp recombinase, chloramphenicol and ampicillin resistance genes and confers temperature sensitive replication on host cells (Cherepanov, P. P. et al., *Gene* 158 (1):9-14 (1995)). Cells were recovered in 500 μL SOC medium by shaking at 30° C. for 1 hour. Transformants were selected on LB/carb50 plates at 30° C. overnight. The following morning a colony from each plate was grown at 30° C. in LB/carb50 medium until visibly turbid. The culture was then shifted to 37° C. for at least 3 hours. Cells were streaked from that culture on to LB plates and grown overnight at 37° C.

The following clay colonies were patched to LB, LB/carb50 and LB/kan10. Clones that were sensitive to both carbenicillin and kanamycin (i.e., which could not grow on carb50 and kan10) were cultured in liquid LB and frozen as strains MCM528-MCM531.

TABLE 3

*E. coli* strains

| Strain | Description | Parent |
|---|---|---|
| MCM508 | BL21 gi1.6-mKKDyI + predet.-carb | MCM446 |
| MCM518 | BL21 neo-PL.6-mKKDyI, clone 10 | MCM508 |
| MCM519 | BL21 neo-PL.0-mKKDyI, clone 11 | MCM508 |
| MCM520 | BL21 neo-PL.0-mKKDyI (bad RBS in front of mMVK), clone 13 | MCM508 |
| MCM521 | BL21 neo-PL.2-mKKDyI, clone 15 | MCM508 |
| MCM528 | BL21 PL.6-mKKDyI, neo$^R$ looped out | MCM518 |
| MCM529 | BL21 PL.0-mKKDyI, neo$^R$ looped out | MCM519 |
| MCM530 | BL21 PL.0-mKKDyI (bad RBS in front of mMVK), neo$^R$ looped out | MCM520 |
| MCM531 | BL21 PL.2-mKKDyI, neo$^R$ looped out | MCM521 |

TABLE 4

Primer sequences

| Primer name | Sequence (5'→3') |
|---|---|
| MCM120 | aaagtagccgaagatgacggtttgtcacatggagttggcag gatgtttgattaaaagcAATTAACCCTCACTAAAGGGCGG (SEQ ID NO: 32) |
| MCM224 | taaatcttacccggcgcagaacaggataccatgttttttta cctcctttgcaccttcatggtggtcagtgcgtcctgctgat gtgctcagtatcaccgccagtggtatttaNgtcaacaccgc cagagataatttatcaccgcagatggttatctgtatgtttt ttatatgaatttaatacgactcactatagggctcg (SEQ ID NO: 33) |
| GB-DW | aaagaccgaccaagcgacgtctga (SEQ ID NO: 34) |
| MCM208 | GCTCTGAATAGTGATAGAGTCA (SEQ ID NO: 35) |

The assemblies integrated into the chromosomes of strains MCM518-MCM521 include new P$_L$ promoters derived from bacteriophage lambda (λ) and the very beginning of the mMVK ORF, with sequences from the Gene Bridges FRT-gb2-Cm-FRT cassette integrated upstream of the promoter/mMVK assembly, as well as the remainder of the mMVK ORF followed by the rest of the lower MVA pathway integron from strain MCM508.

Promoter/mMVK sequence integrated into
MCM518 (SEQ ID NO: 36):
aaagaccgaccaagcgacgtctgagagctccctggcgaattcggtacca
ataaaagagctttattttcatgatctgtgttggttttgtgtgcggc
gcggaagttcctattctctagaaagtataggaacttcctcgagccctat
agtgagtcgtattaaattcatataaaaaacatacagataaccatctgcg
gtgataaattatctctggcggtgttgacataaataccactggcggtgat
actgagcacatcagcaggacgcactgaccaccatgaaggtgcaaaggag
gtaaaaaaacatggtatcctgttctgcgccgggtaagatttacctgttc
ggtgaacacgccgtagtttatggcgaaactgcaattgcgtgtgcggtgg
aactgcgtacccgtgttcgcgcggaactcaatgactctatcactattca
gagc

```
Promoter/mMVK sequence integrated into
MCM519 (SEQ ID NO: 37):
aaagaccgaccaagcgacgtctgagagctccctggcgaattcggtacca ataaaagagctttattttcatgatctgtgtgttggttttttgtgtgcggc gcggaagttcctattctctagagtataggaacttcctcgagccetatag tgagtcgtattaaattcatataaaaaacatacagataaccatctgeggg ataaattatctctggcggtgttgacctaaataccactggcggtgatact ga2cacatcagcaggac2cactgaccaccatgaa2gt2caaaggaggta aaaaaacatggtatcctgttctgcgccgggtaagatttacctgttcggt gaacacgccgtagtttatggcgaaactgcaattgcgtgtgcggtggaac tgcgtacccgtgttcgcgcggaactcaatgactctatcactattcagagc Promoter/mMVK sequence integrated into
MCM520 (SEQ ID NO: 38):
aaagaccgaccaagcgacgtctgagagctccctggcgaattcggtacca ataaaagagctttattttcatgatctgtgtgttggttttttgtgtgcggc gcggaagttcctattctctagaaagtataggaacttcctcgagccctat agtgagtcgtattaaattcatataaaaaacatacagataaccatctgcg gtgataaattatctctggcggtgttgacctaaataccactggcggtgat actgagcacatcagcaggacgcactgaccaccatgaaggtgcaaggta aaaaaacatggtatcctgttctgcgccgggtaagattacctgttcggtg aacacgccgtagtttatggcgaaactgcaattgcgtgtgcggtggaact gcgtacccgtgttcgcgcggaactcaatgactctatcactattcagagc Promoter/mMVK sequence integrated into
MCM521 (SEQ ID NO: 39):
aaagaccgaccaagcgacgtctgagagctccctggcgaattcggtacca ataaaagagctttattttcatgatctgtgtgttggttttttgtgtgcggc gcggaagttcctattctctagaaagtataggaacttcctcgagccctat agtgagtcgtattaaattcatataaaaaacatacagataaccatctgcg gtgataaattatctctggcggtgttgacgtaaataccactggcggtgat actgagcacatcagcaggacgcactgaccaccatgaaggtgcaaggag gtaaaaaaacatggtatcctgttctgcgccgggtaagatttacctgttc ggtgaacacgccgtagtttatggcgaaactgcaattgcgtgtgcggtgg aactgcgtacccgtgttcgcgcggaactcaatgactctatcactatta gagc
```

Next, *E. coli* strain DW199, an isoprene-producing *E. coli* strain harboring the truncated version of *P. alba* isoprene synthase (the MEA variant) under control of the PTrc promoter, was constructed.

The plasmid harboring truncated *P. alba* isoprene synthase (IspS) was constructed by Quikchange™ (Agilent Technologies, Stratagene Products Division, La Jolla, Calif.) PCR mutagenesis from the template pEWL244 (also referred to as pTrc-*P. alba*(MEA)-mMVK (the construction of which is described in Example 10 of U.S. patent application Ser. No. 12/335,071, which is incorporated herein by reference in its entirety). The PCR reaction contained the following components: 1 µl pEWL244 (encoding pTrc *P. alba*-mMVK), 5 µl 10×PfuUltra High Fidelity buffer, 1 µl 100 mM dNTPs, 1 µl 50 µM QC EWL244 MEA F primer (SEQ ID NO: 40), 1 µl 50 µM QC EWL244 MEA R primer (SEQ NO:41), 2 µl DMSO, 1 µl PfuUltra High Fidelity polymerase (Agilent Technologies, Stratagene Products Division, La Jolla, Calif.), and 39 µl diH₂O. The PCR reaction was cycled as follows: 95° C./1 minute; and 18 cycles of 95° C./30 seconds, 55° C./1 minute, 68° C./7.3 minutes. The reaction was then cooled to 4° C.

The PCR product was visualized by gel electrophoresis using an E-gel (Invitrogen, Carlsbad, Calif.), and then treated with 1 µl DpnI restriction endonuclease (Roche, South San Francisco, Calif.) for three hours at 37° C. Ten µl of the PCR product were then de-salted using a microdialysis membrane MilliPore, Billerica, Mass.) and transformed into electrocompetent *E. coli* strain MCM531 (prepared as described above) using standard molecular biology techniques. Cells were recovered in one ml of LB medium for 1.5 hours at 30° C., plated onto LB-agar plates containing 50 µg/ml carbenicillin and 5 mM mevalonic acid, and then incubated overnight at 37° C. The next day, positive colonies (of strain DW195, see below) were selected for growth, plasmid purification (Qiagen, Valencia, Calif.), confirmed by DNA sequencing (Quintara Biosciences, Berkeley, Calif.) with the primers listed below. The final plasmid, pDW34 (FIG. 19A-D; SEQ ID NO:156), was confirmed to carry the open reading frame that encodes the truncated version of *P. alba* IspS.

Strain DW199 was generated by transformation of pDW34 and MCM82 (the construction of which is described in Example 8 of U.S. patent application Ser. No. 12/335,071, which is incorporated herein by reference in its entirety) into electrocompetent MCM531 (prepared as described above). Cells were recovered in 1 ml of LB medium for 1 hour at 37° C., plated on LB agar plates containing 50 µg/ml spectinomycin and 50 µg/ml carbenicillin, and then incubated overnight at 37'C. The next day, antibiotic resistant colonies of strain DW199 were chosen for further study.

TABLE 5

Primers

| Primer Name | Sequence (5'→3') |
|---|---|
| QC EWL244 MEA F | gaggaataaaccatggaagctcgtcgttc (SEQ ID NO: 40) |
| QC EWL244 MEA R | agaacgacgagcttccatggtttattcctc (SEQ ID NO: 41) |
| EL-1006 | gacagcttatcatcgactgcacg (SEQ ID NO: 42) |
| EL-1000 | gcactgtctttccgtctgctgc (SEQ ID NO: 43) |
| A-rev | ctcgtacaggctcaggatag (SEQ ID NO: 44) |
| A-rev-2 | ttacgtcccaacgctcaact (SEQ ID NO: 45) |
| QB1493 | cttcggcaacgcatggaaat (SEQ ID NO: 46) |
| MCM208 | gctctgaatagtgatagagtca (SEQ ID NO: 35) |
| MCM66 (aka pTrc Reverse) | ccaggcaaattctgttttatcag (SEQ ID NO: 47) |

TABLE 6

Strains

| Strain | Background | Plasmid | Resistance | Genotype |
|---|---|---|---|---|
| DW195 | MCM531 | pDW34 | Carb | BL21 (Novagen) PL.2mKKDyI, pTrc-P. alba(MEA)-mMVK |
| DW199 | MCM531 | pDW34 MCM82 | Carb/Spec | BL21 (Novagen) PL.2mKKDyI, pTrc-P. alba(MEA)-mMVK, pCL pTrc-Upper |

This example describes the construction of E. coli strains CMP215, CMP258, and CMP234, all of which are derived from BL21 transduced with P1 phage containing E. coli MG1655 genomic DNA and selected for recombination of a 17,257 bp piece present in MG1655 but absent in BL21 and BL21 (DE3).

Figure 20:
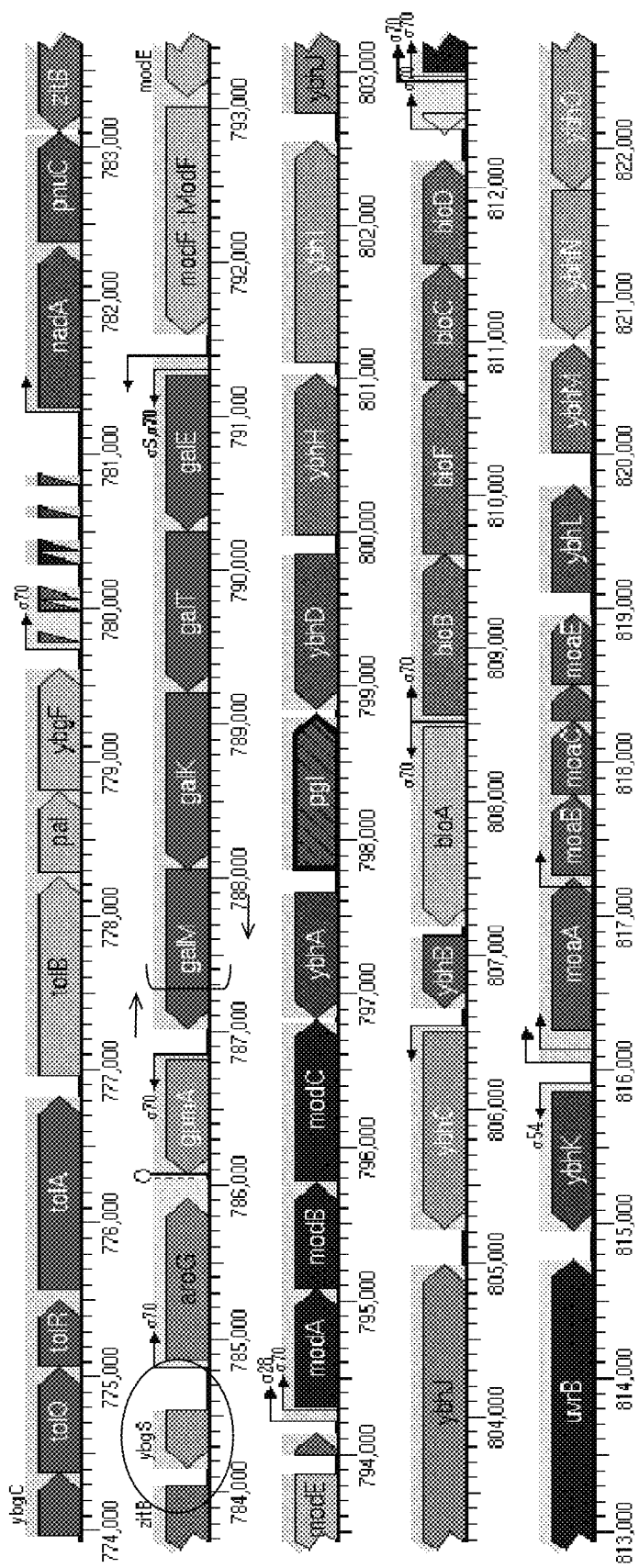
FIG. 20 shows the chromosomal organization of E. coli K12 strain MG1655 around the pgl locus. The region deleted in E. coli BL21 (DE3) compared to E. coli K12 MG655 and restored in strains CMP215 and CMP258 is shown in brackets. The predicted ORF of the ybgS gene is circled. A forward arrow (→) indicates the annealing site of the galMF primer (SEQ ID NO:8). A reverse arrow (←) indicates the annealing site of the galMR primer (SEQ ID NO:9).

A P1 lysate was made of strain JW0736, in which the ybgS gene was replaced with a kanamycin resistance gene ("Kan$^R$")(i.e., ybgS::Kan$^R$ mutation) from the Keio collection (Baba et al. 2006). That lysate was used to infect strain MCM531 (described above), producing strain CMP215. The genotype of CMP215 was confirmed by PCR using primers galM R (5'-GTC AGG CTG GAA TAC TCT TCG-3'; SEQ ID NO:9) and galM F (5'-GAC GCT TTC GCC AAG TCA GG-3'; SEQ ID NO:8). Those primers anneal to the galM gene, as shown on FIG. 20, but only produce a PCR product from E. coli BL21 (DE3) chromosomal DNA having the 17,257 bp deletion.

Integration of the 17,257 bp fragment following P1 transduction was verified by PCR with the following protocol. One bacterial colony was seined in 30 µl H$_2$O and heated to 95"C for 5 minutes. The resulting solution was spun down and 2 µl of the supernatant used as template in the following PCR reaction: 2 µl colony in H$_2$O, 5 µl Herculase® Buffer, 1 µl 100 mM dNTPs, 1 µl 10 µM Forward primer, 1 µl 10 µM Reverse primer, 0.5 µl of Herculase® Enhanced DNA Polymerase (Agilent Technologies, Stratagene Products Division, La Jolla, Calif.), and 39.5 µl diH$_2$O. The PCR reaction was cycled in a PCR Express Thermal Cycler (Thermo Hybaid, Franklin, Mass.) as follows: 95° C./2 minutes; 30 cycles of 95° C./30 seconds, 52° C./30 seconds, 72° C./60 seconds; and 72° C./7 minutes. The reaction was then cooled to 4° C. The annealing temperature of 52° C. was 3° C. lower than the lower T$^m$ of the primer pair. The size of the resulting PCR fragment was determined on a pre-cast 0.8% E-gel® (Invitrogen Carlsbad, Calif.) using DNA Molecular Weight Marker X (75-12,216 bp) (Roche Diagnostics, Mannheim, Germany) as size marker. Successful transduction was also confirmed by the ability of strain GMP215 to grow on galactose.

Alternatively, a lysate of E. coli MG1655 was used to transduce strain MCM531 (described above). A colony selected on M9 medium supplemented with 0.4% (w/v) galactose was named CMP258. Presence of the 17,257 bp region containing pgl was confirmed by PCR using primers galM R (SEQ ID NO:9) and galM F (SEQ ID NO:8), essentially as described above.

Strain CMP215 was cotransformed by electroporation with plasmids pCLPtrcUpperPathway expressing mvaE and mvaS (prepared as described in Example 8 of U.S. patent application Ser. No. 12/335,071, which is incorporated herein by reference in its entirety) and pDW34 (containing a truncated P. alba isoprene synthase M. mazei mevalonate kinase, as described above). Transformants were selected on LB agar plates including 50 µg/ml carbenicillin+50 µg/ml spectinomycin. One colony was picked and named CMP234.

II. Fermentation Using an MBR Increases Isoprene Production

Increased Production of Isoprene:

15 L fed-batch fermentation with E. coli strain CMP234 in a membrane bioreactor system. E. coli BL21 (DE3) strain CMP234 (constructed as described above) overexpresses M. mazei mevalonate kinase and P. alba isoprene synthase and contains an integrated copy of 6-phosphogluconolactonase (PGL) derived from E. coli K12 strain MG1655. Isoprene was produced by CMP234 cells grown in fed-batch culture at 15-L scale in a membrane bioreactor (MBR) in minimal medium.

Medium Recipe (Per L):

7.5 g K$_2$HPO$_4$, 2 g MgSO$_4$*7H$_2$O, 2 g citric acid monohydrate, 0.3 g ferric ammonium citrate, 0.5 g yeast extract, and 1 mL 1000× Modified Trace Metal Solution (recipe below) were dissolved together in distilled, deionized water (diH$_2$O) and heat-sterilized at 12.3° C. for 20 minutes. The pH was adjusted to 7.0 with 28% ammonium hydroxide brought up to final volume with sterile water. 10 g glucose, 8 mL Vitamin Solution (recipe below) and appropriate antibiotics were added after sterilization and pH adjustment.

1000× Modified Trace Metal Solution (Per L):

40 g Citric Acid*H$_2$O, 30 g MnSO$_4$*H$_2$O, 10 g NaCl, 1 g FeSO$_4$*7H$_2$, 1 g CoCl$_2$*6H$_2$O, 1 g ZnSO$_4$*7H$_2$O, 100 mg CuSO$_4$*5H$_2$O, 100 mg H$_3$BO$_3$, and 100 mg NaMoO$_4$*2H$_2$O were dissolved one at a time in diH$_2$O. The pH was adjusted to 3.0 with HCl/NaOH, and the solution was brought up to final volume and sterilized using a 0.2-µm filter.

Vitamin Solution (Per L):

1 g Thiamine hydrochloride, 1 g D-(+)-biotin, 1 g nicotinic acid, 4.8 g D-pantothenic acid, and 4.0 g pyridoxine hydrochloride were dissolved one at a time in diH$_2$O. The pH was adjusted to 3.0 with HCl/NaoH, and the solution was brought up to final volume and sterilized using a 0.22-µm filter.

Macro Salt Solution (Per L):

296 g MgSO$_4$*7O, 296 g citric acid monohydrate, and 49.6 g ferric ammonium citrate were dissolved together in water, brought up to final volume, and sterilized using a 0.22-µm filter.

Glucose Feed Solution (Per kg):

0.57 kg Glucose, 0.38 kg diH$_2$O, 7.5 g K$_2$HPO$_4$, and 10 g 100% Foamblast were mixed together and autoclaved. 5.6 mL Macro Salt Solution, 0.8 mL 1000× Modified Trace Metal Solution, and 6.7 mL Vitamin Solution were added after the solution had cooled to 25° C.

Fermentation was performed in a 15-L bioreactor with E. coli BL21 cells expressing the upper mevalonic acid (MVA) pathway (pCL Upper), the integrated lower MVA pathway (PL.2 mKKDyI), mevalonate kinase from M. mazei and truncated isoprene synthase from P. alba (pTrcAlba(MEA) mMVK (pDW34)), and containing a restored chromosomal pgl gene (t ybgS::Kan) (strain name CMP234).

This example was carried out to monitor isoprene formation from glucose at the desired fermentation pH 7.0 and temperature 34° C. in an MBR, using a separate "non-MBR"

membrane-free reactor as a control. A frozen vial of E. coli BL21 strain CMP234 was thawed and inoculated into tryptone-yeast extract medium for each reactor. After the inoculum grew to optical density 1.0, measured at 550 nm (OD), 500 mL was used to inoculate a 15-L reactor and bring the initial tank volume to 5 L.

Figure 21:
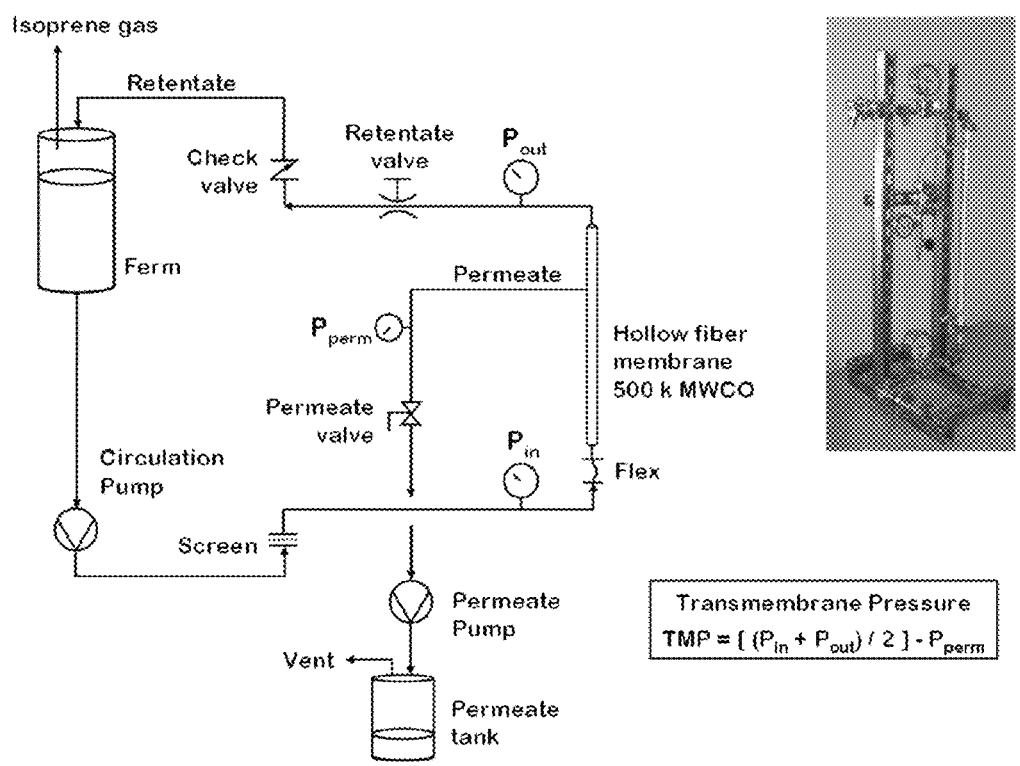
FIG. 21 shows a diagram of an MBR system used in 15-L scale fermentation to make isoprene gas and to collect permeate containing spent media. A broth circulation loop delivers fermentor broth to a tangential flow membrane filter. The membrane, a GE Healthcare Xampler™ Ultrafiltration Cartridge 500,000 NMWC, 1 mm fiber inner diameter, 60 cm long, 850 sq cm area, hollow fiber membrane, was chosen based on its suitability for high cell density E. coli broth. The hold-up volume of the broth circulation loop, including the membrane, was roughly 250 mL. The part of the apparatus comprising the loop components, but excluding the circulation pump, was autoclaved before use. The circulation and permeate pumps were peristaltic tubing pumps. A pressure gauge was used to measure $P_{in}$, the inlet pressure of the membrane, to ensure the pressure tolerance of the membrane (roughly 2 bar) was not exceeded, TMP, defined in the diagram, is a rough measure of the force that drives permeation. A positive TMP was needed to collect permeate.
Figure 22:
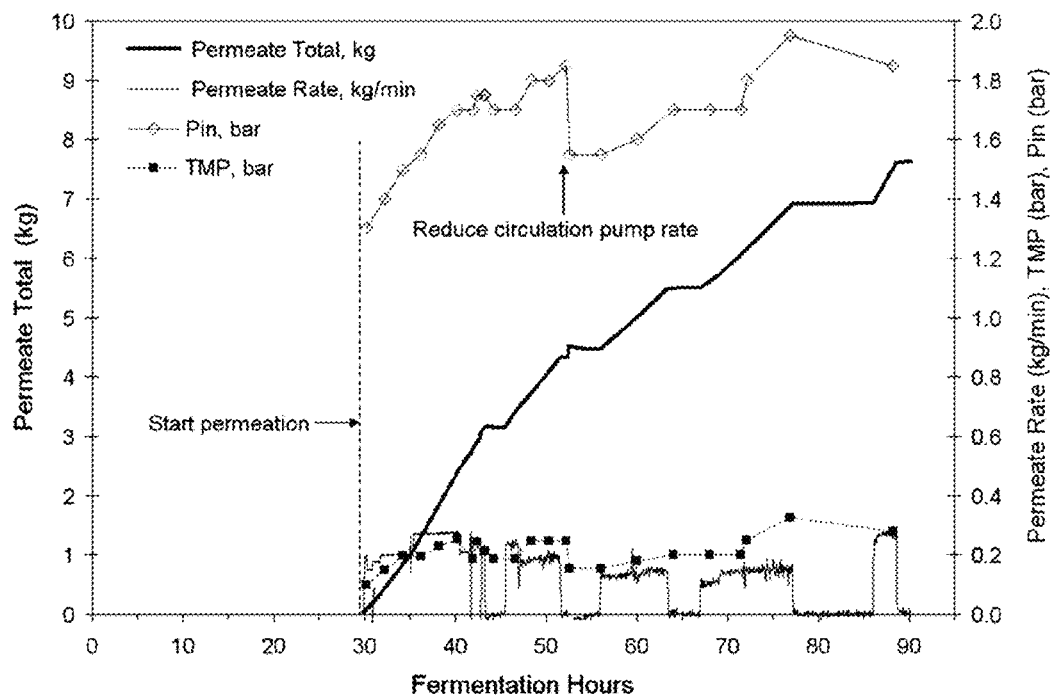
FIG. 22 shows the operational parameters of an MBR during a 15-L scale run. $P_{in}$ and TMP were manipulated mainly by Changing circulation pump rate, e.g. a reduction in $P_{in}$ of around 20% was achieved at 50 h by lowering circulation pump rate by around 20%. TMP was steady at about 0.2 bar during permeation. Due to flow dynamics within the membrane cartridge, TMP was never zero, even when the permeate rate was zero. The permeate rate was controlled by adjusting permeate pump rate. Around 8 kg of permeate was collected in this example.

FIG. 21 shows a membrane bioreactor including a tangential flow filter set up with a 15-L bioreactor growing E. coli strain CMP234. FIG. 22 shows the operational parameters of an MBR during a 15-L scale fermentation run.

The feed solution was added at an exponential rate until a top feed rate of 6.4 g/minute was reached, Glucose was then fed to meet metabolic demands at rates less than or equal to 6.4 g/minute. The total amount of glucose delivered to the MBR reactor during the 88 h fermentation was 9.2 kg, compared to 8.4 kg of glucose delivered to the non-MBR control reactor. Induction of protein expression was achieved by adding isopropyl-beta-D-1-thiogalactopyranoside (IPTG). The IPTG concentration was brought to 110 μM when the OD reached 5 and raised to 200 μM when the OD reached 100.

Figure 23:
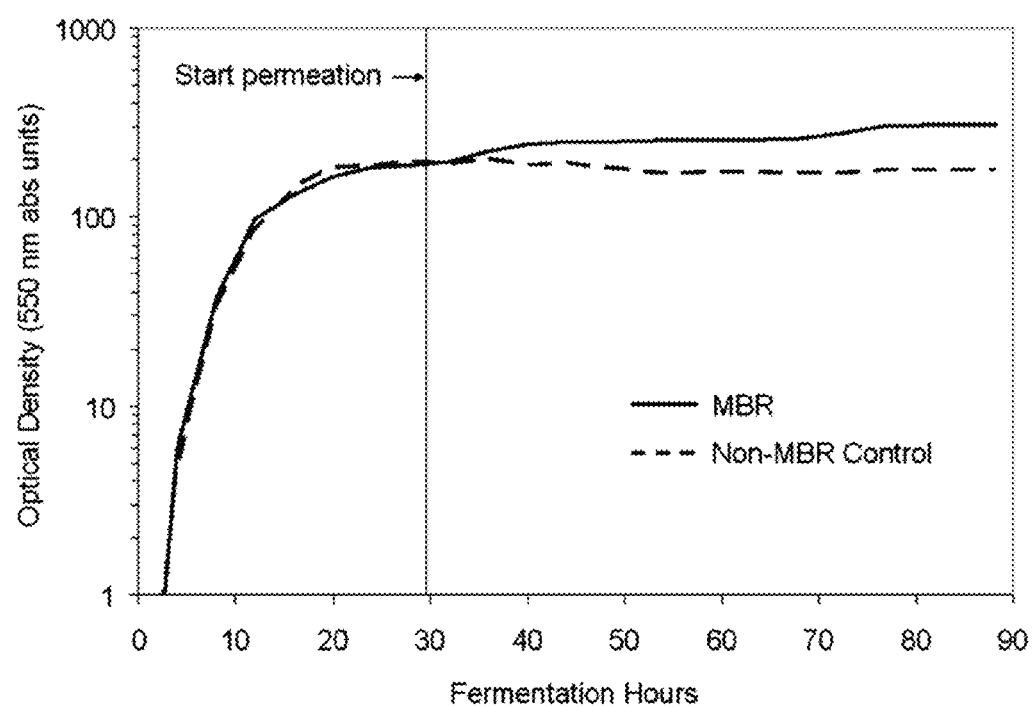
FIG. 23 shows a plot of optical density (OD) in reactor broth in a 15-L scale fermentation for an MBR fermentation and a non-MBR control. The OD during MBR operation rose from 195 to 305, whereas the OD of the non-MBR control declined from 195 to 175 during the same period. OD was measured by the 550-nm absorbance of a broth sample. Higher OD indicates a higher concentration of cells, cell debris, and other suspended solids. The fermentation method is described in Example 4.
Figure 28:
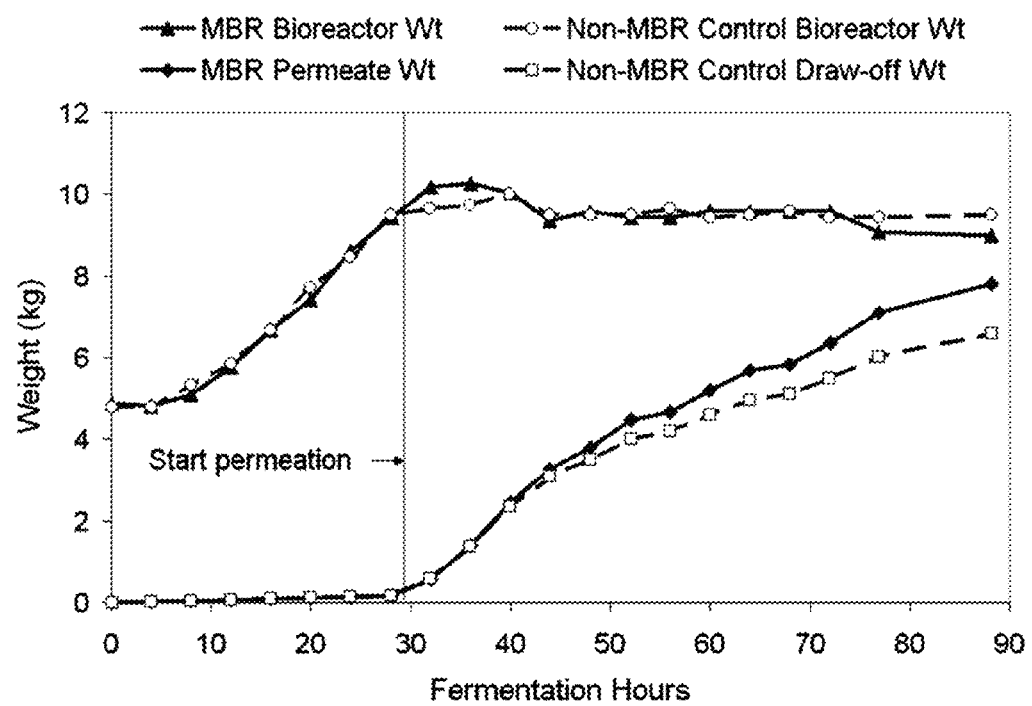
FIG. 28 shows a plot of bioreactor broth weights in 15-L scale run fermentor runs. To maintain reactor weight, a membrane permeate was extracted in the MBR run, while whole broth (draw-off) was removed in the non-MBR control run. In this example, around 8 kg of permeate was collected in the MBR run, and around 7 kg of draw-off, in the non-MBR control. The fermentation method is described in Example 4.

Clarified fermentation broth (permeate) was removed using the MBR (FIG. 21) starting at 30 hours of fermentation in amounts necessary to maintain reactor weight at 9.7 kg (FIG. 28; 7.8 kg permeate removed in 88 hours of fermentation). Whole broth including cells was removed starting at 30 hours of fermentation from the non-MBR control reactor in amounts necessary to maintain reactor weight at 9.7 kg (FIG. 28; 6.6 kg whole broth removed in 88 hours of fermentation). OD profiles within the MBR and non-MBR reactors over time are shown in FIG. 23.

Figure 24:
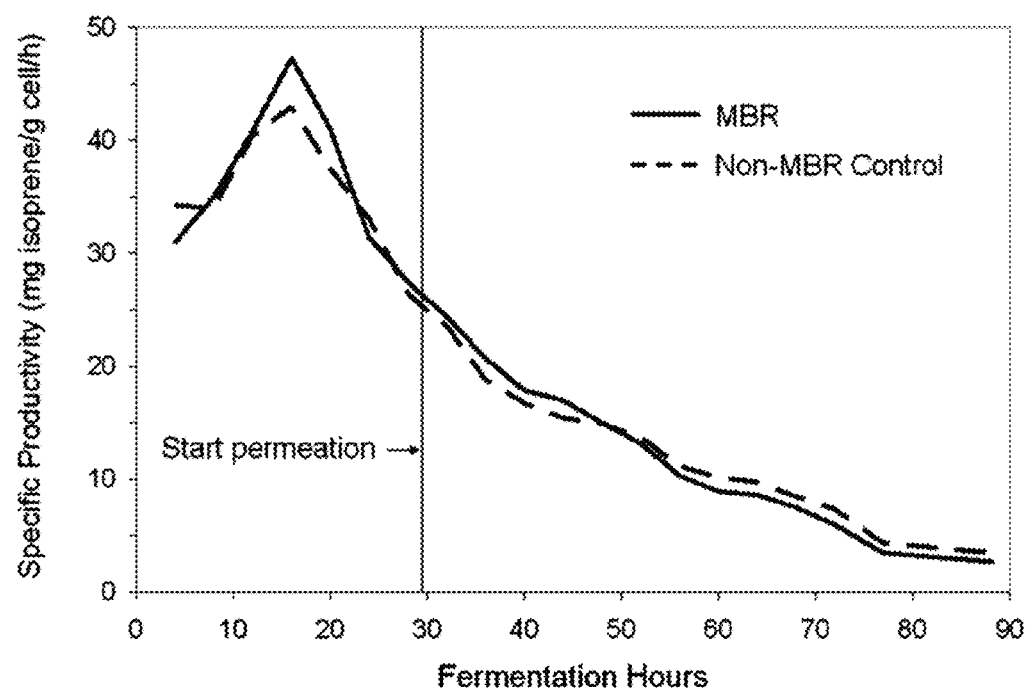
FIG. 24 shows a plot of isoprene specific productivity in a 15-L scale run for an MBR fermentation and a non-MBR control. The MBR did not change the specific productivity of cells compared to that of a non-MBR control. The specific productivity is the rate of isoprene production on a cell mass basis. The similarity between the MBR and the non-MBR control runs suggests the MBR operation did not significantly alter cell physiology. The fermentation method is described in Example 4. Specific productivity was calculated using equations in Example 4.
Figure 25:
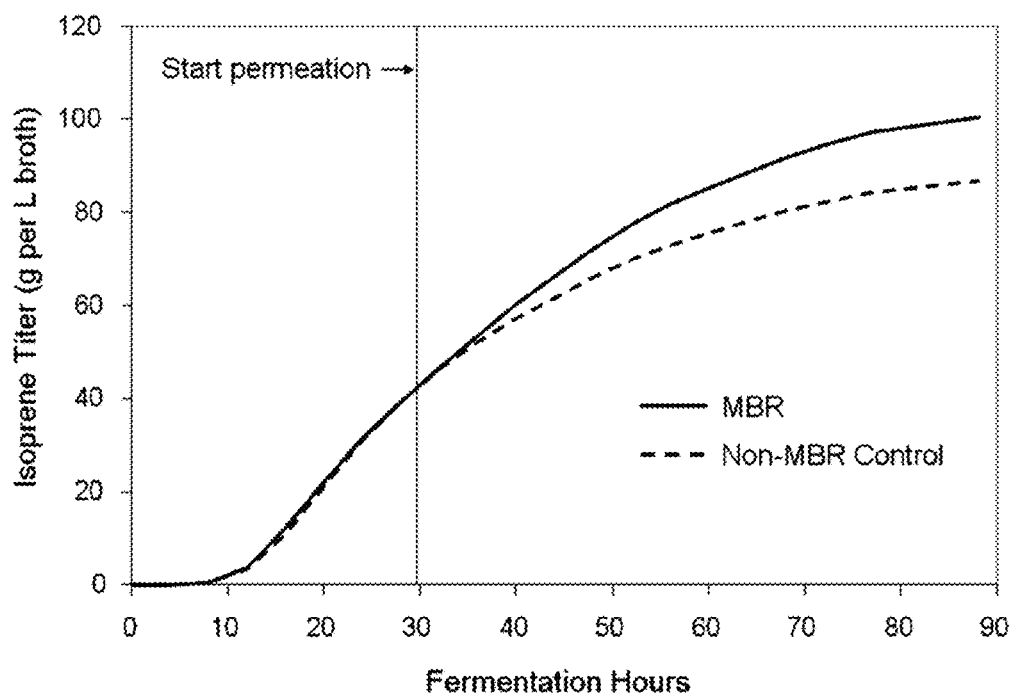
FIG. 25 shows a plot of isoprene gas titer in a 15-L scale run for an MBR fermentation and a non-MBR control. The MBR increased titer by around 16% compared to a non-MBR control. A higher titer means more isoprene is produced per, reactor volume, which leads to a lower production cost. The fermentation method is described in Example 4.
Figure 26:
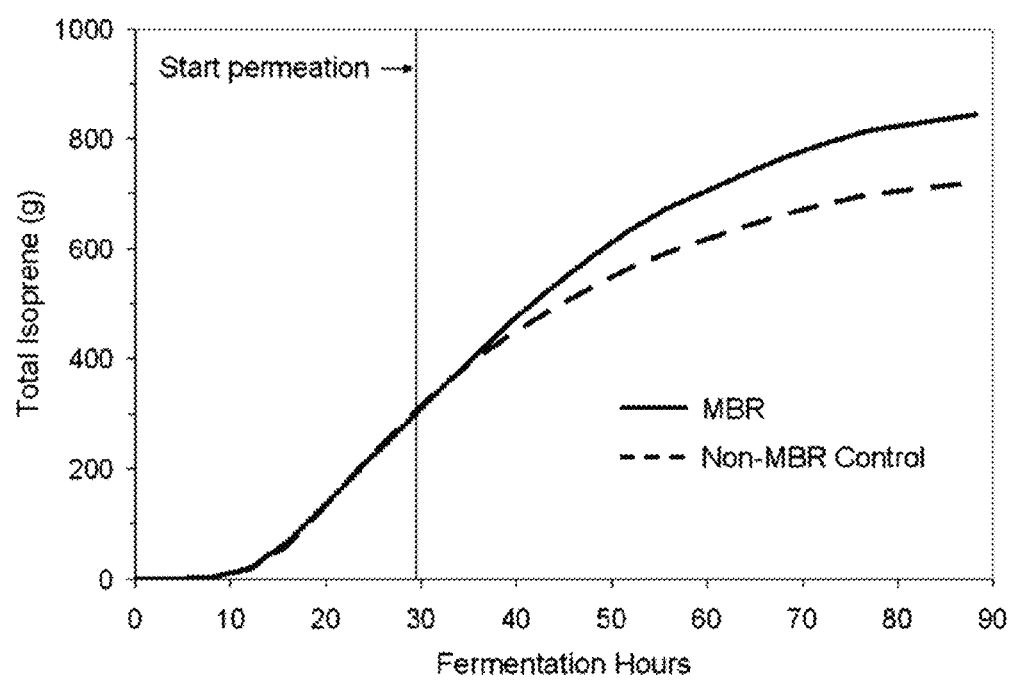
FIG. 26 shows a plot of total isoprene gas production in a 15-L scale run for an MBR fermentation and a non-MBR control. The MBR increased total production of isoprene gas by around 17% compared to a non-MBR control over the same fermentation time. The fermentation method is described in Example 4. The equations used to calculate total isoprene production are described in Example 4.
Figure 27:
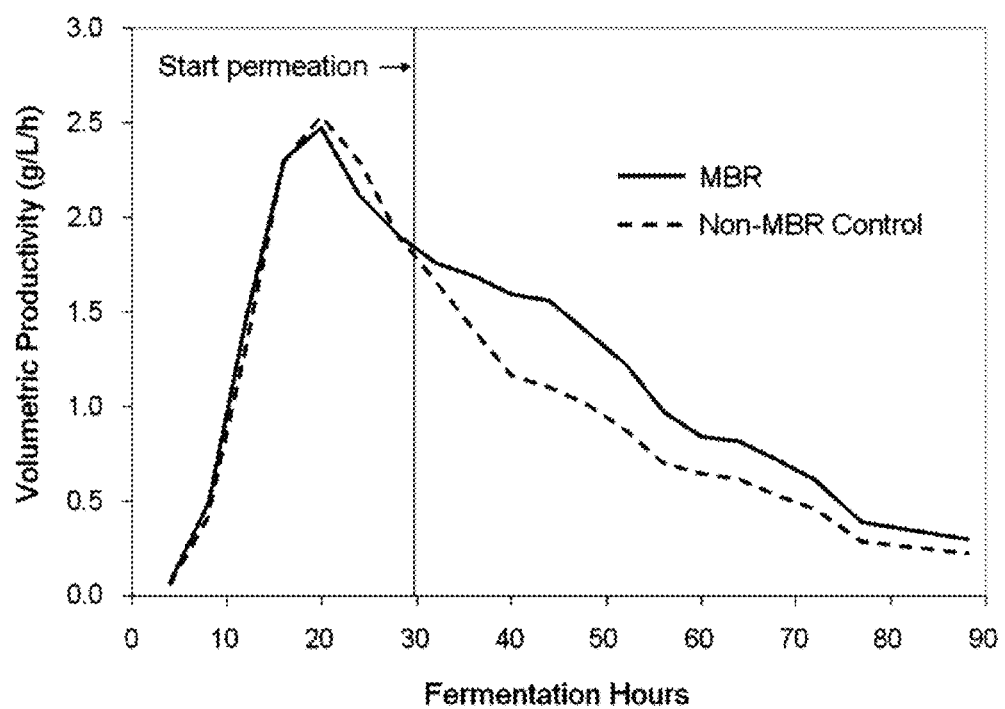
FIG. 27 shows a plot of volumetric productivity of isoprene in a 15-L scale run for an MBR fermentation and a non-MBR control. The volumetric productivity was higher during operation of the MBR compared to that of the non-MBR control during the same period. A higher volumetric productivity means a higher rate of isoprene production on a volume basis, which leads to lower production cost. The fermentation method is described in Example 4. Volumetric productivity was calculated using equations in Example 4.

The isoprene level in reactor off-gas was determined using a Hiden mass spectrometer. Isoprene titer increased during fermentation to 100.5 g/L, at 88 hours in the MBR and to 84.3 g/L in the non-MBR control (FIG. 25). Total isoprene produced during the 88 hour fermentation was 843.9 g in the MBR, compared to 721.0 g in the non-MBR control. The time course of production is shown in FIG. 26. The time course of specific productivity shows very similar profiles for both reactors: the MBR did not seem to dramatically alter cell physiology (FIG. 24). The molar yield of isoprene from glucose carbon during fermentation was 20.1% at SS hours in the MBR, compared to 18.8% at 88 hours in the non-MBR control. The weight-% yield of isoprene from glucose was 9.3% at 88 hours in the MBR, compared to 8.7% at 88 hours in the non-MBR control.

Isoprene evolution rate, isoprene titer, total isoprene, volumetric productivity, and specific productivity were calculated according to the equations below.

$$HGER = \frac{Airflow}{Offgas\,N2} \cdot Supply\,N2 \cdot Offgas\,HG \cdot \frac{(60\,min/h)}{(100\% \cdot 24.14)} \cdot \frac{1.05}{Ferm\,Wt}$$

$$Isoprene\,Titer = 68.117 \cdot \int (HGER)dt$$

$$Total\,Isoprene = \int (Airflow \cdot HG\,\mu g/L \cdot 60\,min/h \cdot 1\,g/1000000\,\mu g)dt$$

$$Vol\,Prod = \frac{d}{dt} \cdot (Isoprene\,Titer) \cong \frac{(Isoprene\,Titer)_{n+1} - (Isoprene\,Titer)_{n-1}}{(t)_{n+1} - (t)_{n-1}}$$

$$Sp\,Prod = \frac{Vol\,Prod \cdot 1000\,mg/g \cdot 2.7}{OD}$$

where
HGER=total isoprene evolution rate per vol. broth [=] mol/L/h
Airflow=air flow rate into reactor [=] std L/min
Offgas N2=nitrogen conc. in reactor off-gas [=] mol %
Supply N2=nitrogen conc. in air entering reactor [=] mol %
Offgas HG=isoprene conc. in reactor off-gas [=] mol %
24.14=ideal gas conversion at 1 atm, 21.1° C. [=] L/mol
1.05=broth density [=] kg/L
Ferm Wt=reactor broth wt [=] kg
Isoprene Titer=isoprene produced on a broth volume basis [=] g/L
t=time [=] h
n=time interval designation [=] unitless
68.117=isoprene molecular wt [=] g/mol
Total Isoprene=total isoprene produced L [=] g
HG μg/L=isoprene conc. in reactor off-gas [=] μg/L
Vol Prod=isoprene volumetric productivity [=] g/L/h
Sp Prod=isoprene specific productivity [=] mg isopr/g cell/h
OD=optical density of broth at 550 nm [=] abs. unit
2.7=empirical conversion of OD to cell conc. [=] abs. unit·L/g cell
and where integrals may be estimated by the trapezoidal rule.

Example 5

Recycled Permeate from an MBR Improves Isoprene Specific Productivity

Recycling permeate from MBR. Medium from 15-L scale fermentations of the isoprene producing E. coli strain DW202 (strain DW199 (produced as described above)+pBBR gi1.5-pgl (produced as described above)), carrying the MVA pathway (upper MVA pathway from E. faecalis and integrated lower MVA pathway from S. cerevisiae, plus MVK from M. mazei) and isoprene synthase (from P. alba), was isolated from the bioreactors 38 hours after inoculation, 15-L scale fermentations were performed as described above. Cell mass was quickly removed by centrifugation. The remaining medium (analogous to permeate) was ultracentrifuged at 50,000 rpm for 30 minutes at 4° C. to ensure that all solids were removed. The resulting clarified, spent medium was diluted into fresh TM3 minimal medium at concentrations ranging from 0 to 30%.

The E. coli strain MCM597 col/BL21 (DE3)pLysS expressing a truncated version of P. alba isoprene synthase (the MEA variant), E. coli DXS and S. cerevisiae IDI (prepared as described in Example 7 of U.S. patent application Ser. No. 12/335,071, which is hereby incorporated herein by reference in its entirety) was grown overnight and inoculated in the medium. Protein expression in strain MCM597 was induced with 200 μM IPTG and the induced strain was grown at 30° C. in a microfermentor. Culture growth (i.e., cell mass) was followed by measuring optical density at 600 nm using a plate reader. Isoprene production was followed by GC analysis of 100 μL headspace samples taken at 4 hours after inoculation. Specific productivity was calculated as the isoprene production divided by the optical density.

Figure 29:
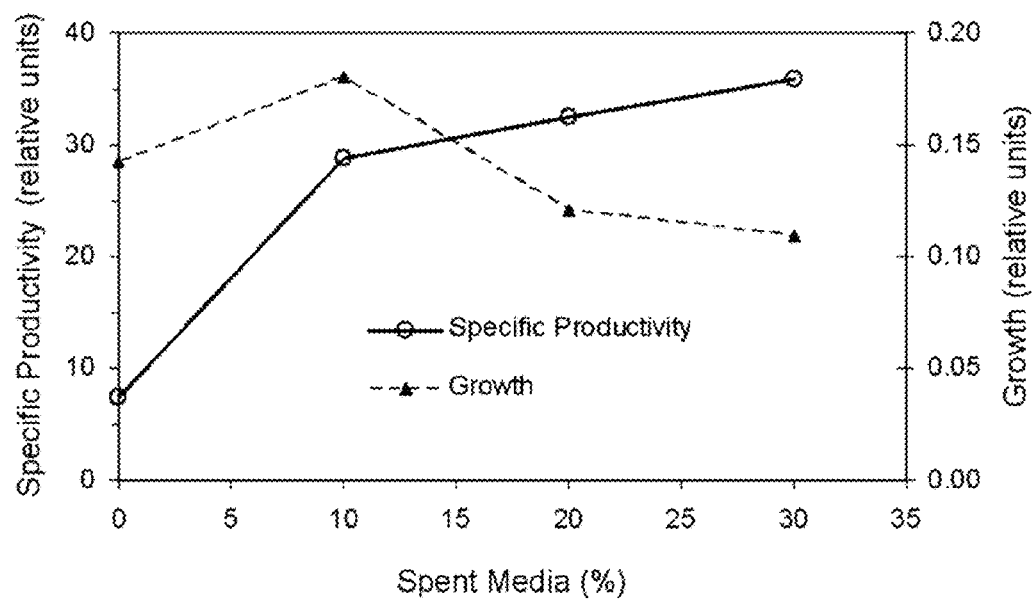
FIG. 29 shows a plot of the increase in specific productivity of isoprene gas in a fed-batch culture by supplementing with spent media: More than a three-fold increase in isoprene specific productivity was achieved by supplementing the culture medium with 30% by weight of spent media (clarified broth supernatant), despite around 25% lesser growth. A higher specific productivity means that more isoprene is produced per cell mass per time. The result suggests that MBR permeate, which contains spent media, can be used to enhance specific productivity of cells, thereby reducing production cost. The experimental method is described in Example 5.

A greater than three-fold increase in isoprene specific productivity was achieved by supplementing the culture medium with 30% (w/w) of spent media (i.e., permeate), despite about 25% less growth (FIG. 29). A higher specific productivity means that more isoprene is produced per cell mass per time. The result suggests that MBR permeate containing spent medium can be used to enhance specific, productivity of isoprene-producing cells, thereby reducing production costs.

The headings provided herein are not limitations of the various aspects or aspects of the invention which can be had by reference to the specification as a whole.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of producing isoprene, the method comprising:
   (a) culturing cells comprising a heterologous nucleic acid encoding an isoprene synthase polypeptide under suitable culture conditions for the production of isoprene;
   (b) removing a portion of the culture;
   (c) filtering the removed portion of the culture to produce a permeate and a retentate;
   (d) returning the retentate to the culture; and
   (e) producing isoprene;
   wherein the cultured cells undergoing steps (b), (c), and (d) either produce isoprene at a higher titer, or have greater average volumetric productivity of isoprene than the same cells cultured without undergoing steps (b), (c), and (d).

2. The method of claim 1, wherein the filtering is by tangential flow filtration.

3. The method of claim 1, wherein the cells produce isoprene at a titer of greater than 40 g/L.

4. The method of claim 1, wherein the cells produce isoprene at a titer between 40 g/L and 100 g/L.

5. The method of claim 1, wherein the cells have an average volumetric productivity of isoprene of greater than 500 $mg/L_{broth}/hr$.

6. The method of claim 1, wherein the cells have an average volumetric productivity of isoprene between 500 $mg/L_{broth}/hr$ and 2,000 $mg/L_{broth}/hr$.

7. The method of claim 1, further comprising a step of recycling the permeate back into the same cell culture or into another cell culture, wherein the cells cultured in the presence of recycled permeate have greater average specific productivity of isoprene than the same cells cultured in the absence of recycled permeate.

8. The method of claim 7, wherein the cells have about two times the average specific productivity of isoprene than the same cells cultured in the absence of recycled permeate.

9. The method of claim 1, wherein the portion of the culture is removed continuously.

10. The method of claim 1, wherein the portion of the culture is removed discontinuously.

11. The method of claim 1, wherein the isoprene synthase polypeptide is a plant isoprene synthase polypeptide.

12. The method of claim 1, wherein the cells further comprise a heterologous nucleic acid encoding an isopentyl-diphosphate isomerase (IDI) polypeptide.

13. The method of claim 12, wherein the cells further comprise a chromosomal copy of an endogenous nucleic acid encoding an IDI polypeptide.

14. The method of claim 12, wherein the cells further comprise a heterologous nucleic acid encoding a DXS polypeptide.

15. The method of claim 12, wherein the cells further comprise a chromosomal copy of an endogenous nucleic acid encoding a DXS polypeptide.

16. The method of claim 12, wherein the cells further comprise one or more nucleic acids encoding an IDI polypeptide and a DXS polypeptide.

17. The method of claim 16, wherein one nucleic acid encodes the isoprene synthase polypeptide, IDI polypeptide, and DXS polypeptide.

18. The method of claim 17, wherein one plasmid encodes the isoprene synthase polypeptide, IDI polypeptide, and DXS polypeptide.

19. The method of claim 12, wherein the cells further comprise a heterologous nucleic acid encoding an MVA pathway polypeptide.

20. The method of claim 19, wherein the MVA pathway polypeptide is a mevalonate kinase (MVK) polypeptide.

21. The method of claim 20, wherein the MVK polypeptide is a polypeptide from the genus *Methanosarcina*.

22. The method of claim 21, wherein the *Methanosarcina* is *Methanosarcina mazei*.

23. The method of claim 11, wherein the isoprene synthase polypeptide is a naturally-occurring polypeptide from the genus *Pueraria*.

24. The method of claim 23, wherein the isoprene synthase polypeptide is a naturally-occurring polypeptide from *Pueraria montana*.

25. The method of claim 11, wherein the isoprene synthase polypeptide is a naturally-occurring polypeptide from the genus *Populus*.

26. The method of claim 25, wherein the isoprene synthase polypeptide is a naturally-occurring polypeptide from *Populus alba*.

27. The method of claim 26, wherein the cells further comprise a heterologous nucleic acid encoding an MVA pathway polypeptide.

28. The method of claim 27, wherein the MVA pathway polypeptide is a mevalonate kinase (MVK).

29. The method of claim 27, wherein the MVK is from the genus *Methanosarcina*.

30. The method of claim 29, wherein the MVK is from *Methanosarcina mazei*.

31. The method of claim 1, wherein the cells are bacterial cells.

32. The method of claim 31, wherein the cells are gram-positive bacterial cells or gram-negative bacterial cells.

33. The method of claim 32, wherein the cells are *Bacillus subtilis* cells, *Escherichia coli* or *Pantoea citrea* cells.

34. The method of claim 1, wherein the cells are fungal cells.

35. The method of claim 34, wherein the cells are *Trichoderma reesei* cells.

36. The method of claim 34, wherein the cells are yeast cells.

37. The method of claim 36, wherein the cells are *Saccharomyces cerevisiae* or *Yarrowia lipolytica* cells.

38. A method of producing isoprene, the method comprising:
   (a) culturing cells comprising a heterologous nucleic acid encoding an isoprene synthase polypeptide in a fermentor containing growth medium under suitable culture conditions for the production of isoprene;
   (b) removing a portion of the cell culture from the fermentor;
   (c) transferring the removed portion of the cell culture to a filter;
   (d) filtering the removed portion of the cell culture to form: (i) a permeate comprising spent growth medium; and (ii) a retentate comprising cells and other culture solids;
   (e) returning the retentate to the fermentor;
   (f) collecting the permeate; and
   (g) producing isoprene;
   wherein the cultured cells undergoing steps (b), (c), (d) and (e) either produce isoprene at a higher titer, or have greater average volumetric productivity of isoprene than the same cells cultured without undergoing steps (b), (c), (d) and (e).

39. The method of claim 38, wherein the fermentor and the filter are connected by a circulation loop and a circulation pump.

40. The method of claim 38, wherein the permeate is collected from the filter by a permeate collection outlet and a permeate pump and stored in a permeate collection tank.

41. The method of claim 40, wherein the permeate collection tank further comprises a vent to relieve pressure within the tank.

42. The method of claim 39, wherein the circulation pump is a peristaltic pump.

43. The method of claim 39, wherein the filter is a microfilter.

44. The method of claim 39, wherein the filter is an ultrafilter.

45. The method of claim 43, wherein the microfilter is a tangential flow filter.

46. The method of claim 45, wherein the tangential flow filter has a filter pore size between about 0.005 μm and about 100 μm.

47. The method of claim 46, wherein the tangential flow filter has a filter pore size between about 0.05 μm and about 10 μm.

48. The method of claim 44, wherein the ultrafilter is a tangential flow filter.

49. The method of claim 47, wherein the tangential flow filter has a nominal molecular weight cutoff (NMWC) greater than about 100,000.

50. The method of claim 45, further comprising the steps of (i) monitoring the inlet pressure of the filter with an inlet pressure gauge ($P_{in}$); (ii) monitoring the outlet pressure of the filter with an outlet pressure gauge ($P_{out}$); (iii) monitoring the pressure in the permeate collection outlet with a permeate pressure gauge ($P_{perm}$); and (iv) determining the transmembrane pressure (TMP) across the filter.

51. The method of claim 50, further comprising the step of maintaining positive TMP across the filter.

52. The method of claim 50, wherein the fermentor further comprises an isoprene collection outlet connected to an isoprene storage tank.

53. The method of claim 50, wherein the cells produce isoprene at a titer of greater than 40 g/L.

54. The method of claim 50, wherein the cells produce isoprene at a titer between 40 g/L and 100 g/L.

55. The method of claim 50, wherein the cells have an average volumetric productivity of isoprene of greater than 500 mg/$L_{broth}$/hr.

56. The method of claim 50, wherein the cells have an average volumetric productivity of isoprene between 500 mg/$L_{broth}$/hr and 2,000 mg/$L_{broth}$/hr.

57. The method of claim 50, further comprising the steps of sterilizing the collected permeate and recycling it back into the same fermentor or into another fermentor, wherein the cells cultured in the presence of recycled permeate have greater average specific productivity of isoprene than the same cells cultured in the absence of recycled permeate.

58. The method of claim 57, wherein the cells have about two times the average specific productivity of isoprene than the same cells cultured in the absence of recycled permeate.

59. The method of claim 57, wherein the cells have about a 10% increase in productivity.

60. The method of claim 38, wherein the portion of the culture is removed continuously.

61. The method of claim 38, wherein the portion of the culture is removed discontinuously.

62. The method of claim 38, wherein the isoprene synthase polypeptide is a plant isoprene synthase polypeptide.

63. The method of claim 38, wherein the cells further comprise a heterologous nucleic acid encoding an IDI polypeptide.

64. The method of claim 63, wherein the cells further comprise a chromosomal copy of an endogenous nucleic acid encoding an IDI polypeptide.

65. The method of claim 63, wherein the cells further comprise a heterologous nucleic acid encoding a DXS polypeptide.

66. The method of claim 63, wherein the cells further comprise a chromosomal copy of an endogenous nucleic acid encoding a DXS polypeptide.

67. The method of claim 63, wherein the cells further comprise one or more nucleic acids encoding an IDI polypeptide and a DXS polypeptide.

68. The method of claim 67, wherein one nucleic acid encodes the isoprene synthase polypeptide, IDI polypeptide, and DXS polypeptide.

69. The method of claim 68, wherein one plasmid encodes the isoprene synthase polypeptide, IDI polypeptide, and DXS polypeptide.

70. The method of claim 62, wherein the cells further comprise a heterologous nucleic acid encoding an MVA pathway polypeptide.

71. The method of claim 70, wherein the MVA pathway polypeptide is a mevalonate kinase (MVK) polypeptide.

72. The method of claim 71, wherein the MVK polypeptide is from the genus *Methanosarcina*.

73. The method of claim 72, wherein the MVK is from *Methanosarcina mazei*.

74. The method of claim 62, wherein the isoprene synthase polypeptide is a naturally-occurring polypeptide from the genus *Pueraria*.

75. The method of claim 74, wherein the isoprene synthase polypeptide is a naturally-occurring polypeptide from *Pueraria montana*.

76. The method of claim 62, wherein the isoprene synthase polypeptide is a naturally-occurring polypeptide from the genus *Populus*.

77. The method of claim 76, wherein the isoprene synthase polypeptide is a naturally-occurring polypeptide from *Populus alba*.

78. The method of claim 77, wherein the cells further comprise a heterologous nucleic acid encoding an MVA pathway polypeptide.

79. The method of claim 78, wherein the MVA pathway polypeptide is a mevalonate kinase (MVK) polypeptide.

80. The method of claim 79, wherein the MVK polypeptide is from the genus *Methanosarcina*.

81. The method of claim 80, wherein the MVK polypeptide is from *Methanosarcina mazei*.

82. The method of claim 81, wherein the cells are bacterial cells.

83. The method of claim 82, wherein the cells are gram-positive bacterial cells or gram-negative bacterial cells.

84. The method of claim 82, wherein the cells are *Bacillus subtilis* cells or *Escherichia coli* or *Pantoea citrea* cells.

85. The method of claim 81, wherein the cells are fungal cells.

86. The method of claim 85, wherein the cells are *Trichoderma reesei* cells.

87. The method of claim 85, wherein the cells are yeast cells.

88. The method of claim 87, wherein the cells are *Saccharomyces cerevisiae* or *Yarrowia lipolytica* cells.

89. The method of claim 1, further comprising the step of recovering the isoprene.

90. The method of claims 38, further comprising recovery.

91. The improved method 40, wherein the permeate pump is a peristaltic pump.

* * * * *